US012049510B2

(12) United States Patent
Pulé et al.

(10) Patent No.: US 12,049,510 B2
(45) Date of Patent: Jul. 30, 2024

(54) CHIMERIC ANTIGEN RECEPTOR

(71) Applicant: AUTOLUS LIMITED, London (GB)

(72) Inventors: Martin Pulé, London (GB); Shaun Cordoba, London (GB); Simon Thomas, London (GB); Shimobi Onuoha, London (GB); Mathieu Ferrari, London (GB); Wen Chean Lim, London (GB); Biao Ma, London (GB)

(73) Assignee: AUTOLUS LIMITED, London (GB)

( * ) Notice: Subject to any disclaimer, the term of this patent is extended or adjusted under 35 U.S.C. 154(b) by 797 days.

(21) Appl. No.: 17/279,874

(22) PCT Filed: Sep. 26, 2019

(86) PCT No.: PCT/GB2019/052726
§ 371 (c)(1),
(2) Date: Mar. 25, 2021

(87) PCT Pub. No.: WO2020/065330
PCT Pub. Date: Apr. 2, 2020

(65) Prior Publication Data
US 2022/0033509 A1 Feb. 3, 2022

(30) Foreign Application Priority Data

Sep. 27, 2018 (GB) ........................... 1815775
Feb. 14, 2019 (GB) ........................... 1902021

(51) Int. Cl.
*A61P 35/00* (2006.01)
*A61K 35/17* (2015.01)
*C07K 16/28* (2006.01)

(52) U.S. Cl.
CPC .......... *C07K 16/2878* (2013.01); *A61K 35/17* (2013.01); *A61P 35/00* (2018.01); *C07K 16/2803* (2013.01); *C07K 2317/31* (2013.01); *C07K 2317/55* (2013.01); *C07K 2319/03* (2013.01)

(58) Field of Classification Search
CPC . C07K 16/2878; C07K 16/2803; A61P 35/00; A61K 35/17
See application file for complete search history.

(56) References Cited

U.S. PATENT DOCUMENTS

| 10,160,794 B2 | 12/2018 | Pule et al. |
| 10,294,304 B2 | 5/2019 | Kuo et al. |
| 10,919,951 B2 | 2/2021 | Pule et al. |
| 11,058,722 B2 | 7/2021 | Puléet al. |
| 2007/0071675 A1 | 3/2007 | Wu et al. |
| 2016/0200813 A1* | 7/2016 | Benatuil ............... C07K 14/705 435/69.6 |
| 2016/0237139 A1 | 8/2016 | Pule et al. |
| 2017/0362297 A1 | 12/2017 | Marasco |
| 2018/0147271 A1 | 5/2018 | Morgan et al. |
| 2019/0100571 A1 | 4/2019 | Pule et al. |
| 2021/0101959 A1 | 4/2021 | Pule et al. |
| 2023/0074436 A1* | 3/2023 | Guo ........................ C07K 16/18 |

FOREIGN PATENT DOCUMENTS

| CN | 105777911 A | 7/2016 |
| CN | 107406518 A | 11/2017 |
| CN | 107980046 A | 5/2018 |
| WO | WO-01/77342 A1 | 10/2001 |
| WO | WO-2009/114585 A1 | 9/2009 |
| WO | WO-2013/154760 A1 | 10/2013 |
| WO | WO-2015/052538 A1 | 4/2015 |
| WO | WO-2015/069922 A2 | 5/2015 |
| WO | WO-2015/075469 A1 | 5/2015 |
| WO | WO-2015/075470 A1 | 5/2015 |
| WO | WO-2015/150771 A1 | 10/2015 |
| WO | WO-2016/014565 A2 | 1/2016 |
| WO | WO-2016/014789 A2 | 1/2016 |
| WO | WO-2016/030691 A1 | 3/2016 |
| WO | WO-2016/090337 A1 | 6/2016 |
| WO | WO-2016/094304 A2 | 6/2016 |
| WO | WO-2016/100985 A2 | 6/2016 |
| WO | WO-2016/102965 A1 | 6/2016 |
| WO | WO-2016/124930 A1 | 8/2016 |
| WO | WO-2016/139487 A1 | 9/2016 |
| WO | WO-2016/151315 A1 | 9/2016 |
| WO | WO-2016/201300 A1 | 12/2016 |
| WO | WO-2017/029511 A1 | 2/2017 |
| WO | WO-2017/029512 A1 | 2/2017 |
| WO | WO-2017/072361 A1 | 5/2017 |
| WO | WO-2017/156479 A1 | 9/2017 |

(Continued)

OTHER PUBLICATIONS

Friedman et al. Effective Targeting of Multiple B-Cell Maturation Antigen-Expressing Hematological Malignances by Anti-B-Cell Maturation Antigen Chimeric Antigen Receptor T Cells. Human Gene Therapy. Publishes Online Mar. 8, 2018. vol. 29, No. 5, p. 585-601. (Year: 2018).*
Sequence Alignment of Seq ID No. 76 of U.S. Patent Application Publication 2016/0200813 with instant Seq ID No. 29. Search Conducted on Feb. 26, 2024. 1 page. (Year: 2024).*
Sequence Alignment of BDB23358 with instant Seq ID No. 29. Search Conducted on Feb. 26, 2024. 2 pages. (Year: 2024).*
Sequence Alignment of Seq ID No. 40 of U.S. Patent Application Publication No. 2023/0074436 with instant Seq ID No. 30. Search Conducted on Feb. 26, 2024. 1 page. (Year: 2024).*
Sequence Alignment of BJB94750 with instant Seq ID No. 30. Search Conducted on Feb. 26, 2024. 2 pages. (Year: 2024).*
U.S. Appl. No. 18/321,400, filed May 22, 2023.

(Continued)

*Primary Examiner* — Channing S Mahatan
(74) *Attorney, Agent, or Firm* — MARSHALL, GERSTEIN & BORUN LLP

(57) ABSTRACT

The present invention provides a chimeric antigen receptor (CAR) which binds a low density target antigen, which comprises a Fab antigen binding domain. The invention also relates to cells expressing such a CAR and their use in the treatment of disease.

14 Claims, 11 Drawing Sheets

Specification includes a Sequence Listing.

(56) References Cited

FOREIGN PATENT DOCUMENTS

| WO | WO-2017/173349 A1 | 10/2017 |
| WO | WO-2019/090003 A1 | 5/2019 |
| WO | WO-2019/150133 A1 | 8/2019 |
| WO | WO-2020/018825 A1 | 1/2020 |

OTHER PUBLICATIONS

Pan et al., "Blocking Neuropilin-1 Function Has an Additive Effect with Anti-VEGF to Inhibit Tumor Growth", Cancer Cell, 11:53-67 (2007).
Roitt et al., "Immunology", Moscow, pp. 110-111 (2000).
Singer et al., "Genes and Genomes", Moscow, 1:63-64 (1998).
Carpenter et al., "B-cell Muturation Antigen Is a Promising Target for Adoptive T-cell Therapy to Multiple Myeloma," Clin Cancer Res 19(8):2048-60 (2013).
Donnelly et al., "'The cleavage' activities of foot-and-mouth disease virus 2A site-directed mutants and naturally occurring '2A-like' sequences," Journal of General Virology 82:1027-1041 (2001).
Fry et al., "CD22-CAR T Cells Induce Remissions in CD19-CAR Naive and Resistant B-ALL," Nat. Med. 24(1):20-28 (2018).
Huang et al., "IGF1R- and ROR1-Specific CAR T Cells as a Potential Therapy for High Risk Sarcomas," PLoS One 10(7):18 pages (2015).
Hymowitz et al., "Structures of APRIL-Receptor Complexes," The Journal of Biological Chemistry, 280(8):7218-7227 (2005).
International Search Report and Written Opinion from International Application No. PCT/GB2019/052726 dated Apr. 8, 2020.
Nolan et al., "Bypassing Immunization: Optimized Design of "Designer T Cells" against Carcinoembryonic Antigen (CEA)-expressing Tumors, and Lack of Suppression by Soluble CEA," Clinical Cancer Research 5:3928-3941 (1999).
Peng et al., "Mining Naive Rabbit Antibody Repertoires by Phage Display for Monoclonal Antibodies of Therapeutic Utility," J Mol Biol 429(19):2954-2973 (2017).
Walker et al., "Tumor Antigen and Receptor Densities Regulate Efficacy of a Chimeric Antigen Receptor Targeting Anaplastic Lymphoma Kinase," Mol. Ther. 25:2189-2201 (2017).
Yang et al., "Therapeutic Potential and Challenges of Targeting Receptor Tyrosie Kinase ROR1 with Monoclonal Antibodies in B-Cell Malignancies," PLoS One 6(6), 15 pages (2011).
Brunner T., et al., "Cytotoxic T cells: Double-Barreled Shot Guns," Nature Medicine, Abstract, vol. 5, No. 1, 1999, pp. 20.
Koiko P., et al., "Immunology," Translated from English, Edited by Serebryanoy N.B., Moscow, Academy, 2008, p. 37.

* cited by examiner (a) No target antigen (b) High density target antigen (c) Low density target antigen

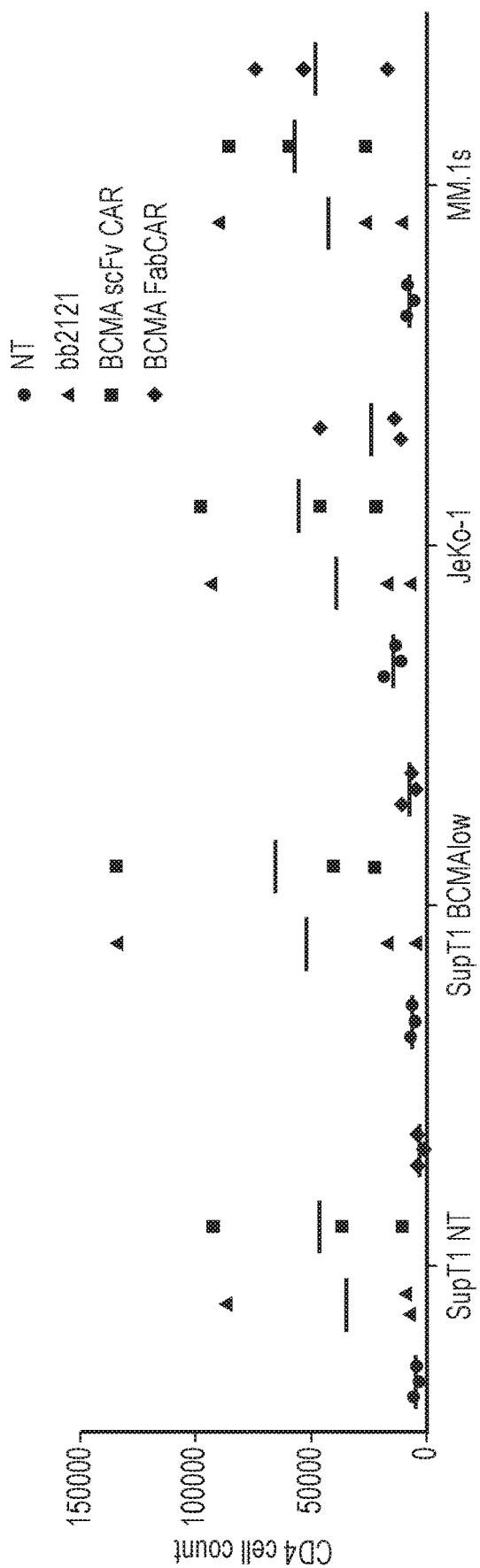
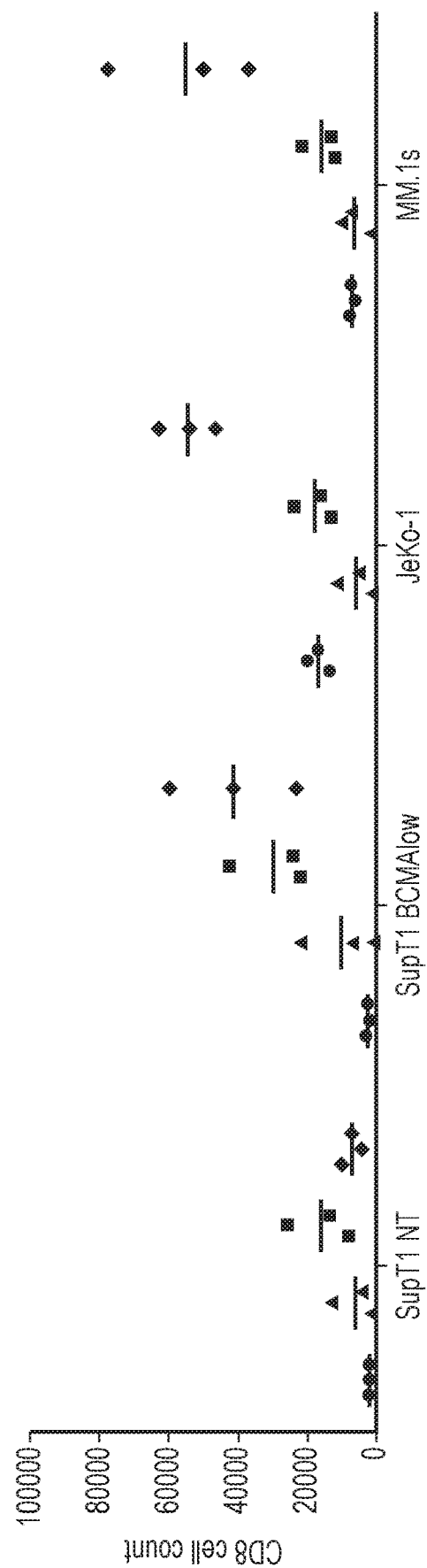
FIG. 8A
FIG. 8B

SEQUENCE LISTING

<160> NUMBER OF SEQ ID NOS: 88

<210> SEQ ID NO 1
<211> LENGTH: 106
<212> TYPE: PRT
<213> ORGANISM: Artificial Sequence
<220> FEATURE:
<223> OTHER INFORMATION: kappa chain constant domain

<400> SEQUENCE: 1

```
Thr Val Ala Ala Pro Ser Val Phe Ile Phe Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105
```

<210> SEQ ID NO 2
<211> LENGTH: 97
<212> TYPE: PRT
<213> ORGANISM: Artificial Sequence
<220> FEATURE:
<223> OTHER INFORMATION: sequence from a gamma immunoglobulin heavy
      chain

<400> SEQUENCE: 2

```
Ser Thr Lys Gly Pro Ser Val Phe Pro Leu Ala Pro Ser Ser Lys Ser
1               5                   10                  15

Thr Ser Gly Gly Thr Ala Ala Leu Gly Cys Leu Val Lys Asp Tyr Phe
            20                  25                  30

Pro Glu Pro Val Thr Val Ser Trp Asn Ser Gly Ala Leu Thr Ser Gly
        35                  40                  45

Val His Thr Phe Pro Ala Val Leu Gln Ser Ser Gly Leu Tyr Ser Leu
    50                  55                  60

Ser Ser Val Val Thr Val Pro Ser Ser Ser Leu Gly Thr Gln Thr Tyr
65                  70                  75                  80

Ile Cys Asn Val Asn His Lys Pro Ser Asn Thr Lys Val Asp Lys Arg
                85                  90                  95

Val
```

<210> SEQ ID NO 3
<211> LENGTH: 20
<212> TYPE: PRT
<213> ORGANISM: Artificial Sequence
<220> FEATURE:
<223> OTHER INFORMATION: spacer, human IgG1 hinge

<400> SEQUENCE: 3

```
Ala Glu Pro Lys Ser Pro Asp Lys Thr His Thr Cys Pro Pro Cys Pro
1               5                   10                  15

Lys Asp Pro Lys
            20
```

```
<210> SEQ ID NO 4
<211> LENGTH: 15
<212> TYPE: PRT
<213> ORGANISM: Artificial Sequence
<220> FEATURE:
<223> OTHER INFORMATION: spacer, hinge spacer

<400> SEQUENCE: 4

Glu Pro Lys Ser Cys Asp Lys Thr His Thr Cys Pro Pro Cys Pro
1               5                   10                  15

<210> SEQ ID NO 5
<211> LENGTH: 124
<212> TYPE: PRT
<213> ORGANISM: Artificial Sequence
<220> FEATURE:
<223> OTHER INFORMATION: anti-BCMA (B cell maturation target) Ab1 VH
      (heavy chain variable region)

<400> SEQUENCE: 5

Gln Ile Gln Leu Val Gln Ser Gly Pro Glu Leu Val Lys Pro Gly Ser
1               5                   10                  15

Ser Val Lys Leu Ser Cys Lys Thr Ser Gly Phe Thr Phe Ser Asp Ser
            20                  25                  30

Tyr Met Ser Trp Leu Lys Gln Val Pro Gly Gln Ser Ile Glu Trp Ile
        35                  40                  45

Gly Asn Ile Tyr Ala Gly Asp Gly Ala Thr His Tyr His Gln Lys Phe
    50                  55                  60

Lys Gly Lys Ala Thr Leu Thr Val Asp Thr Ser Ser Thr Ala Tyr
65                  70                  75                  80

Met Asp Leu Ser Ser Leu Thr Ser Glu Asp Ser Ala Leu Tyr Phe Cys
                85                  90                  95

Ala Arg Pro Leu Tyr Thr Thr Ala Tyr Tyr Tyr Val Gly Gly Phe Ala
            100                 105                 110

Tyr Trp Gly Gln Gly Thr Leu Val Thr Val Ser Ser
        115                 120

<210> SEQ ID NO 6
<211> LENGTH: 113
<212> TYPE: PRT
<213> ORGANISM: Artificial Sequence
<220> FEATURE:
<223> OTHER INFORMATION: anti-BCMA Ab1 VL (light chain variable region)

<400> SEQUENCE: 6

Asp Ile Val Met Thr Gln Ser Pro Ser Ser Leu Ala Val Ser Ala Gly
1               5                   10                  15

Glu Thr Val Thr Ile Asn Cys Lys Ser Ser Gln Ser Leu Leu Ser Ser
            20                  25                  30

Gly Asn Gln Lys Asn Tyr Leu Ala Trp Tyr Gln Gln Lys Pro Gly Gln
        35                  40                  45

Ser Pro Lys Leu Leu Ile Tyr Trp Ala Ser Thr Arg Gln Ser Gly Val
    50                  55                  60

Pro Asp Arg Phe Ile Gly Ser Gly Ser Gly Thr Asp Phe Thr Leu Thr
65                  70                  75                  80

Ile Ser Ser Val Gln Ala Glu Asp Leu Ala Ile Tyr Tyr Cys Gln Gln
                85                  90                  95

Tyr Tyr Asp Thr Pro Leu Thr Phe Gly Ser Gly Thr Lys Leu Glu Ile
            100                 105                 110
```

Lys

<210> SEQ ID NO 7
<211> LENGTH: 121
<212> TYPE: PRT
<213> ORGANISM: Artificial Sequence
<220> FEATURE:
<223> OTHER INFORMATION: anti-BCMA Ab2 VH

<400> SEQUENCE: 7

```
Glu Val Lys Leu Val Glu Ser Gly Gly Gly Leu Val Gln Pro Gly Arg
1               5                   10                  15

Ser Leu Lys Leu Ser Cys Thr Ala Ser Gly Phe Thr Phe Ser Asn Tyr
            20                  25                  30

Asp Met Ala Trp Val Arg Gln Ala Pro Thr Lys Gly Leu Glu Trp Val
        35                  40                  45

Ala Ser Ile Ser Thr Ser Gly Asp Thr Ile Tyr Tyr Arg Asp Ser Val
    50                  55                  60

Lys Gly Arg Phe Thr Val Ser Arg Asp Lys Ala Lys Ser Thr Leu Tyr
65                  70                  75                  80

Leu Gln Met Asp Ser Leu Arg Ser Glu Asp Thr Ala Thr Tyr Tyr Cys
                85                  90                  95

Ala Arg His Asp Tyr Tyr Asp Gly Tyr Gln Ser Phe Ala Tyr Trp Gly
            100                 105                 110

Gln Gly Thr Leu Val Thr Val Ser Ser
        115                 120
```

<210> SEQ ID NO 8
<211> LENGTH: 107
<212> TYPE: PRT
<213> ORGANISM: Artificial Sequence
<220> FEATURE:
<223> OTHER INFORMATION: anti-BCMA Ab2 VL

<400> SEQUENCE: 8

```
Asn Thr Val Met Thr Gln Ser Pro Thr Ser Met Ser Ile Ser Val Gly
1               5                   10                  15

Asp Arg Val Thr Met Asn Cys Lys Ala Ser Gln Asn Val Gly Asn Asn
            20                  25                  30

Ile Ala Trp Tyr Gln Gln Lys Pro Gly Gln Ser Pro Lys Leu Leu Ile
        35                  40                  45

Tyr Tyr Ala Ser Asn Arg Tyr Thr Gly Val Pro Asp Arg Phe Thr Gly
    50                  55                  60

Ser Gly Ser Gly Thr Asp Phe Thr Leu Thr Ile Asn Ser Val Gln Ala
65                  70                  75                  80

Glu Asp Ala Ala Phe Tyr Tyr Cys Gln Arg Ile Tyr Asn Ser Ala Leu
                85                  90                  95

Thr Phe Gly Ser Gly Thr Lys Leu Glu Ile Lys
            100                 105
```

<210> SEQ ID NO 9
<211> LENGTH: 120
<212> TYPE: PRT
<213> ORGANISM: Artificial Sequence
<220> FEATURE:
<223> OTHER INFORMATION: anti-BCMA Ab3 VH

<400> SEQUENCE: 9

Gln Val Gln Leu Gln Gln Ser Gly Ala Ala Leu Val Lys Pro Gly Ala

-continued

```
                1               5                  10                  15
            Ser Val Lys Met Ser Cys Lys Ala Ser Gly Tyr Thr Phe Thr Asp Tyr
                        20                  25                  30

Trp Val Ser Trp Val Lys Gln Ser His Gly Lys Ser Leu Glu Trp Ile
                        35                  40                  45

Gly Glu Ile Tyr Pro Asn Ser Gly Pro Thr Asn Phe Asn Lys Lys Phe
                        50                  55                  60

Lys Gly Lys Ala Thr Leu Thr Val Asp Lys Ser Thr Ser Thr Ala Tyr
             65                  70                  75                  80

Met Glu Leu Ser Arg Leu Thr Ser Glu Asp Ser Ala Ile Tyr Tyr Cys
                        85                  90                  95

Thr Pro Arg Thr Val Ala Pro Tyr Asn Trp Phe Ala Tyr Trp Gly Gln
                        100                 105                 110

Gly Thr Leu Val Thr Val Ser Ser
                        115                 120
```

<210> SEQ ID NO 10
<211> LENGTH: 106
<212> TYPE: PRT
<213> ORGANISM: Artificial Sequence
<220> FEATURE:
<223> OTHER INFORMATION: anti-BCMA Ab3 VL

<400> SEQUENCE: 10

```
            Asp Ile Val Leu Thr Gln Ser Pro Ala Leu Ala Val Ser Pro Gly Glu
             1               5                  10                  15

Arg Val Ser Ile Ser Cys Arg Ala Ser Glu Ser Val Ser Thr Arg Met
                        20                  25                  30

His Trp Tyr Gln Gln Lys Pro Gly Gln Pro Lys Leu Leu Ile Tyr
                        35                  40                  45

Gly Ala Ser Asn Leu Glu Ser Gly Val Pro Ala Arg Phe Ser Gly Ser
                        50                  55                  60

Gly Ser Gly Thr Asp Phe Thr Leu Thr Ile Asp Pro Val Glu Ala Asp
             65                  70                  75                  80

Asp Thr Ala Thr Tyr Phe Cys Gln Gln Ser Trp Asn Asp Pro Tyr Thr
                        85                  90                  95

Phe Gly Ala Gly Thr Lys Leu Glu Leu Lys
                        100                 105
```

<210> SEQ ID NO 11
<211> LENGTH: 121
<212> TYPE: PRT
<213> ORGANISM: Artificial Sequence
<220> FEATURE:
<223> OTHER INFORMATION: anti-BCMA Ab4 VH

<400> SEQUENCE: 11

```
            Glu Val Gln Leu Val Glu Ser Gly Gly Gly Leu Val Gln Pro Gly Arg
             1               5                  10                  15

Ser Leu Lys Leu Ser Cys Ser Ala Ser Gly Phe Ile Phe Ser Asn Phe
                        20                  25                  30

Asp Met Ala Trp Val Arg Gln Ala Pro Arg Lys Gly Leu Glu Trp Val
                        35                  40                  45

Ala Ser Ile Thr Thr Ser Gly Gly Asp Thr His Tyr Arg Asp Ser Val
                        50                  55                  60

Lys Gly Arg Phe Thr Val Ser Arg His Asn Ala Lys Ser Thr Leu Tyr
             65                  70                  75                  80
```

-continued

```
Leu Gln Met Asp Ser Leu Arg Ser Glu Asp Thr Ala Thr Tyr Tyr Cys
                85                  90                  95

Ala Arg His Val Tyr Tyr Gly Leu Phe Trp Phe Phe Asp Phe Trp Gly
            100                 105                 110

Pro Gly Thr Met Val Thr Val Ser Ser
        115                 120

<210> SEQ ID NO 12
<211> LENGTH: 108
<212> TYPE: PRT
<213> ORGANISM: Artificial Sequence
<220> FEATURE:
<223> OTHER INFORMATION: anti-BCMA Ab4 VL

<400> SEQUENCE: 12

Asn Thr Val Met Thr Gln Ser Pro Lys Ser Phe Ile Ser Val Gly
1               5                   10                  15

Asp Arg Val Thr Val Asn Cys Lys Ala Ser Gln Asn Val Gly Thr Asn
            20                  25                  30

Val Asp Trp Tyr Gln Gln Lys Thr Gly Gln Ser Pro Lys Leu Leu Ile
        35                  40                  45

Tyr Gly Ala Ser Asn Arg Tyr Thr Gly Val Pro Asp Arg Phe Thr Gly
    50                  55                  60

Ser Gly Ser Gly Thr Asp Phe Thr Phe Thr Ile Ser Asn Met Gln Ala
65                  70                  75                  80

Glu Asp Leu Ala Val Tyr Tyr Cys Met Gln Ser Asn Thr Asn Pro Phe
                85                  90                  95

Thr Phe Gly Ala Gly Thr Lys Leu Glu Leu Lys Arg
            100                 105

<210> SEQ ID NO 13
<211> LENGTH: 121
<212> TYPE: PRT
<213> ORGANISM: Artificial Sequence
<220> FEATURE:
<223> OTHER INFORMATION: anti-BCMA Ab5 VH

<400> SEQUENCE: 13

Glu Val Gln Leu Val Glu Ser Gly Gly Gly Leu Val Gln Pro Gly Arg
1               5                   10                  15

Ser Leu Lys Leu Ser Cys Thr Ala Ser Gly Phe Thr Phe Ser Asn Tyr
            20                  25                  30

Asp Met Ala Trp Val Arg Gln Ala Pro Thr Lys Gly Leu Glu Trp Val
        35                  40                  45

Ala Ser Ile Ser Thr Ser Gly Asp Thr Ile Tyr Tyr Arg Asp Ser Val
    50                  55                  60

Lys Gly Arg Phe Thr Val Ser Arg Asp Lys Ala Lys Ser Thr Leu Tyr
65                  70                  75                  80

Leu Gln Met Asp Ser Leu Arg Ser Glu Asp Thr Ala Thr Tyr Tyr Cys
                85                  90                  95

Ala Arg His Asp Tyr Tyr Asp Gly Tyr Gln Ser Phe Ala Tyr Trp Gly
            100                 105                 110

Gln Gly Thr Leu Val Thr Val Ser Ser
        115                 120

<210> SEQ ID NO 14
<211> LENGTH: 108
<212> TYPE: PRT
<213> ORGANISM: Artificial Sequence
```

<220> FEATURE:
<223> OTHER INFORMATION: anti-BCMA Ab5 VL

<400> SEQUENCE: 14

Asp Ile Val Met Thr Gln Ser Pro Ser Thr Leu Pro Ala Ser Leu Gly
1               5                   10                  15

Glu Arg Val Thr Ile Ser Cys Arg Ala Ser Gln Ser Ile Ser Asn Tyr
            20                  25                  30

Leu Asn Trp Tyr Gln Gln Lys Pro Asp Gly Thr Ile Lys Pro Leu Ile
        35                  40                  45

Tyr Tyr Thr Ser Asn Leu Gln Ser Gly Val Pro Ser Arg Phe Ser Gly
    50                  55                  60

Ser Gly Ser Gly Thr Asp Tyr Ser Leu Thr Ile Ser Ser Leu Glu Pro
65                  70                  75                  80

Glu Asp Phe Ala Met Tyr Tyr Cys Gln Gln Asp Ala Ser Phe Pro Trp
                85                  90                  95

Thr Phe Gly Gly Gly Thr Lys Leu Glu Leu Lys Arg
            100                 105

<210> SEQ ID NO 15
<211> LENGTH: 119
<212> TYPE: PRT
<213> ORGANISM: Artificial Sequence
<220> FEATURE:
<223> OTHER INFORMATION: anti-BCMA Ab6 VH

<400> SEQUENCE: 15

Glu Val Gln Leu Gln Glu Ser Gly Pro Gly Leu Val Lys Pro Ser Gln
1               5                   10                  15

Ser Leu Ser Leu Thr Cys Ser Val Thr Gly Tyr Pro Ile Thr Asn Asn
            20                  25                  30

Tyr Asp Trp Ser Trp Ile Arg Gln Phe Pro Gly Asn Lys Met Glu Trp
        35                  40                  45

Met Gly Tyr Ile Ser Asp Ser Gly Asn Thr Asn Tyr Asn Pro Ser Leu
    50                  55                  60

Lys Ser Arg Ile Ser Ile Thr Arg Asp Thr Ser Lys Asn Gln Phe Phe
65                  70                  75                  80

Leu Gln Leu Asn Ser Val Thr Thr Glu Asp Thr Ala Thr Tyr Tyr Cys
                85                  90                  95

Ala Ser Gly Tyr Ile Ser Tyr Ile Pro Phe Ala Phe Trp Gly Gln Gly
            100                 105                 110

Thr Leu Val Thr Val Ser Ser
        115

<210> SEQ ID NO 16
<211> LENGTH: 111
<212> TYPE: PRT
<213> ORGANISM: Artificial Sequence
<220> FEATURE:
<223> OTHER INFORMATION: anti-BCMA Ab6 VL

<400> SEQUENCE: 16

Asp Ile Val Leu Thr Gln Ser Pro Ala Leu Ala Val Ser Leu Gly Gln
1               5                   10                  15

Arg Ala Thr Ile Ser Cys Arg Ala Ser Gln Ser Val Ser Ile Ser Ser
            20                  25                  30

Tyr Asn Leu Met Gln Trp Tyr Gln Gln Lys Pro Gly Gln Gln Pro Lys
        35                  40                  45

```
Leu Leu Ile Tyr Asp Ala Ser Asn Leu Ala Ser Gly Ile Pro Ala Arg
 50                  55                  60

Phe Ser Gly Ser Gly Ser Gly Thr Asp Phe Thr Leu Thr Ile Asp Pro
 65                  70                  75                  80

Val Gln Ala Asp Asp Ile Ala Thr Tyr Tyr Cys Gln Gln Ser Lys Asp
                 85                  90                  95

Asp Pro Asn Thr Phe Gly Ala Gly Thr Lys Leu Glu Ile Lys Arg
            100                 105                 110
```

<210> SEQ ID NO 17
<211> LENGTH: 119
<212> TYPE: PRT
<213> ORGANISM: Artificial Sequence
<220> FEATURE:
<223> OTHER INFORMATION: anti-BCMA Ab7 VH

<400> SEQUENCE: 17

```
Glu Val Gln Leu Gln Glu Ser Gly Pro Gly Leu Val Gln Pro Ser Gln
 1               5                  10                  15

Thr Leu Ser Leu Thr Cys Ser Val Thr Gly Tyr Pro Ile Thr Asn Asn
             20                  25                  30

Tyr Asp Trp Ser Trp Ile Arg Lys Phe Pro Gly Asn Lys Met Glu Trp
         35                  40                  45

Met Gly Tyr Ile Ser Asp Ser Gly Ser Thr Asn Tyr Asn Pro Ser Leu
 50                  55                  60

Lys Ser Arg Ile Ser Ile Thr Arg Asp Thr Ser Lys Asn Gln Phe Phe
 65                  70                  75                  80

Leu Gln Leu Asn Ser Val Thr Thr Glu Asp Thr Ala Thr Tyr Tyr Cys
                 85                  90                  95

Ala Ser Gly Tyr Ile Ser Tyr Ile Pro Phe Gly Phe Trp Gly Gln Gly
            100                 105                 110

Thr Leu Val Thr Val Ser Ser
        115
```

<210> SEQ ID NO 18
<211> LENGTH: 106
<212> TYPE: PRT
<213> ORGANISM: Artificial Sequence
<220> FEATURE:
<223> OTHER INFORMATION: anti-BCMA Ab7 VL

<400> SEQUENCE: 18

```
Asp Ile Val Leu Thr Gln Ser Pro Ala Leu Ala Val Ser Pro Gly Glu
 1               5                  10                  15

Arg Val Thr Ile Ser Cys Arg Ala Ser Glu Ser Val Ser Thr Arg Met
             20                  25                  30

His Trp Tyr Gln Gln Lys Pro Gly Gln Gln Pro Lys Leu Leu Ile Tyr
         35                  40                  45

Gly Ala Ser Asn Leu Glu Ser Gly Val Pro Ala Arg Phe Ser Gly Ser
 50                  55                  60

Gly Ser Gly Thr Asp Phe Thr Leu Thr Ile Asp Pro Val Glu Ala Asp
 65                  70                  75                  80

Asp Thr Ala Thr Tyr Phe Cys Gln Gln Ser Trp Asn Asp Pro Pro Thr
                 85                  90                  95

Phe Gly Ser Gly Thr Lys Leu Glu Ile Lys
            100                 105
```

<210> SEQ ID NO 19

```
<211> LENGTH: 121
<212> TYPE: PRT
<213> ORGANISM: Artificial Sequence
<220> FEATURE:
<223> OTHER INFORMATION: anti-BCMA Ab8 VH

<400> SEQUENCE: 19

Glu Val Gln Leu Val Glu Ser Gly Gly Gly Leu Val Gln Pro Gly Arg
1               5                   10                  15

Ser Leu Lys Leu Ser Cys Thr Ala Ser Gly Phe Thr Phe Ser Asn Tyr
            20                  25                  30

Asp Met Ala Trp Val Arg Gln Ala Pro Thr Lys Gly Leu Glu Trp Val
        35                  40                  45

Ala Ser Ile Ser Thr Ser Gly Asp Thr Ile Tyr Tyr Arg Asp Ser Val
    50                  55                  60

Lys Gly Arg Phe Thr Val Ser Arg Asp Lys Ala Lys Ser Thr Leu Tyr
65                  70                  75                  80

Leu Gln Met Asp Ser Leu Arg Ser Glu Asp Thr Ala Thr Tyr Tyr Cys
                85                  90                  95

Ala Arg His Asp Tyr Tyr Asp Gly Tyr Gln Ser Phe Ala Tyr Trp Gly
            100                 105                 110

Gln Gly Thr Leu Val Thr Val Ser Ser
        115                 120

<210> SEQ ID NO 20
<211> LENGTH: 113
<212> TYPE: PRT
<213> ORGANISM: Artificial Sequence
<220> FEATURE:
<223> OTHER INFORMATION: anti-BCMA Ab8 VL

<400> SEQUENCE: 20

Asp Ile Val Met Thr Gln Ser Pro Ala Ser Gln Ala Val Ser Ala Gly
1               5                   10                  15

Glu Lys Val Thr Met Ser Cys Lys Ser Ser Gln Ser Leu Leu Tyr Ser
            20                  25                  30

Gly Asp Gln Lys Asn Tyr Leu Ala Trp Tyr Gln Gln Lys Pro Gly Gln
        35                  40                  45

Ser Pro Lys Leu Leu Ile Tyr Leu Ala Ser Thr Arg Glu Ser Gly Val
    50                  55                  60

Pro Asp Arg Phe Ile Gly Ser Gly Ser Gly Thr Asp Phe Thr Leu Thr
65                  70                  75                  80

Ile Ser Ser Val Gln Ala Glu Asp Leu Ala Asp Tyr Tyr Cys Gln Gln
                85                  90                  95

His Tyr Ser Tyr Pro Leu Thr Phe Gly Ser Gly Thr Lys Leu Glu Ile
            100                 105                 110

Lys

<210> SEQ ID NO 21
<211> LENGTH: 121
<212> TYPE: PRT
<213> ORGANISM: Artificial Sequence
<220> FEATURE:
<223> OTHER INFORMATION: anti-BCMA Ab9 VH

<400> SEQUENCE: 21

Glu Val Gln Leu Val Glu Ser Gly Gly Gly Leu Val Gln Pro Gly Arg
1               5                   10                  15

Ser Leu Lys Leu Ser Cys Ala Ala Ser Gly Phe Thr Phe Ser Asn Tyr
```

```
                    20                  25                  30

Asp Met Ala Trp Val Arg Gln Ala Pro Thr Lys Gly Leu Glu Trp Val
        35                  40                  45

Ala Ser Ile Ser Thr Ser Gly Asp Thr Ile Tyr Tyr Arg Asp Ser Val
    50                  55                  60

Lys Gly Arg Phe Thr Val Ser Arg Asp Asn Ala Lys Ser Thr Leu Tyr
65                  70                  75                  80

Leu Gln Met Asp Ser Leu Arg Ser Glu Asp Thr Ala Thr Tyr Tyr Cys
                85                  90                  95

Thr Arg His Gly Tyr Tyr Asp Gly Tyr Gln Ser Phe Asp Tyr Trp Gly
            100                 105                 110

Gln Gly Thr Leu Val Thr Val Ser Ser
        115                 120

<210> SEQ ID NO 22
<211> LENGTH: 107
<212> TYPE: PRT
<213> ORGANISM: Artificial Sequence
<220> FEATURE:
<223> OTHER INFORMATION: anti-BCMA Ab9 VL

<400> SEQUENCE: 22

Asn Thr Val Met Thr Gln Ser Pro Lys Ser Met Ser Ile Ser Val Gly
1               5                  10                  15

Asp Arg Val Thr Met Asn Cys Lys Ala Ser Gln Asn Val Gly Asn Asn
            20                  25                  30

Ile Ala Trp Tyr Gln Gln Lys Pro Gly Gln Ser Pro Lys Leu Leu Ile
        35                  40                  45

Tyr Tyr Ala Ser Asn Arg Tyr Thr Gly Val Pro Asp Arg Phe Thr Gly
    50                  55                  60

Gly Gly Tyr Gly Thr Asp Phe Thr Leu Thr Ile Asn Ser Val Gln Ala
65                  70                  75                  80

Glu Asp Ala Ala Thr Tyr Tyr Cys Gln Gln Trp Asn Tyr Pro Ser Ile
                85                  90                  95

Thr Phe Gly Ser Gly Thr Lys Leu Glu Ile Lys
            100                 105

<210> SEQ ID NO 23
<211> LENGTH: 122
<212> TYPE: PRT
<213> ORGANISM: Artificial Sequence
<220> FEATURE:
<223> OTHER INFORMATION: anti-BCMA Ab10 VH

<400> SEQUENCE: 23

Glu Val Gln Leu Val Glu Ser Gly Gly Gly Leu Val Gln Pro Gly Arg
1               5                  10                  15

Ser Met Lys Leu Ser Cys Ala Ala Ser Gly Phe Thr Phe Ser Asn Tyr
            20                  25                  30

Asp Met Ala Trp Val Arg Gln Ala Pro Thr Lys Gly Leu Glu Trp Val
        35                  40                  45

Ala Ser Ile Ser Pro Ser Gly Gly Ser Thr Tyr Tyr Arg Asp Ser Val
    50                  55                  60

Lys Gly Arg Phe Thr Val Ser Arg Asp Asn Ala Lys Ser Ser Leu Tyr
65                  70                  75                  80

Leu Gln Met Asp Ser Leu Arg Ser Glu Asp Thr Ala Thr Tyr Tyr Cys
                85                  90                  95
```

-continued

```
Thr Arg Gly Asp Tyr Gly Tyr Asn Tyr Ala Tyr Trp Phe Ala Tyr Trp
            100                 105                 110

Gly Gln Gly Thr Leu Val Thr Val Ser Ser
        115                 120

<210> SEQ ID NO 24
<211> LENGTH: 107
<212> TYPE: PRT
<213> ORGANISM: Artificial Sequence
<220> FEATURE:
<223> OTHER INFORMATION: anti-BCMA Ab10 VL

<400> SEQUENCE: 24

Asp Ile Val Met Thr Gln Ala Pro Ser Ser Met Pro Ala Ser Leu Gly
1               5                   10                  15

Glu Arg Val Thr Ile Ser Cys Arg Ala Ser Gln Gly Ile Ser Asn Tyr
            20                  25                  30

Leu Asn Trp Tyr Gln Gln Lys Pro Asp Gly Thr Ile Lys Pro Leu Ile
        35                  40                  45

Tyr Tyr Thr Ser Asn Leu Gln Ser Gly Val Pro Ser Arg Phe Ser Gly
    50                  55                  60

Ser Gly Ser Gly Thr Asp Tyr Ser Leu Thr Ile Ser Ser Leu Glu Pro
65                  70                  75                  80

Glu Asp Phe Ala Met Tyr Tyr Cys Gln Gln Tyr Asp Ser Ser Pro Leu
                85                  90                  95

Thr Phe Gly Ala Gly Thr Lys Leu Glu Leu Lys
            100                 105

<210> SEQ ID NO 25
<211> LENGTH: 121
<212> TYPE: PRT
<213> ORGANISM: Artificial Sequence
<220> FEATURE:
<223> OTHER INFORMATION: anti-BCMA Ab11 VH

<400> SEQUENCE: 25

Glu Val Gln Leu Val Glu Ser Gly Gly Gly Leu Val Gln Pro Gly Arg
1               5                   10                  15

Ser Leu Lys Leu Ser Cys Glu Ala Ser Gly Phe Thr Phe Ser Asn Tyr
            20                  25                  30

Asp Met Ala Trp Val Arg Gln Ala Pro Thr Lys Gly Leu Glu Trp Val
        35                  40                  45

Ala Ser Ile Ser Thr Ser Gly Asp Ser Ile Tyr Tyr Arg Asp Ser Val
    50                  55                  60

Lys Gly Arg Phe Thr Val Ser Arg Asp Asn Val Lys Ser Thr Leu Tyr
65                  70                  75                  80

Leu Gln Met Asp Ser Leu Arg Ser Glu Asp Thr Ala Thr Tyr Tyr Cys
                85                  90                  95

Ala Arg His Gly Tyr Tyr Asp Gly Tyr Gln Ser Phe Asp Tyr Trp Gly
            100                 105                 110

Gln Gly Thr Leu Val Thr Val Ser Ser
        115                 120

<210> SEQ ID NO 26
<211> LENGTH: 107
<212> TYPE: PRT
<213> ORGANISM: Artificial Sequence
<220> FEATURE:
<223> OTHER INFORMATION: anti-BCMA Ab12 VL
```

<400> SEQUENCE: 26

Asp Ile Val Met Thr Gln Ser Pro Ser Leu Pro Ala Ser Leu Gly
1               5                   10                  15

Glu Arg Val Thr Ile Ser Cys Arg Ala Ser Gln Gly Ile Ser Asn Asn
            20                  25                  30

Leu Asn Trp Tyr Gln Gln Lys Pro Asp Gly Thr Ile Lys Pro Leu Ile
        35                  40                  45

Tyr Tyr Thr Ser Asn Leu Gln Ser Gly Val Pro Ser Arg Phe Ser Gly
50                  55                  60

Ser Gly Ser Gly Thr Asp Tyr Ser Leu Thr Ile Ser Ser Leu Glu Pro
65                  70                  75                  80

Glu Asp Phe Ala Thr Tyr Tyr Cys Gln Gln Asp Glu Thr Phe Pro Tyr
                85                  90                  95

Thr Phe Gly Ala Gly Thr Lys Leu Glu Leu Lys
            100                 105

<210> SEQ ID NO 27
<211> LENGTH: 121
<212> TYPE: PRT
<213> ORGANISM: Artificial Sequence
<220> FEATURE:
<223> OTHER INFORMATION: anti-BCMA Ab13 VH

<400> SEQUENCE: 27

Glu Val Gln Leu Val Glu Ser Gly Gly Gly Leu Val Gln Pro Gly Arg
1               5                   10                  15

Ser Leu Lys Leu Ser Cys Ala Ala Ser Gly Phe Thr Phe Ser Asn Tyr
            20                  25                  30

Asp Met Ala Trp Val Arg Gln Ala Pro Thr Lys Gly Leu Glu Trp Val
        35                  40                  45

Ala Ser Ile Ser Pro Ser Gly Gly Ser Thr Tyr Tyr Arg Asp Ser Val
50                  55                  60

Lys Gly Arg Phe Thr Ile Ser Arg Asp Asn Ala Lys Ser Thr Leu Tyr
65                  70                  75                  80

Leu Gln Met Asp Ser Leu Arg Ser Glu Asp Thr Ala Thr Tyr Tyr Cys
                85                  90                  95

Ala Thr His Asn Tyr Tyr Asp Gly Ser Ser Leu Phe Ala Tyr Trp Gly
            100                 105                 110

Gln Gly Thr Leu Val Thr Val Ser Ser
        115                 120

<210> SEQ ID NO 28
<211> LENGTH: 106
<212> TYPE: PRT
<213> ORGANISM: Artificial Sequence
<220> FEATURE:
<223> OTHER INFORMATION: anti-BCMA Ab13 VL

<400> SEQUENCE: 28

Asp Ile Val Leu Thr Gln Ser Pro Ala Leu Ala Val Ser Pro Gly Glu
1               5                   10                  15

Arg Val Thr Ile Ser Cys Gly Ala Asn Glu Thr Val Ser Thr Leu Val
            20                  25                  30

His Trp Tyr Gln Gln Lys Pro Gly Gln Gln Pro Lys Leu Leu Ile Tyr
        35                  40                  45

Leu Ala Ser His Leu Glu Ser Gly Val Pro Ala Arg Phe Ser Gly Ser
50                  55                  60

```
Gly Ser Gly Thr Asp Phe Thr Leu Thr Ile Asp Pro Val Glu Ala Asp
65                  70                  75                  80

Asp Thr Ala Thr Tyr Tyr Cys Gln Gln Ser Trp Asn Asp Pro Pro Thr
                85                  90                  95

Phe Gly Gly Gly Thr Lys Leu Glu Leu Lys
            100                 105

<210> SEQ ID NO 29
<211> LENGTH: 115
<212> TYPE: PRT
<213> ORGANISM: Artificial Sequence
<220> FEATURE:
<223> OTHER INFORMATION: anti-BCMA Ab14 VH

<400> SEQUENCE: 29

Glu Val Gln Leu Val Glu Ser Gly Gly Gly Leu Val Gln Pro Gly Arg
1               5                   10                  15

Ser Leu Lys Leu Ser Cys Ala Ala Ser Gly Phe Ile Phe Ser Asp Tyr
            20                  25                  30

Asn Met Ala Trp Val Arg Gln Ala Pro Lys Lys Gly Leu Glu Trp Val
        35                  40                  45

Ala Thr Ile Ile Tyr Asp Gly Ser Ser Thr Asn His Gly Asp Ser Val
50                  55                  60

Lys Gly Arg Phe Thr Ile Ser Arg Asp Asn Ala Lys Ser Thr Leu Tyr
65                  70                  75                  80

Leu Gln Met Asp Ser Leu Arg Ser Glu Asp Thr Ala Thr Tyr Tyr Cys
                85                  90                  95

Ala Thr Arg Pro Gly Pro Phe Ala Tyr Trp Gly Gln Gly Thr Leu Val
            100                 105                 110

Thr Val Ser
        115

<210> SEQ ID NO 30
<211> LENGTH: 111
<212> TYPE: PRT
<213> ORGANISM: Artificial Sequence
<220> FEATURE:
<223> OTHER INFORMATION: anti-BCMA Ab15 VL

<400> SEQUENCE: 30

Asp Val Val Leu Thr Gln Thr Pro Pro Thr Leu Ser Ala Thr Ile Gly
1               5                   10                  15

Gln Ser Val Ser Ile Ser Cys Arg Ser Ser Gln Ser Leu Leu His Ser
            20                  25                  30

Asn Gly Asn Thr Tyr Leu His Trp Leu Leu Gln Arg Pro Gly Gln Ser
        35                  40                  45

Pro Gln Phe Leu Ile Tyr Leu Val Ser Gly Leu Gly Ser Gly Val Pro
    50                  55                  60

Asn Arg Phe Ser Gly Ser Gly Ser Gly Thr Asp Phe Thr Leu Lys Ile
65                  70                  75                  80

Ser Gly Val Glu Ala Glu Asp Leu Gly Ile Tyr Tyr Cys Val His Gly
                85                  90                  95

Thr His Ala Trp Thr Val Gly Gly Thr Lys Leu Glu Leu Lys
            100                 105                 110

<210> SEQ ID NO 31
<211> LENGTH: 247
<212> TYPE: PRT
<213> ORGANISM: Artificial Sequence
```

<220> FEATURE:
<223> OTHER INFORMATION: transmembrane activator and calcium modulator
       and cyclophilin ligand (CAML) interactor (TACI) binder, 2H6 ScFv

<400> SEQUENCE: 31

Glu Val Gln Leu Gln Gln Ser Gly Pro Glu Leu Val Lys Pro Gly Ala
1               5                   10                  15

Ser Val Arg Met Ser Cys Lys Ala Ser Gly Tyr Thr Phe Thr Asn Tyr
            20                  25                  30

Val Met His Trp Val Lys Gln Lys Pro Gly Gln Gly Leu Glu Trp Ile
        35                  40                  45

Gly Tyr Ile Asn Pro Ser Asn Asp Asp Thr Lys Tyr Thr Glu Lys Phe
    50                  55                  60

Lys Gly Lys Ala Thr Leu Thr Ser Asp Lys Ser Ser Thr Ala Tyr
65                  70                  75                  80

Met Glu Leu Ser Ser Leu Thr Ser Glu Asp Ser Ala Val Tyr Tyr Cys
            85                  90                  95

Ala Arg Gly Thr His Gly Asp Tyr Tyr Ala Leu Asp Tyr Trp Gly Gln
        100                 105                 110

Gly Thr Ser Val Thr Val Ser Ser Gly Gly Gly Ala Gly Gly Gly
    115                 120                 125

Gly Ser Gly Gly Gly Ser Asp Ile Val Leu Thr Gln Ser Pro Ala
130                 135                 140

Ser Leu Ala Val Ser Leu Gly Gln Ser Val Thr Ile Ser Cys Arg Ala
145                 150                 155                 160

Ser Glu Ser Val Glu Tyr Tyr Gly Thr Ser Leu Met Gln Trp Tyr Gln
            165                 170                 175

Gln Lys Pro Gly Gln Ala Pro Lys Leu Leu Ile Tyr Gly Ala Ser Asn
        180                 185                 190

Val Glu Ser Gly Val Pro Ala Arg Phe Ser Gly Ser Gly Ser Gly Thr
    195                 200                 205

Asp Phe Ser Leu Asn Ile His Pro Val Glu Glu Asp Asp Ile Ala Met
    210                 215                 220

Tyr Phe Cys Gln Gln Ser Arg Lys Val Pro Trp Thr Phe Gly Gly Gly
225                 230                 235                 240

Thr Lys Leu Glu Ile Lys Arg
                245

<210> SEQ ID NO 32
<211> LENGTH: 5
<212> TYPE: PRT
<213> ORGANISM: Artificial Sequence
<220> FEATURE:
<223> OTHER INFORMATION: TACI binder 2H6, CDR H1

<400> SEQUENCE: 32

Asn Tyr Val Met His
1               5

<210> SEQ ID NO 33
<211> LENGTH: 17
<212> TYPE: PRT
<213> ORGANISM: Artificial Sequence
<220> FEATURE:
<223> OTHER INFORMATION: TACI binder 2H6, CDR H2

<400> SEQUENCE: 33

Tyr Ile Asn Pro Ser Asn Asp Asp Thr Lys Tyr Thr Glu Lys Phe Lys
1               5                   10                  15

Gly

<210> SEQ ID NO 34
<211> LENGTH: 11
<212> TYPE: PRT
<213> ORGANISM: Artificial Sequence
<220> FEATURE:
<223> OTHER INFORMATION: TACI binder 2H6, CDR H3

<400> SEQUENCE: 34

Gly Thr His Gly Asp Tyr Tyr Ala Leu Asp Tyr
1               5                   10

<210> SEQ ID NO 35
<211> LENGTH: 15
<212> TYPE: PRT
<213> ORGANISM: Artificial Sequence
<220> FEATURE:
<223> OTHER INFORMATION: TACI binder 2H6, CDR L1

<400> SEQUENCE: 35

Arg Ala Ser Glu Ser Val Glu Tyr Tyr Gly Thr Ser Leu Met Gln
1               5                   10                  15

<210> SEQ ID NO 36
<211> LENGTH: 7
<212> TYPE: PRT
<213> ORGANISM: Artificial Sequence
<220> FEATURE:
<223> OTHER INFORMATION: TACI binder 2H6, CDR L2

<400> SEQUENCE: 36

Gly Ala Ser Asn Val Glu Ser
1               5

<210> SEQ ID NO 37
<211> LENGTH: 7
<212> TYPE: PRT
<213> ORGANISM: Artificial Sequence
<220> FEATURE:
<223> OTHER INFORMATION: TACI binder 2H6, CDR L3

<400> SEQUENCE: 37

Gln Gln Ser Arg Lys Val Pro
1               5

<210> SEQ ID NO 38
<211> LENGTH: 245
<212> TYPE: PRT
<213> ORGANISM: Artificial Sequence
<220> FEATURE:
<223> OTHER INFORMATION: TACI binder, 2G2 ScFv

<400> SEQUENCE: 38

Gln Val Thr Leu Lys Glu Ser Gly Pro Gly Met Leu Gln Pro Ser Gln
1               5                   10                  15

Thr Leu Ser Leu Thr Cys Ser Phe Ser Gly Phe Ser Leu Ser Thr Phe
                20                  25                  30

Gly Met Gly Val Gly Trp Ile Arg Gln Pro Ser Gly Lys Gly Leu Glu
            35                  40                  45

Trp Leu Ala His Ile Trp Trp Asp Asp Ala Gln Tyr Ser Asn Pro Ala
    50                  55                  60

Leu Arg Ser Arg Leu Thr Ile Ser Lys Asp Thr Ser Lys Asn Gln Val
65                  70                  75                  80

```
Phe Leu Lys Ile Ala Asn Val Asp Thr Ala Asp Thr Ala Thr Tyr Tyr
                85                  90                  95
Cys Ser Arg Ile His Ser Tyr Tyr Ser Tyr Asp Glu Gly Phe Ala Tyr
            100                 105                 110
Trp Gly Gln Gly Thr Leu Val Thr Val Ser Ser Gly Gly Gly Gly Ser
        115                 120                 125
Gly Gly Gly Gly Ser Gly Gly Gly Ser Asp Ile Val Met Thr Gln
    130                 135                 140
Ser Gln Lys Phe Met Ser Thr Thr Val Gly Asp Arg Val Ser Ile Thr
145                 150                 155                 160
Cys Lys Ala Ser Gln Asn Val Gly Thr Ala Val Ala Trp Tyr Gln Gln
                165                 170                 175
Lys Pro Gly Gln Ser Pro Lys Leu Leu Ile Tyr Ser Ala Ser Asn Arg
            180                 185                 190
Tyr Thr Gly Val Pro Asp Arg Phe Thr Gly Ser Gly Ser Gly Thr Asp
        195                 200                 205
Phe Thr Leu Thr Ile Ser Asn Met Gln Ser Glu Asp Leu Ala Asp Tyr
    210                 215                 220
Phe Cys Gln Gln Tyr Ser Ser Tyr Arg Thr Phe Gly Gly Gly Thr Lys
225                 230                 235                 240

Leu Glu Ile Lys Arg
            245

<210> SEQ ID NO 39
<211> LENGTH: 7
<212> TYPE: PRT
<213> ORGANISM: Artificial Sequence
<220> FEATURE:
<223> OTHER INFORMATION: TACI binder 2G2, CDR H1

<400> SEQUENCE: 39

Thr Phe Gly Met Gly Val Gly
1               5

<210> SEQ ID NO 40
<211> LENGTH: 16
<212> TYPE: PRT
<213> ORGANISM: Artificial Sequence
<220> FEATURE:
<223> OTHER INFORMATION: TACI binder 2G2, CDR H2

<400> SEQUENCE: 40

His Ile Trp Trp Asp Asp Ala Gln Tyr Ser Asn Pro Ala Leu Arg Ser
1               5                   10                  15

<210> SEQ ID NO 41
<211> LENGTH: 14
<212> TYPE: PRT
<213> ORGANISM: Artificial Sequence
<220> FEATURE:
<223> OTHER INFORMATION: TACI binder 2G2, CDR H3

<400> SEQUENCE: 41

Arg Ile His Ser Tyr Tyr Ser Tyr Asp Glu Gly Phe Ala Tyr
1               5                   10

<210> SEQ ID NO 42
<211> LENGTH: 11
<212> TYPE: PRT
<213> ORGANISM: Artificial Sequence
<220> FEATURE:
```

<223> OTHER INFORMATION: TACI binder 2G2, CDR L1

<400> SEQUENCE: 42

Lys Ala Ser Gln Asn Val Gly Thr Ala Val Ala
1               5                   10

<210> SEQ ID NO 43
<211> LENGTH: 7
<212> TYPE: PRT
<213> ORGANISM: Artificial Sequence
<220> FEATURE:
<223> OTHER INFORMATION: TACI binder 2G2, CDR L2

<400> SEQUENCE: 43

Ser Ala Ser Asn Arg Tyr Thr
1               5

<210> SEQ ID NO 44
<211> LENGTH: 6
<212> TYPE: PRT
<213> ORGANISM: Artificial Sequence
<220> FEATURE:
<223> OTHER INFORMATION: TACI binder 2G2, CDR L3

<400> SEQUENCE: 44

Gln Gln Tyr Ser Ser Tyr
1               5

<210> SEQ ID NO 45
<211> LENGTH: 115
<212> TYPE: PRT
<213> ORGANISM: Artificial Sequence
<220> FEATURE:
<223> OTHER INFORMATION: TACI binder, 1G6 VH

<400> SEQUENCE: 45

Gln Val Gln Leu Lys Gln Ser Gly Pro Gly Leu Val Ala Pro Ser Gln
1               5                   10                  15

Ser Leu Ser Ile Thr Cys Thr Val Ser Gly Phe Ser Leu Thr Ser Tyr
                20                  25                  30

Gly Val Asp Trp Val Arg Gln Ser Pro Gly Lys Gly Leu Glu Trp Leu
            35                  40                  45

Gly Ile Ile Trp Gly Gly Gly Arg Thr Asn Tyr Asn Ser Ala Phe Lys
    50                  55                  60

Ser Arg Leu Ser Ile Ser Lys Asp Asn Ser Lys Ser Gln Val Phe Leu
65                  70                  75                  80

Lys Met Asn Ser Leu Gln Thr Asp Asp Thr Ala Met Tyr Tyr Cys Ala
                85                  90                  95

Ser Gly Asp Arg Ala Ala Asp Tyr Trp Gly Gln Gly Thr Ser Val Thr
                100                 105                 110

Val Ser Ser
        115

<210> SEQ ID NO 46
<211> LENGTH: 107
<212> TYPE: PRT
<213> ORGANISM: Artificial Sequence
<220> FEATURE:
<223> OTHER INFORMATION: TACI binder ,1G6 VL

<400> SEQUENCE: 46

Asp Ile Val Met Thr Gln Ser Gln Lys Phe Met Ser Thr Thr Val Gly
1               5                   10                  15

```
Asp Arg Val Thr Ile Thr Cys Lys Ala Ser Gln Asn Val Gly Thr Ala
            20                  25                  30

Val Ala Trp Tyr Gln Gln Lys Pro Gly Gln Ser Pro Lys Leu Leu Ile
        35                  40                  45

Tyr Ser Ala Ser Asn Arg Tyr Thr Gly Val Pro Val Arg Phe Thr Gly
    50                  55                  60

Ser Gly Ser Gly Thr Asp Phe Thr Leu Thr Ile Asn Asn Met Gln Ser
65                  70                  75                  80

Glu Asp Leu Ala Asp Tyr Phe Cys Gln Gln Tyr Ser Ser Tyr Pro Leu
                85                  90                  95

Thr Phe Gly Ala Gly Thr Lys Leu Glu Leu Lys
            100                 105

<210> SEQ ID NO 47
<211> LENGTH: 5
<212> TYPE: PRT
<213> ORGANISM: Artificial Sequence
<220> FEATURE:
<223> OTHER INFORMATION: TACI binder 1G6, CDR H1

<400> SEQUENCE: 47

Ser Tyr Gly Val Asp
1               5

<210> SEQ ID NO 48
<211> LENGTH: 16
<212> TYPE: PRT
<213> ORGANISM: Artificial Sequence
<220> FEATURE:
<223> OTHER INFORMATION: TACI binder 1G6, CDR H2

<400> SEQUENCE: 48

Ile Ile Trp Gly Gly Gly Arg Thr Asn Tyr Asn Ser Ala Phe Lys Ser
1               5                   10                  15

<210> SEQ ID NO 49
<211> LENGTH: 7
<212> TYPE: PRT
<213> ORGANISM: Artificial Sequence
<220> FEATURE:
<223> OTHER INFORMATION: TACI binder 1G6, CDR H3

<400> SEQUENCE: 49

Gly Asp Arg Ala Ala Asp Tyr
1               5

<210> SEQ ID NO 50
<211> LENGTH: 11
<212> TYPE: PRT
<213> ORGANISM: Artificial Sequence
<220> FEATURE:
<223> OTHER INFORMATION: TACI binder 1G6, CDR L1

<400> SEQUENCE: 50

Lys Ala Ser Gln Asn Val Gly Thr Ala Val Ala
1               5                   10

<210> SEQ ID NO 51
<211> LENGTH: 7
<212> TYPE: PRT
<213> ORGANISM: Artificial Sequence
<220> FEATURE:
<223> OTHER INFORMATION: TACI binder 1G6, CDR L2
```

```
<400> SEQUENCE: 51

Ser Ala Ser Asn Arg Tyr Thr
1               5

<210> SEQ ID NO 52
<211> LENGTH: 7
<212> TYPE: PRT
<213> ORGANISM: Artificial Sequence
<220> FEATURE:
<223> OTHER INFORMATION: TACI binder 1G6, CDR L3

<400> SEQUENCE: 52

Gln Gln Tyr Ser Ser Tyr Pro
1               5

<210> SEQ ID NO 53
<211> LENGTH: 114
<212> TYPE: PRT
<213> ORGANISM: Artificial Sequence
<220> FEATURE:
<223> OTHER INFORMATION: TACI binder, 4B11 VH

<400> SEQUENCE: 53

Glu Val Gln Leu Gln Gln Ser Val Ala Glu Leu Val Arg Pro Gly Ala
1               5                   10                  15

Ser Val Lys Leu Ser Cys Thr Ala Ser Gly Phe Asn Ile Lys Asn Thr
            20                  25                  30

Tyr Ile His Trp Val Lys Gln Arg Pro Glu Gln Gly Leu Glu Trp Ile
        35                  40                  45

Gly Lys Ile Asp Pro Ala Asn Gly Asn Ser Glu Tyr Ala Pro Lys Phe
    50                  55                  60

Gln Gly Lys Ala Thr Ile Thr Ala Asp Thr Ser Ser Asn Thr Ala Tyr
65                  70                  75                  80

Leu Gln Leu Ser Ser Leu Thr Ser Glu Asp Thr Thr Ile Tyr Tyr Cys
                85                  90                  95

Thr Ser Gly Tyr Gly Ala Tyr Trp Gly Gln Gly Thr Thr Leu Thr Val
            100                 105                 110

Ser Ser

<210> SEQ ID NO 54
<211> LENGTH: 111
<212> TYPE: PRT
<213> ORGANISM: Artificial Sequence
<220> FEATURE:
<223> OTHER INFORMATION: TACI binder, 4B11 VL

<400> SEQUENCE: 54

Asp Ile Val Leu Ser Gln Ser Pro Ser Ser Leu Ala Val Ser Ile Gly
1               5                   10                  15

Glu Lys Val Thr Leu Ser Cys Lys Ser Ser Gln Ser Leu Leu Tyr Ser
            20                  25                  30

Ser Asn Gln Lys Asn Tyr Leu Ala Trp Phe Gln Gln Lys Pro Gly Gln
        35                  40                  45

Ser Leu Lys Leu Leu Ile Tyr Trp Ala Ser Thr Arg Glu Phe Gly Val
    50                  55                  60

Pro Asp Arg Phe Thr Gly Ser Gly Ser Gly Thr Asp Phe Thr Leu Thr
65                  70                  75                  80

Ile Ser Ser Val Lys Thr Glu Asp Leu Ala Val Tyr Tyr Cys Gln Gln
                85                  90                  95
```

Tyr Tyr Thr Trp Thr Phe Gly Gly Gly Thr Lys Leu Glu Ile Lys
            100                 105                 110

<210> SEQ ID NO 55
<211> LENGTH: 5
<212> TYPE: PRT
<213> ORGANISM: Artificial Sequence
<220> FEATURE:
<223> OTHER INFORMATION: TACI binder 4B11, CDR H1

<400> SEQUENCE: 55

Asn Thr Tyr Ile His
1               5

<210> SEQ ID NO 56
<211> LENGTH: 17
<212> TYPE: PRT
<213> ORGANISM: Artificial Sequence
<220> FEATURE:
<223> OTHER INFORMATION: TACI binder 4B11, CDR H2

<400> SEQUENCE: 56

Lys Ile Asp Pro Ala Asn Gly Asn Ser Glu Tyr Ala Pro Lys Phe Gln
1               5                   10                  15

Gly

<210> SEQ ID NO 57
<211> LENGTH: 5
<212> TYPE: PRT
<213> ORGANISM: Artificial Sequence
<220> FEATURE:
<223> OTHER INFORMATION: TACI binder 4B11, CDR H3

<400> SEQUENCE: 57

Gly Tyr Gly Ala Tyr
1               5

<210> SEQ ID NO 58
<211> LENGTH: 17
<212> TYPE: PRT
<213> ORGANISM: Artificial Sequence
<220> FEATURE:
<223> OTHER INFORMATION: TACI binder 4B11, CDR L1

<400> SEQUENCE: 58

Lys Ser Ser Gln Ser Leu Leu Tyr Ser Ser Asn Gln Lys Asn Tyr Leu
1               5                   10                  15

Ala

<210> SEQ ID NO 59
<211> LENGTH: 7
<212> TYPE: PRT
<213> ORGANISM: Artificial Sequence
<220> FEATURE:
<223> OTHER INFORMATION: TACI binder 4B11, CDR L2

<400> SEQUENCE: 59

Trp Ala Ser Thr Arg Glu Phe
1               5

<210> SEQ ID NO 60
<211> LENGTH: 6
<212> TYPE: PRT
<213> ORGANISM: Artificial Sequence
<220> FEATURE:
<223> OTHER INFORMATION: TACI binder 4B11, CDR L3

```
<400> SEQUENCE: 60

Gln Gln Tyr Tyr Thr Trp
1               5

<210> SEQ ID NO 61
<211> LENGTH: 7
<212> TYPE: PRT
<213> ORGANISM: Artificial Sequence
<220> FEATURE:
<223> OTHER INFORMATION: CD19-binding domain VH CDR, CDR1

<400> SEQUENCE: 61

Gly Tyr Ala Phe Ser Ser Ser
1               5

<210> SEQ ID NO 62
<211> LENGTH: 6
<212> TYPE: PRT
<213> ORGANISM: Artificial Sequence
<220> FEATURE:
<223> OTHER INFORMATION: CD19-binding domain VH CDR, CDR2

<400> SEQUENCE: 62

Tyr Pro Gly Asp Glu Asp
1               5

<210> SEQ ID NO 63
<211> LENGTH: 10
<212> TYPE: PRT
<213> ORGANISM: Artificial Sequence
<220> FEATURE:
<223> OTHER INFORMATION: CD19-binding domain VH CDR, CDR3

<400> SEQUENCE: 63

Ser Leu Leu Tyr Gly Asp Tyr Leu Asp Tyr
1               5                   10

<210> SEQ ID NO 64
<211> LENGTH: 10
<212> TYPE: PRT
<213> ORGANISM: Artificial Sequence
<220> FEATURE:
<223> OTHER INFORMATION: CD19-binding domain VL CDR, CDR1

<400> SEQUENCE: 64

Ser Ala Ser Ser Ser Val Ser Tyr Met His
1               5                   10

<210> SEQ ID NO 65
<211> LENGTH: 7
<212> TYPE: PRT
<213> ORGANISM: Artificial Sequence
<220> FEATURE:
<223> OTHER INFORMATION: CD19-binding domain VL CDR, CDR2

<400> SEQUENCE: 65

Asp Thr Ser Lys Leu Ala Ser
1               5

<210> SEQ ID NO 66
<211> LENGTH: 9
<212> TYPE: PRT
<213> ORGANISM: Artificial Sequence
<220> FEATURE:
<223> OTHER INFORMATION: CD19-binding domain VL CDR, CDR3
```

```
<400> SEQUENCE: 66

Gln Gln Trp Asn Ile Asn Pro Leu Thr
1               5

<210> SEQ ID NO 67
<211> LENGTH: 119
<212> TYPE: PRT
<213> ORGANISM: Artificial Sequence
<220> FEATURE:
<223> OTHER INFORMATION: VH sequence from murine monoclonal antibody

<400> SEQUENCE: 67

Gln Val Gln Leu Gln Gln Ser Gly Pro Glu Leu Val Lys Pro Gly Ala
1               5                   10                  15

Ser Val Lys Ile Ser Cys Lys Ala Ser Gly Tyr Ala Phe Ser Ser Ser
            20                  25                  30

Trp Met Asn Trp Val Lys Gln Arg Pro Gly Lys Gly Leu Glu Trp Ile
        35                  40                  45

Gly Arg Ile Tyr Pro Gly Asp Glu Asp Thr Asn Tyr Ser Gly Lys Phe
    50                  55                  60

Lys Asp Lys Ala Thr Leu Thr Ala Asp Lys Ser Ser Thr Thr Ala Tyr
65                  70                  75                  80

Met Gln Leu Ser Ser Leu Thr Ser Glu Asp Ser Ala Val Tyr Phe Cys
                85                  90                  95

Ala Arg Ser Leu Leu Tyr Gly Asp Tyr Leu Asp Tyr Trp Gly Gln Gly
            100                 105                 110

Thr Thr Leu Thr Val Ser Ser
        115

<210> SEQ ID NO 68
<211> LENGTH: 8
<212> TYPE: PRT
<213> ORGANISM: Artificial Sequence
<220> FEATURE:
<223> OTHER INFORMATION: VH CDR1

<400> SEQUENCE: 68

Gly Phe Thr Phe Ser Asp Ser Tyr
1               5

<210> SEQ ID NO 69
<211> LENGTH: 8
<212> TYPE: PRT
<213> ORGANISM: Artificial Sequence
<220> FEATURE:
<223> OTHER INFORMATION: VH CDR2

<400> SEQUENCE: 69

Ile Tyr Ala Gly Asp Gly Ala Thr
1               5

<210> SEQ ID NO 70
<211> LENGTH: 17
<212> TYPE: PRT
<213> ORGANISM: Artificial Sequence
<220> FEATURE:
<223> OTHER INFORMATION: VH CDR3

<400> SEQUENCE: 70

Ala Arg Pro Leu Tyr Thr Thr Ala Tyr Tyr Val Gly Gly Phe Ala
1               5                   10                  15

Tyr
```

<210> SEQ ID NO 71
<211> LENGTH: 12
<212> TYPE: PRT
<213> ORGANISM: Artificial Sequence
<220> FEATURE:
<223> OTHER INFORMATION: VL CDR1

<400> SEQUENCE: 71

Gln Ser Leu Leu Ser Ser Gly Asn Gln Lys Asn Tyr
1               5                   10

<210> SEQ ID NO 72
<211> LENGTH: 3
<212> TYPE: PRT
<213> ORGANISM: Artificial Sequence
<220> FEATURE:
<223> OTHER INFORMATION: VL CDR2

<400> SEQUENCE: 72

Trp Ala Ser
1

<210> SEQ ID NO 73
<211> LENGTH: 9
<212> TYPE: PRT
<213> ORGANISM: Artificial Sequence
<220> FEATURE:
<223> OTHER INFORMATION: VL CDR3

<400> SEQUENCE: 73

Gln Gln Tyr Tyr Asp Thr Pro Leu Thr
1               5

<210> SEQ ID NO 74
<211> LENGTH: 6
<212> TYPE: PRT
<213> ORGANISM: Artificial Sequence
<220> FEATURE:
<223> OTHER INFORMATION: DXL motif of TACI cysteine-rich domain (CRD)
<220> FEATURE:
<221> NAME/KEY: MISC_FEATURE
<222> LOCATION: (1)..(1)
<223> OTHER INFORMATION: Xaa may be Phe, Tyr or Trp
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: MISC_FEATURE
<222> LOCATION: (5)..(5)
<223> OTHER INFORMATION: Xaa may be Val or Thr
<220> FEATURE:
<221> NAME/KEY: MISC_FEATURE
<222> LOCATION: (6)..(6)
<223> OTHER INFORMATION: Xaa may be Arg or Gly

<400> SEQUENCE: 74

Xaa Asp Xaa Leu Xaa Xaa
1               5

<210> SEQ ID NO 75
<211> LENGTH: 107
<212> TYPE: PRT
<213> ORGANISM: Artificial Sequence
<220> FEATURE:
<223> OTHER INFORMATION: VL sequence from murine monoclonal antibody

<400> SEQUENCE: 75

```
Gln Ile Val Leu Thr Gln Ser Pro Ala Ile Met Ser Ala Ser Pro Gly
  1               5                  10                  15

Glu Lys Val Thr Met Thr Cys Ser Ala Ser Ser Val Ser Tyr Met
             20                  25                  30

His Trp Tyr Gln Gln Lys Ser Gly Thr Ser Pro Lys Arg Trp Ile Tyr
         35                  40                  45

Asp Thr Ser Lys Leu Ala Ser Gly Val Pro Asp Arg Phe Ser Gly Ser
     50                  55                  60

Gly Ser Gly Thr Ser Tyr Phe Leu Thr Ile Asn Met Glu Ala Glu
 65                  70                  75                  80

Asp Ala Ala Thr Tyr Tyr Cys Gln Gln Trp Asn Ile Asn Pro Leu Thr
                 85                  90                  95

Phe Gly Ala Gly Thr Lys Leu Glu Leu Lys Arg
             100                 105
```

<210> SEQ ID NO 76
<211> LENGTH: 241
<212> TYPE: PRT
<213> ORGANISM: Artificial Sequence
<220> FEATURE:
<223> OTHER INFORMATION: VH-VL scFv sequence from murine monoclonal
      antibody

<400> SEQUENCE: 76

```
Gln Val Gln Leu Gln Gln Ser Gly Pro Glu Leu Val Lys Pro Gly Ala
  1               5                  10                  15

Ser Val Lys Ile Ser Cys Lys Ala Ser Gly Tyr Ala Phe Ser Ser Ser
             20                  25                  30

Trp Met Asn Trp Val Lys Gln Arg Pro Gly Lys Gly Leu Glu Trp Ile
         35                  40                  45

Gly Arg Ile Tyr Pro Gly Asp Glu Asp Thr Asn Tyr Ser Gly Lys Phe
     50                  55                  60

Lys Asp Lys Ala Thr Leu Thr Ala Asp Lys Ser Ser Thr Thr Ala Tyr
 65                  70                  75                  80

Met Gln Leu Ser Ser Leu Thr Ser Glu Asp Ser Ala Val Tyr Phe Cys
                 85                  90                  95

Ala Arg Ser Leu Leu Tyr Gly Asp Tyr Leu Asp Tyr Trp Gly Gln Gly
             100                 105                 110

Thr Thr Leu Thr Val Ser Ser Gly Gly Gly Ser Gly Gly Gly Gly
             115                 120                 125

Ser Gly Gly Gly Gly Ser Gln Ile Val Leu Thr Gln Ser Pro Ala Ile
 130                 135                 140

Met Ser Ala Ser Pro Gly Glu Lys Val Thr Met Thr Cys Ser Ala Ser
145                 150                 155                 160

Ser Ser Val Ser Tyr Met His Trp Tyr Gln Gln Lys Ser Gly Thr Ser
                 165                 170                 175

Pro Lys Arg Trp Ile Tyr Asp Thr Ser Lys Leu Ala Ser Gly Val Pro
             180                 185                 190

Asp Arg Phe Ser Gly Ser Gly Ser Gly Thr Ser Tyr Phe Leu Thr Ile
         195                 200                 205

Asn Asn Met Glu Ala Glu Asp Ala Ala Thr Tyr Tyr Cys Gln Gln Trp
     210                 215                 220

Asn Ile Asn Pro Leu Thr Phe Gly Ala Gly Thr Lys Leu Glu Leu Lys
225                 230                 235                 240

Arg
```

<210> SEQ ID NO 77
<211> LENGTH: 20
<212> TYPE: PRT
<213> ORGANISM: Artificial Sequence
<220> FEATURE:
<223> OTHER INFORMATION: cleavage site, 2A-like sequence

<400> SEQUENCE: 77

Arg Ala Glu Gly Arg Gly Ser Leu Leu Thr Cys Gly Asp Val Glu Glu
1               5                   10                  15

Asn Pro Gly Pro
            20

<210> SEQ ID NO 78
<211> LENGTH: 5
<212> TYPE: PRT
<213> ORGANISM: Artificial Sequence
<220> FEATURE:
<223> OTHER INFORMATION: glycine-serine linker

<400> SEQUENCE: 78

Gly Gly Gly Gly Ser
1               5

<210> SEQ ID NO 79
<211> LENGTH: 8
<212> TYPE: PRT
<213> ORGANISM: Artificial Sequence
<220> FEATURE:
<223> OTHER INFORMATION: VH CDR1

<400> SEQUENCE: 79

Gly Phe Ile Phe Ser Asp Tyr Asn
1               5

<210> SEQ ID NO 80
<211> LENGTH: 8
<212> TYPE: PRT
<213> ORGANISM: Artificial Sequence
<220> FEATURE:
<223> OTHER INFORMATION: VH CDR2

<400> SEQUENCE: 80

Ile Ile Tyr Asp Gly Ser Ser Thr
1               5

<210> SEQ ID NO 81
<211> LENGTH: 9
<212> TYPE: PRT
<213> ORGANISM: Artificial Sequence
<220> FEATURE:
<223> OTHER INFORMATION: VH CDR3

<400> SEQUENCE: 81

Ala Thr Arg Pro Gly Pro Phe Ala Tyr
1               5

<210> SEQ ID NO 82
<211> LENGTH: 11
<212> TYPE: PRT
<213> ORGANISM: Artificial Sequence
<220> FEATURE:
<223> OTHER INFORMATION: VL CDR1

<400> SEQUENCE: 82

Gln Ser Leu Leu His Ser Asn Gly Asn Thr Tyr

```
1               5                    10

<210> SEQ ID NO 83
<211> LENGTH: 3
<212> TYPE: PRT
<213> ORGANISM: Artificial Sequence
<220> FEATURE:
<223> OTHER INFORMATION: VL CDR2

<400> SEQUENCE: 83

Leu Val Ser
1

<210> SEQ ID NO 84
<211> LENGTH: 8
<212> TYPE: PRT
<213> ORGANISM: Artificial Sequence
<220> FEATURE:
<223> OTHER INFORMATION: VL CDR3

<400> SEQUENCE: 84

Val His Gly Thr His Ala Trp Thr
1               5

<210> SEQ ID NO 85
<211> LENGTH: 6
<212> TYPE: PRT
<213> ORGANISM: Artificial Sequence
<220> FEATURE:
<223> OTHER INFORMATION: MMP-1, sequence cleavable with MMP enzyme

<400> SEQUENCE: 85

Pro Leu Gly Leu Trp Ala
1               5

<210> SEQ ID NO 86
<211> LENGTH: 6
<212> TYPE: PRT
<213> ORGANISM: Artificial Sequence
<220> FEATURE:
<223> OTHER INFORMATION: MMP-2, sequence cleavable with MMP enzyme

<400> SEQUENCE: 86

Pro Ala Gly Leu Ala Gly
1               5

<210> SEQ ID NO 87
<211> LENGTH: 6
<212> TYPE: PRT
<213> ORGANISM: Artificial Sequence
<220> FEATURE:
<223> OTHER INFORMATION: MMP-9, sequence cleavable with MMP enzyme

<400> SEQUENCE: 87

Pro Leu Gly Leu Ala Gly
1               5

<210> SEQ ID NO 88
<211> LENGTH: 6
<212> TYPE: PRT
<213> ORGANISM: Artificial Sequence
```

```
<220> FEATURE:
<223> OTHER INFORMATION: scrambled MMP-9 cleavable linker (negative
      control)

<400> SEQUENCE: 88

Leu Ala Leu Gly Pro Gly
1               5
```

CHIMERIC ANTIGEN RECEPTOR

CROSS-REFERENCE TO RELATED APPLICATIONS

This is a U.S. National Phase of International Application No. PCT/GB2019/052726, filed Sep. 26, 2019, which claims priority to Great Britain Application No. 1815775.0 filed Sep. 27, 2018 and Great Britain Application No. 1902021.3, filed Feb. 14, 2019.

FIELD OF THE INVENTION

The present invention relates to chimeric antigen receptor (CAR) which binds to a low density target antigen such as B cell maturation antigen (BCMA).

BACKGROUND TO THE INVENTION

Multiple Myeloma

Multiple Myeloma (myeloma) is a bone-marrow malignancy of plasma cells. Collections of abnormal plasma cells accumulate in the bone marrow, where they interfere with the production of normal blood cells. Myeloma is the second most common hematological malignancy in the U.S. (after non-Hodgkin lymphoma), and constitutes 13% of haematologic malignancies and 1% of all cancers. The disease is burdensome in terms of suffering as well as medical expenditure since it causes pathological fractures, susceptibility to infection, renal and then bone-marrow failure before death.

Unlike many lymphomas, myeloma is currently incurable. Standard chemotherapy agents used in lymphoma are largely ineffective for myeloma. In addition, since CD20 expression is lost in plasma cells, Rituximab cannot be used against this disease. New agents such as Bortezamib and Lenolidomide are partially effective, but fail to lead to long-lasting remissions.

There is thus a need for alternative agents for the treatment of myeloma which have increased efficacy and improved long-term effects.

Chimeric Antigen Receptors (CARs)

Chimeric antigen receptors are proteins which, in their usual format, graft the specificity of a monoclonal antibody (mAb) to the effector function of a T-cell. Their usual form is that of a type I transmembrane domain protein with an antigen recognizing amino terminus, a spacer, a transmembrane domain all connected to a compound endodomain which transmits T-cell survival and activation signals.

The most common form of these molecules use single-chain variable fragments (scFv) derived from monoclonal antibodies to recognize a target antigen. The scFv is fused via a spacer and a transmembrane domain to a signaling endodomain. Such molecules result in activation of the T-cell in response to recognition by the scFv of its target. When T cells express such a CAR, they recognize and kill target cells that express the target antigen. Several CARs have been developed against tumour associated antigens, and adoptive transfer approaches using such CAR-expressing T cells are currently in clinical trial for the treatment of various cancers. Carpenter et al (2013, Clin Cancer Res 19(8) 2048-60) describe a CAR which incorporates a scFv against the B-cell maturation antigen (BCMA).

BCMA is a transmembrane protein that is preferentially expressed in mature lymphocytes, i.e. memory B cells, plasmablasts and bone marrow plasma cells. BCMA is also expressed on multiple myeloma cells.

Carpenter et al demonstrate that T cells transduced to express the anti-BCMA CAR are capable of specifically killing myeloma cells from a plasmacytoma of a myeloma patient.

Although CAR approaches using anti-BCMA antibodies show promise, a particular consideration when targeting this antigen is the particularly low density of BCMA on myeloma cells, in comparison for instance with CD19 on a lymphoma cell. Although CAR-T cell-mediated treatment have shown success in the clinic towards abundant target antigens such as CD19 or GD2, chimeric antigen receptors have been reported to fail to signal in response to very low-density antigens.

For example, a CAR-T study targeting anaplastic lymphoma kinase (ALK), showed that the CAR-T cells had limited anti-tumor efficacy in two xenograft models of human neuroblastoma. It was shown that cytokine production was highly dependent upon ALK target density and that target density of ALK on neuroblastoma cell lines was insufficient for maximal activation of CAR T cells (Walker et al. (2017) Mol. Ther. 25, 2189-2201).

Another study involved the use of anti-CD22 CAR-T cell in the treatment of relapsed and/or refractory pre-B cell acute lymphoblastic leukemia (B-ALL), although dose-dependent antileukemic activity was observed, some relapses were observed. Relapses were associated with diminished CD22 site density that were thought to permitted CD22+ cell escape from killing by CD22-CAR T cells (Fry et al. (2017) Nat. Med. doi:10.1038/nm.4441).

There is a hierarchy of CAR T-cell activation from killing, to cytokine release to proliferation. A CAR T-cell may kill a target cell with low density antigen but fail to fully activate.

There is therefore a need for alternative CAR T-cell approaches, capable of killing target cells expressing a low density of target antigen.

DESCRIPTION OF THE FIGURES

CAR expressing cells were co-cultured with non BCMA-expressing (FIG. 7A) or low BCMA-expressing (FIG. 7B) target cells at a 1:4 or 1:8 ratio. A previously characterised anti-BCMA CAR, bb2121, was used as a positive control. After 24 hours IFNγ production was assayed by ELISA FIG. 8: CD4 and CD8 cells counts of T-cells expressing an anti-BCMA CAR in either an scFv or FabCAR format following co-culture with target cells.

CAR expressing cells were co-cultured with non BCMA-expressing (SupT1 NT), low BCMA-expressing (SupT1BCMAlow), very low BCMA-expressing (JeKo-1) or MM.1s target cells at a 1:1 ratio for 96 hours. Whole cell counts for CD4 (FIG. 8A) and CD8 (FIG. 8B) T cells were obtained by gating on CD3 and the marker RQR8, then either CD8+ or CD8−.

Figure 9:
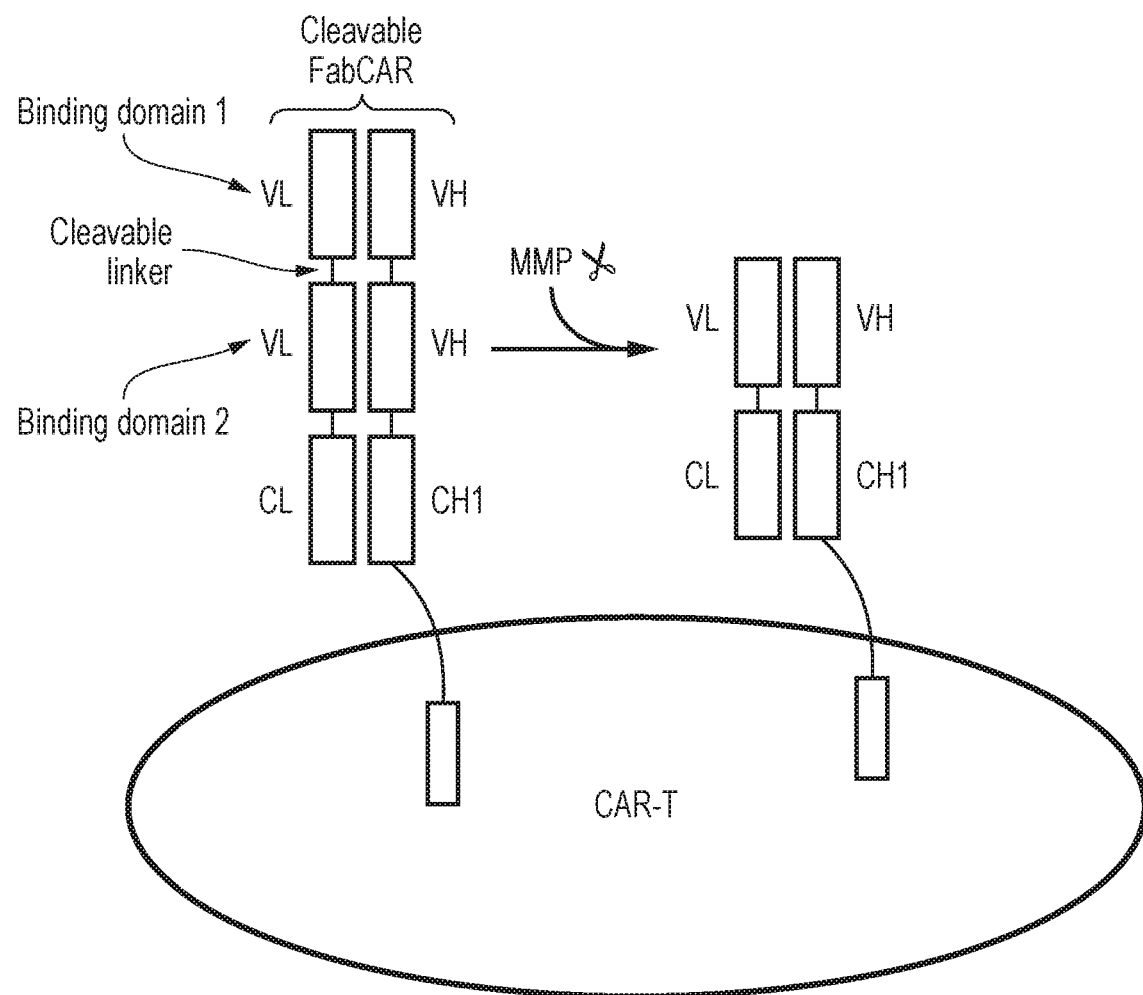

FIG. 9: Schematic diagram illustrating a cleavable FabCAR

A cleavable FabCAR comprises two antigen binding domains: an external (membrane-distal) binding domain 1 and an internal (membrane-proximal) binding domain 2. Binding domains 1 and 2 are joined by a cleavable linker. Cleavage of the linker by, for example, a matrix metalloproteinase (MMP) removes binding domain 1. In the absence of cleavage, when the FabCAR is intact, the internal binding domain is partially occluded by the presence of the external domain due to steric hindrance. The internal domain is activated upon cleavage of the heavy and light chain.

Figure 10:
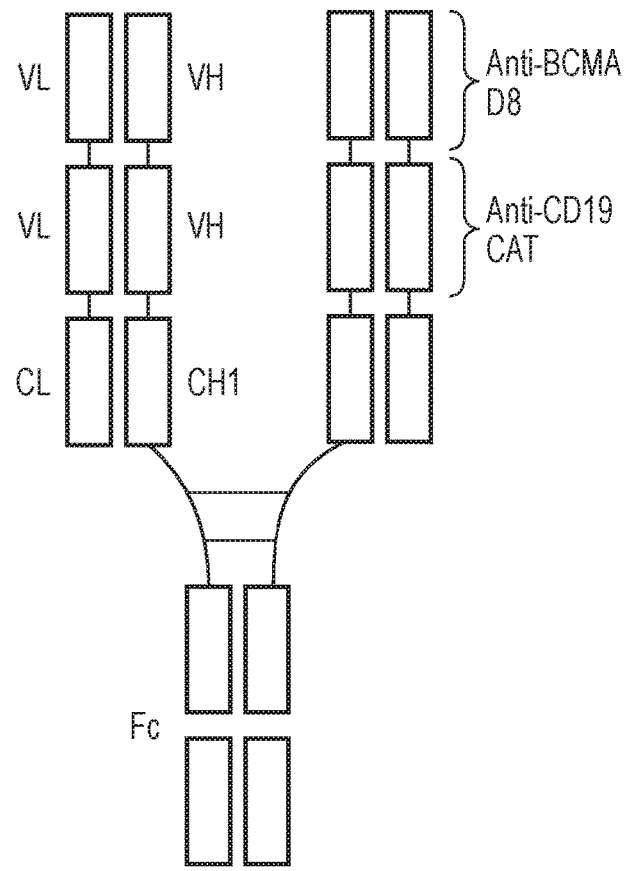

FIG. 10: Schematic diagram illustrating the soluble antibody described in Example 7

A soluble antibody was designed with two variable domains, and external binding domain against BCMA (Anti-BCMA D8) and an internal binding domain against CD19 (Anti-CD19 CAT). An MMP-9 cleavable linker was included between the VH domains on one chain and the VL domains on the other chain. The VH-containing chain also comprised the Fc portion of an antibody.

Figure 11:
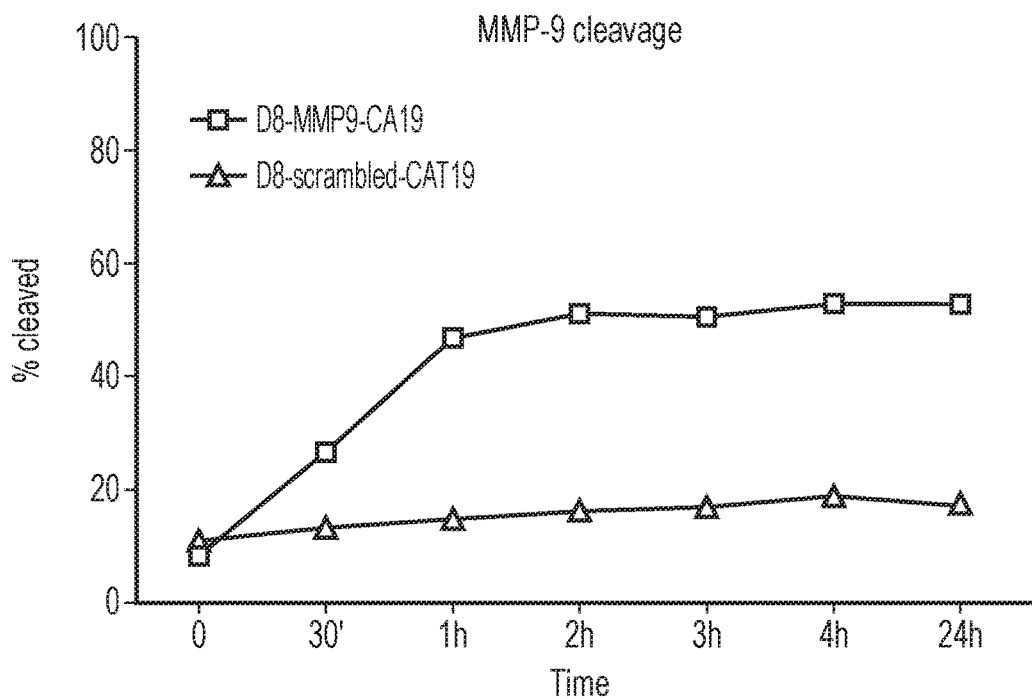

FIG. 11: Graph to show percentage cleavage of the soluble antibody (D8-MMP9-CAT19) over time following incubation in the presence of MMP-9. An equivalent antibody with a scrambled linker which doesn't comprise an MMP-9 cleavage site (D8-scrambled-CAT19) was used as a negative control.

Figure 12:
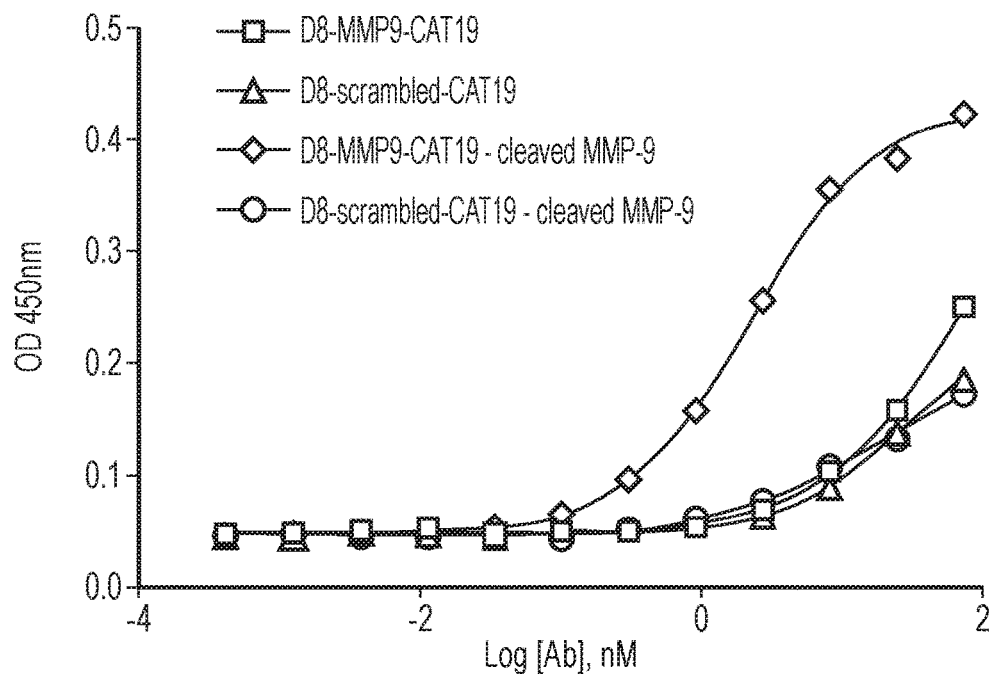

FIG. 12: Graph to show CD19 binding by ELISA by the soluble antibody (D8-MMP9-CAT19) or a negative control having a scrambled linker (D8-scrambled-CAT19) either left untreated or following treatment with MMP-9

Figure 13:
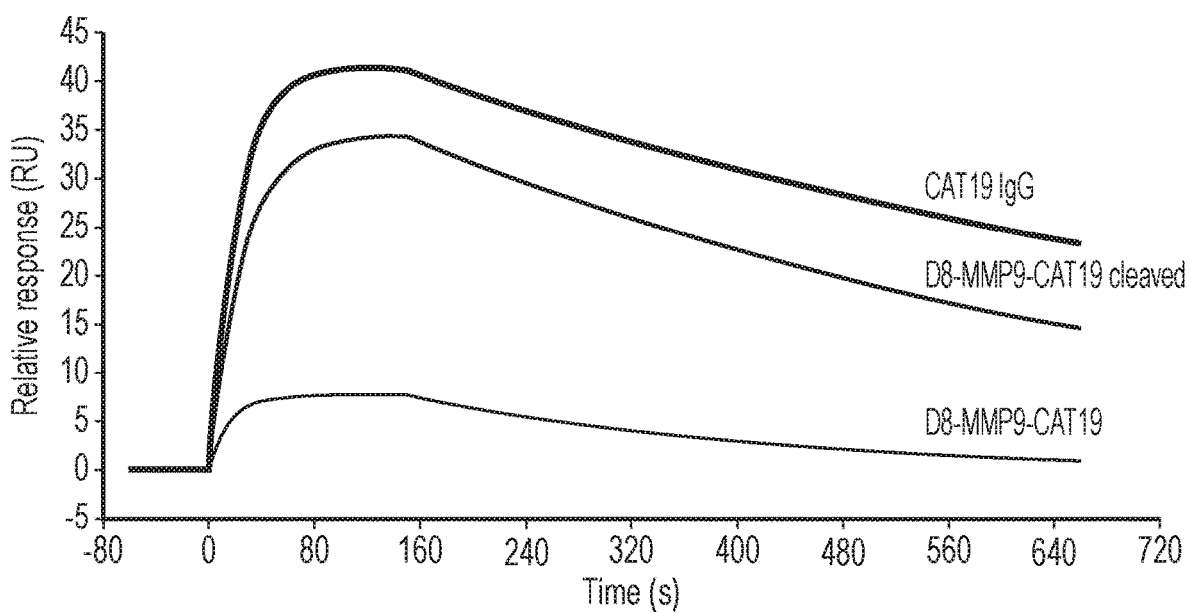

FIG. 13: Graph to show binding kinetics of the soluble antibody on CD19 either left untreated (D8-MMP9-CAT19) or following treatment with MMP-9 (D8-MMP9-CAT19 cleaved). A CD-19 monoclonal antibody (CAT19 IgG) was used as a positive control.

SUMMARY OF ASPECTS OF THE INVENTION

The present inventors have found that, for a CAR-T cell targeting a low-density target antigen, using a CAR with a Fab antigen binding domain results in more efficient CAR-mediated signalling.

Thus in a first aspect the present invention provides a chimeric antigen receptor (CAR) which binds a low density target antigen, wherein the CAR comprises a Fab antigen binding domain.

The target antigen may be expressed at an average density of fewer than 1500 copies per target cell.

The target antigen may be selected from: ROR1, Tyrp-1, TACI, ALK and BCMA. For example, the target antigen may be BCMA.

In an alternative embodiment of the first aspect of the invention the Fab antigen-binding domain may comprise a first binding domain which binds a first target antigen and a second binding domain which binds a second target antigen.

The first target antigen or the second target antigen may be BCMA.

In this embodiment, the FabCAR may comprise a cleavable linker between the first and second binding domains.

The linker may be cleavable with an agent such as an enzyme. For example the linker may be cleavable with a matrix metalloproteinase (MMP). The agent may be administered to the subject before or after administration of CAR-expressing cells of the invention in order to cleave off the first binding domain and reveal the second binding domain. Alternatively, cleavage may happen naturally at a specific site in the body if the cleavage agent (e.g. enzyme) is expressed at that site. The site may, for example, be a site of inflammation or a tumour site.

In a second aspect the present invention provides a nucleic acid sequence which encodes a CAR according to the first aspect of the invention.

In a third aspect, the present invention provides a nucleic acid construct which encodes a CAR according to the first aspect of the invention and has one of the following general structures:

VH-CH-spacer-TM-endo-coexpr-VL-CL;
VL-CL-coexpr-VH-CH-spacer-TM-endo;
VL-CL-spacer-TM-endo-coexpr-VH-CH; or
VH-CH-coexpr-VL-CL-spacer-TM-endo;

in which:

VH is a nucleic acid sequence encoding a heavy chain variable region;

CH is a nucleic acid sequence encoding a heavy chain constant region spacer is a nucleic acid encoding a spacer;

TM is a nucleic acid sequence encoding a transmembrane domain;

endo is a nucleic acid sequence encoding an endodomain;

coexpr is a nucleic acid sequence enabling co-expression of the first and second polypeptides;

VL is a nucleic acid sequence encoding a light chain variable region; and

CL is a nucleic acid sequence encoding a light chain constant region.

In an alternative embodiment of the third aspect of the invention the nucleic acid construct may have one of the following general structures:

VH1-L1-VH2-CH-spacer-TM-endo-coexpr-VL1-L2-VL2-CL;

VL1-L1-VL2-CL-coexpr-VH1-L2-VH2-CH-spacer-TM-endo;

VL1-L1-VL2-CL-spacer-TM-endo-coexpr-VH1-L2-VH2-CH; or

VH1-L1-VH2-CH-coexpr-VL1-L2-VL2-CL-spacer-TM-endo;

in which:

VH1 is a nucleic acid sequence encoding a heavy chain variable region of the first binding domain;

L1 and L2, which may be the same or different, are cleavable linkers;

VH2 is a nucleic acid sequence encoding a heavy chain variable region of the second binding domain;

CH is a nucleic acid sequence encoding a heavy chain constant region;

spacer is a nucleic acid encoding a spacer;

TM is a nucleic acid sequence encoding a transmembrane domain;

endo is a nucleic acid sequence encoding an endodomain;

coexpr is a nucleic acid sequence enabling co-expression of the first and second polypeptides;

VL1 is a nucleic acid sequence encoding a light chain variable region of the first binding domain;

VL2 is a nucleic acid sequence encoding a light chain variable region of the second binding domain; and CL is a nucleic acid sequence encoding a light chain constant region.

The nucleic acid construct may also encode a second chimeric antigen receptor having a domain antibody (dAb), scFv or Fab antigen binding domain.

The second chimeric antigen receptor may bind one of the following antigens: CD19, FcRL5 and TACI.

In a fourth aspect, the present invention provides a vector which comprises a nucleic acid sequence according to the second aspect of the invention or a nucleic acid construct according to the third aspect of the invention.

In a fifth aspect, the present invention provides a cell which expresses a CAR according to the first aspect of the invention.

The cell may express a first CAR according to the first aspect of the invention, and a second chimeric antigen receptor as defined above.

The cell may also express a constitutively active cytokine receptor.

In a sixth aspect, the present invention provides a method for making a cell according to the fifth aspect of the invention, which comprises the step of introducing a nucleic acid sequence according to the second aspect of the invention; a nucleic acid construct according to the third aspect of the invention; or a vector according to the fourth aspect of the invention into a cell ex vivo.

In a seventh aspect, the present invention provides a pharmaceutical composition which comprises a plurality of cells according to the fifth aspect of the invention, together with a pharmaceutically acceptable carrier, diluent or excipient.

In an eighth aspect, the present invention provides a method for treating cancer which comprises the step of administering a pharmaceutical composition according to claim the seventh aspect of the invention to a subject.

The cancer may be multiple myeloma.

In a ninth aspect, the present invention provides a pharmaceutical composition according to the seventh aspect of the invention for use in treating cancer.

In a tenth aspect, the present invention provides the use of a cell according to the fifth aspect of the invention in the manufacture of a pharmaceutical composition for treating cancer.

Figure 3:
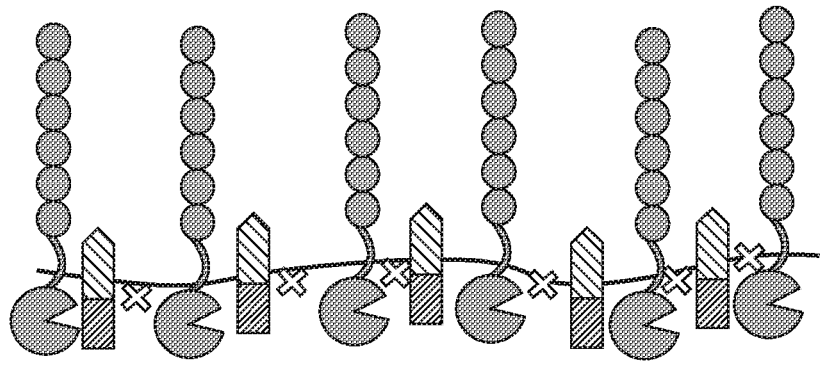
FIG. 3: Schematic diagram illustrating the interaction between a classical CAR-T cell with a target cell expressing a target antigen at low density. (a) The CAR T-cell membrane in its ground state; (b) The CAR T-cell membrane forms an immune synapse with a high-density target expressing cell; (c) The CAR T-cell membrane in response to a target cell with low-density antigen.
Figure 3:
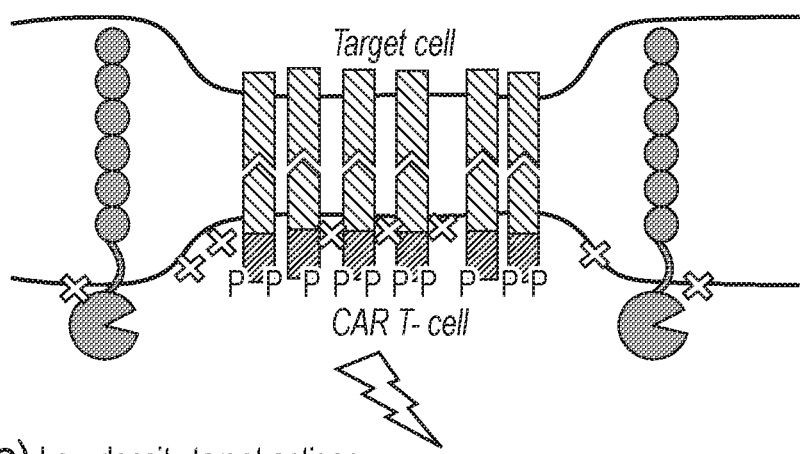
Figure 3:
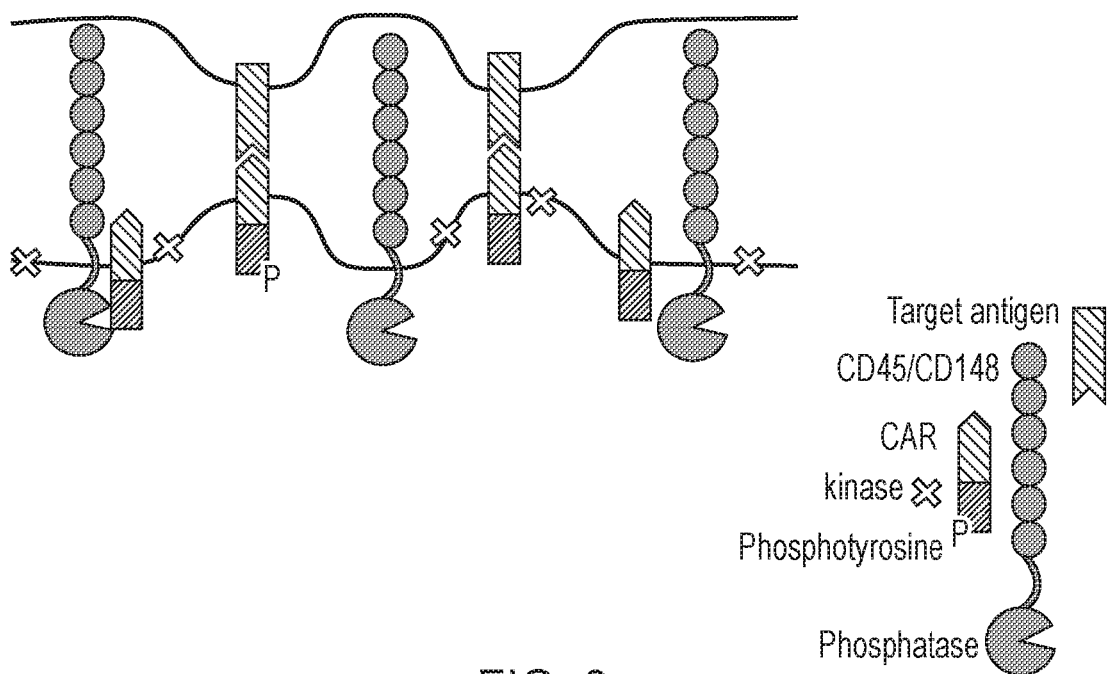

The present invention provides chimeric antigen receptors which show improved CAR-mediated signalling and target cell killing when targeting antigens expressed at low density on the target cell. Such antigens are difficult to target with a classical CAR as they form sub-optimal T-cell:target cell synapses (FIG. 3).

To capacity to target such antigens opens up whole new possibilities for cancer treatment. Many potentially useful cancer target antigens are expressed at a low density on the target cell, such as ROR1, Tyrp-1, TACI, ALK and BCMA. The present invention provides improved constructs for targeting these antigens, enabling them to be used as single targets and, importantly, to be included in strategies for targeting multiple antigens in order to increase CAR-T cell efficacy and safety.

Further Aspects

The present invention also provides the aspects summarised in the following numbered paragraphs.

1. A chimeric antigen receptor (CAR) which comprises a Fab antigen-binding domain comprising a first binding domain which binds a first target antigen and a second binding domain which binds a second target antigen.

2. A CAR according to paragraph 1, which comprises a cleavable linker between the first and second binding domains.

3. A CAR according to paragraph 2, wherein the linker is cleavable with a matrix metalloproteinase (MMP).

4. A CAR according to any preceding paragraph, wherein the first target antigen is expressed at a tumour site, so when a cell expressing the CAR is administered to a cancer patient it homes to a tumour site within the subject.

5. A CAR according to any preceding paragraph, wherein the second target antigen is expressed at a tumour site and also on one or more normal tissues.

6. A CAR according to any preceding paragraph, wherein the first and/or second target antigen is selected from the following group: BCMA, ROR1, Tyrp-1, TACI, ALK, ErbB2, MUC1, CD33, CD123, PSMA, EpCAM, GD2, NCAM, Folate binding protein and MUC16.

7. A CAR according to any of paragraphs 1 to 5, wherein the first target antigen/second target antigen are selected from one of the following antigen pairs: ErbB2 and MUC1; CD33 and CD123; PSMA and EpCAM; GD2 and NCAM; Folate binding protein and MUC16.

8. A CAR according to paragraph 7, wherein the first target antigen/second target antigen are one of the target antigen pairs shown in Table 2.

9. A nucleic acid sequence which encodes a CAR according to any preceding paragraph.

10. A nucleic acid construct which encodes a CAR according to any of paragraphs 1 to 8 and has one of the following general structures:

VH1-L1-VH2-CH-spacer-TM-endo-coexpr-VL1-L2-VL2-CL;

VL1-L1-VL2-CL-coexpr-VH1-L2-VH2-CH-spacer-TM-endo;

VL1-L1-VL2-CL-spacer-TM-endo-coexpr-VH1-L2-VH2-CH; or

VH1-L1-VH2-CH-coexpr-VL1-L2-VL2-CL-spacer-TM-endo in which:
- VH1 is a nucleic acid sequence encoding a heavy chain variable region of the first binding domain;
- L1 and L2, which may be the same or different, are cleavable linkers;
- VH2 is a nucleic acid sequence encoding a heavy chain variable region of the second binding domain;
- CH is a nucleic acid sequence encoding a heavy chain constant region spacer is a nucleic acid encoding a spacer;
- TM is a nucleic acid sequence encoding a transmembrane domain;
- endo is a nucleic acid sequence encoding an endodomain;
- coexpr is a nucleic acid sequence enabling co-expression of the first and second polypeptides;
- VL1 is a nucleic acid sequence encoding a light chain variable region of the first binding domain;
- VL2 is a nucleic acid sequence encoding a light chain variable region of the second binding domain; and
- CL is a nucleic acid sequence encoding a light chain constant region.

11. A vector which comprises a nucleic acid sequence according to paragraph 9 or a nucleic acid construct according to paragraph 10.

12. A cell which expresses a CAR according to any of paragraphs 1 to 8.

13. A method for making a cell according to paragraph 12, which comprises the step of introducing a nucleic acid sequence according to paragraph 9; a nucleic acid construct according to paragraph 10; or a vector according to paragraph 11 into a cell ex vivo.

14. A pharmaceutical composition which comprises a plurality of cells according to paragraph 12, together with a pharmaceutically acceptable carrier, diluent or excipient.

15. A method for treating cancer which comprises the step of administering a pharmaceutical composition according to paragraph 14 to a subject.

16. A pharmaceutical composition according to paragraph 14 for use in treating cancer.

17. The use of a cell according to paragraph 12 in the manufacture of a pharmaceutical composition for treating cancer.

DETAILED DESCRIPTION

Chimeric Antigen Receptors

The present invention relates to a chimeric antigen receptor with a Fab antigen-binding domain.

A classical chimeric antigen receptor (CAR) is a chimeric type I trans-membrane protein which connects an extracellular antigen-recognizing domain (binder) to an intracellular signalling domain (endodomain). The binder is typically a single-chain variable fragment (scFv) derived from a monoclonal antibody (mAb), but it can be based on other formats which comprise an antibody-like antigen binding site. A spacer domain is usually necessary to isolate the binder from the membrane and to allow it a suitable orientation. A common spacer domain used is the Fc of IgG1. More compact spacers can suffice e.g. the stalk from CD8α and even just the IgG1 hinge alone, depending on the antigen. A trans-membrane domain anchors the protein in the cell membrane and connects the spacer to the endodomain.

Early CAR designs had endodomains derived from the intracellular parts of either the γ chain of the FcεR1 or CD3ζ. Consequently, these first generation receptors transmitted immunological signal 1, which was sufficient to trigger T-cell killing of cognate target cells but failed to fully activate the T-cell to proliferate and survive. To overcome this limitation, compound endodomains have been constructed: fusion of the intracellular part of a T-cell co-stimulatory molecule to that of CD3ζ results in second generation receptors which can transmit an activating and co-stimulatory signal simultaneously after antigen recognition. The co-stimulatory domain most commonly used is that of CD28. This supplies the most potent co-stimulatory signal—namely immunological signal 2, which triggers T-cell proliferation. Some receptors have also been described which include TNF receptor family endodomains, such as the closely related OX40 and 41BB which transmit survival signals. Even more potent third generation CARs have now been described which have endodomains capable of transmitting activation, proliferation and survival signals.

When the CAR binds the target-antigen, this results in the transmission of an activating signal to the T-cell it is expressed on. Thus the CAR directs the specificity and cytotoxicity of the T cell towards tumour cells expressing the targeted antigen.

CARs typically therefore comprise: (i) an antigen-binding domain; (ii) a spacer; (iii) a transmembrane domain; and (iii) an intracellular domain which comprises or associates with a signalling domain.

A CAR may have the general structure:

Antigen binding domain—spacer domain—transmembrane domain—intracellular signaling domain (endodomain).

Antigen Binding Domain

The antigen binding domain is the portion of the chimeric receptor which recognizes antigen. In a classical CAR, the antigen-binding domain comprises: a single-chain variable fragment (scFv) derived from a monoclonal antibody (see FIG. 2c). CARs have also been produced with domain antibody (dAb) or VHH antigen binding domains (see FIG. 2b).

Figure 2:
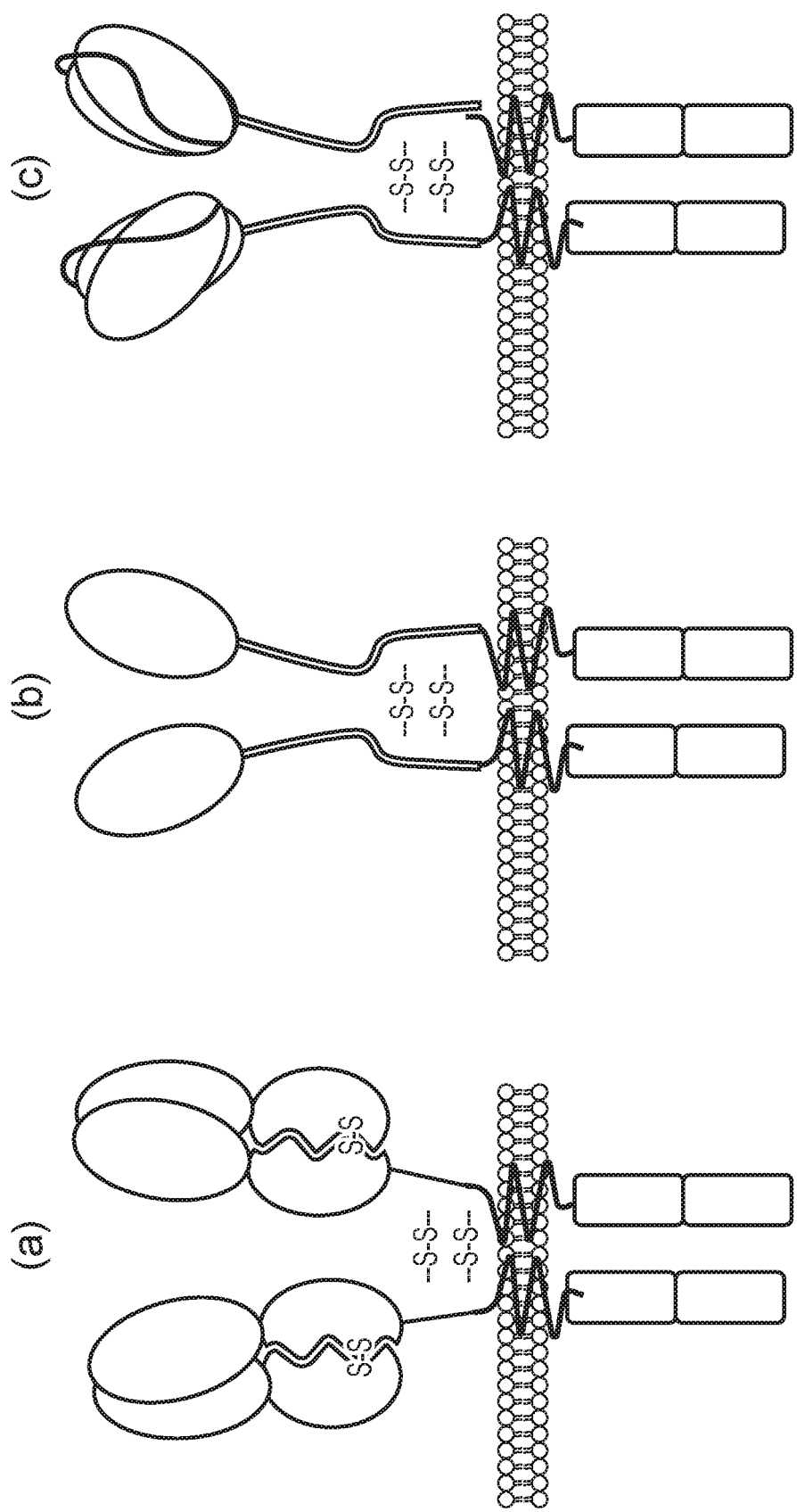
FIG. 2: Different binding domain formats of chimeric antigen receptors (a) Fab CAR format; (b) dAb CAR format; (c) scFv CAR format

In the chimeric antigen receptors of the present invention, the antigen binding comprises a Fab fragment of, for example, a monoclonal antibody (see FIG. 2a). A FabCAR comprises two chains: one having an antibody-like light chain variable region (VL) and constant region (CL); and one having a heavy chain variable region (VH) and constant region (CH). One chain also comprises a transmembrane domain and an intracellular signalling domain. Association between the CL and CH causes assembly of the receptor.

The two chains of a Fab CAR may have the general structure:

VH-CH—spacer—transmembrane domain—intracellular signalling domain; and VL-CL or

VL-CL—spacer-transmembrane domain—intracellular signalling domain; and VH-CH

For the Fab-type chimeric receptors described herein, the antigen binding domain is made up of a VH from one polypeptide chain and a VL from another polypeptide chain.

The polypeptide chains may comprise a linker between the VH/VL domain and the CH/CL domains. The linker may be flexible and serve to spatially separate the VH/VL domain from the CH/CL domain.

Flexible linkers may be composed of small, non-polar residues such as glycine, threonine and serine. The linker may comprise one or more repeats of a glycine-serine linker, such as a (Gly₄Ser)ₙ (SEQ ID No. 78) linker, where n is the number of repeats. The or each linker may be less than 50, 40, 30, 20 or 10 amino acids in length.

The present invention also provides cleavable FabCARs comprising a first binding domain which binds a first target antigen and a second binding domain which binds a second target antigen. Such a cleavable Fab CAR is illustrated schematically in FIG. 9.

A cleavable Fab CAR may comprise a cleavable linker between the first and second binding domains.

The two chains of a cleavable Fab CAR may have the general structure:

VH1-VH2-CH—spacer—transmembrane domain—intracellular signalling domain; and
VL1-VL2-CL
or
VL1-CL1—spacer—transmembrane domain—intracellular signalling domain; and VH2-CH2

In a cleavable FabCAR, there is reduced accessibility to the membrane-proximal binding domain (binding domain 2 in FIG. 9) in the absence of cleavage due to steric hindrance by the first binding domain. Upon cleavage, the removal of binding domain 1 causes increases accessibility to binding domain 2, so it is activated in the presence of its target antigen.

The cleavable linker may be cleaved by an agent, such as a small molecule, or an enzyme such as a protease. The agent may be administered to the patient in order to cleave the linker and activate or enhance signalling via the second binding domain. Alternatively, the cleavage agent may be naturally expressed in vivo, for example at a site of inflammation or tumour growth/metastasis.

Matrix metalloproteinases (MMPs) are a group of enzymes responsible for the degradation of most extracellular matrix proteins during organogenesis and growth. The expression and activity of MMPs in adult tissues is usually low but increases significantly in various pathological conditions including inflammation and cancer.

MMPs are calcium-dependent zinc-containing endopeptidases having a common domain structure. The three common domains are the pro-peptide, the catalytic domain, and the haemopexin-like C-terminal domain, which is linked to the catalytic domain by a flexible hinge region.

MMPs are present in nearly all human cancers; they can be expressed by fibroblasts in the adjacent stroma, cancer-associated fibroblasts, and/or by non-fibroblastic cancer cells. Thus MMPs can influence the tumour environment by promoting angiogenesis, tumour growth, and metastasis. Accordingly, MMP expression is tied to tumour aggressiveness, stage, and patient prognosis.

Increased expression of MMPs is correlated to increased cancer cell proliferation and an increase in tumor size. Nearly every member of the MMP family has been found to be dysregulated in human cancers, with MMP-1, -2, -7, -9, -13, and -14 being the most commonly affected.

In the cleavable FabCAR of the present invention the linker between the first and second binding domains may be cleaved by an MMP, in particular an MMP selected from MMP-1, -2, -7, -9, -13, and -14.

Various sequences are known which are cleavable with MMP enzymes, for example:

```
                              (SEQ ID No. 85)
MMP-1: PLGLWA
```

```
                              (SEQ ID No. 86)
MMP-2: PAGLAG
```

```
                              (SEQ ID No. 87)
MMP-9: PLGLAG
```

The cleavable linker sequence of the cleavable FabCAR of the present invention may comprise one of sequences shown as SEQ ID No. 85 to 87.

Constant Region Domains

There are two types of light chain in humans: kappa (κ) chain and lambda (λ) chain. The lambda class has 4 sub-types: $\lambda_1$, $\lambda_2$, $\lambda_3$ and $\lambda_4$. The light chain constant region of a Fab-type chimeric receptor may be derived from any of these light chain types.

The light chain constant domain of a chimeric receptor of the present invention may have the sequence shown as SEQ ID NO. 1 which is a kappa chain constant domain.

```
                                      SEQ ID No. 1
TVAAPSVFIFPPSDEQLKSGTASVVCLLNNFYPREAKVQWKVDNALQSGN

SQESVTEQDSKDSTYSLSSTLTLSKADYEKHKVYACEVTHQGLSSPVTKS

FNRGEC
```

There are five types of mammalian immunoglobulin heavy chain: γ, δ, α, μ and ε which define the classes of immunoglobulin IgG, IgD, IgA, IgM and IgE respectively. Heavy chains γ, δ and α have a constant domain composed of three tandem Ig domain and have a hinge for added flexibility. Heavy chains μ and ε are composed of four domains.

The CH domain of a Fab-type chimeric receptor of the present invention may comprise the sequence shown as SEQ ID No. 2 which is from a γ immunoglobulin heavy chain.

```
                                      SEQ ID No. 2
STKGPSVFPLAPSSKSTSGGTAALGCLVKDYFPEPVTVSWNSGALTSGVH

TFPAVLQSSGLYSLSSVVTVPSSSLGTQTYICNVNHKPSNTKVDKRV
```

Spacer

Classical CARs comprise a spacer sequence to connect the antigen-binding domain with the transmembrane domain and spatially separate the antigen-binding domain from the endodomain. A flexible spacer allows the antigen-binding domain to orient in different directions to facilitate binding.

In a FabCAR (FIG. 2a), as in a classical chimeric antigen receptor (FIG. 2c) and a dAb CAR (FIG. 2b), the spacer may cause two of the polypeptide chains to dimerise. Two of the polypeptide chains may, for example, comprise one or more suitable cysteine residues to form di-sulphide bridge(s). The hinge from IgG1 is suitable in this regard. A spacer based on an IgG1 hinge may have the sequence shown as SEQ ID. No. 3

```
                                      SEQ ID No. 3
        (human IgG1 hinge):
        AEPKSPDKTHTCPPCPKDPK
```

Alternatively, a hinge spacer may have the sequence shown as SEQ ID No. 4

```
                                      SEQ ID No. 4
              (hinge spacer)
              EPKSCDKTHTCPPCP
```

Transmembrane Domain

The transmembrane domain is the portion of the chimeric receptor which spans the membrane. The transmembrane domain may be any protein structure which is thermodynamically stable in a membrane. This is typically an alpha helix comprising of several hydrophobic residues. The transmembrane domain of any transmembrane protein can be used to supply the transmembrane portion of the chimeric receptor. The presence and span of a transmembrane domain of a protein can be determined by those skilled in the art using the TMHMM algorithm (http://www.cbs.dtu.dk/services/TMHMM-2.0/). Alternatively, an artificially designed TM domain may be used.

Endodomain

The endodomain is the signal-transmission portion of the chimeric receptor. It may be part of or associate with the intracellular domain of the chimeric receptor. After antigen recognition, receptors cluster, native CD45 and CD148 are excluded from the synapse and a signal is transmitted to the cell. The most commonly used endodomain component is that of CD3-zeta which contains 3 ITAMs. This transmits an activation signal to the T cell after antigen is bound. CD3-zeta may not provide a fully competent activation signal and additional co-stimulatory signalling may be needed. Co-stimulatory signals promote T-cell proliferation and survival. There are two main types of co-stimulatory signals: those that belong the Ig family (CD28, ICOS) and the TNF family (OX40, 41 BB, CD27, GITR etc). For example, chimeric CD28 and OX40 can be used with CD3-Zeta to transmit a proliferative/survival signal, or all three can be used together.

The endodomain may comprise:

(i) an ITAM-containing endodomain, such as the endodomain from CD3 zeta; and/or (ii) a co-stimulatory domain, such as the endodomain from CD28 or ICOS; and/or (iii) a domain which transmits a survival signal, for example a TNF receptor family endodomain such as OX-40, 4-1 BB, CD27 or GITR.

A number of systems have been described in which the antigen recognition portion is on a separate molecule from the signal transmission portion, such as those described in WO015/150771; WO2016/124930 and WO2016/030691. The chimeric receptor of the present invention may therefore comprise an antigen-binding component comprising an antigen-binding domain and a transmembrane domain; which is capable of interacting with a separate intracellular signalling component comprising a signalling domain. The vector of the invention may express a chimeric receptor signalling system comprising such an antigen-binding component and intracellular signalling component.

The chimeric receptor may comprise a signal peptide so that when it is expressed inside a cell, the nascent protein is directed to the endoplasmic reticulum and subsequently to the cell surface, where it is expressed. The signal peptide may be at the amino terminus of the molecule.

Target Antigen

A 'target antigen' is an entity which is specifically recognised and bound by the antigen-binding domains of a chimeric receptor of the invention.

The target antigen may be an antigen present on a cancer cell, for example a tumour-associated antigen.

The target antigen for the CAR may be expressed at relatively low density on the target cell.

The cells of the present invention may be capable of killing target cells, such as cancer cells, which express a low density of the CAR target antigen. Examples of tumour associated antigens which are known to be expressed at low densities in certain cancers include, but are not limited to, ROR1 in CLL, Typr-1 in melanoma, BCMA, and TACI in myeloma and ALK in Neuroblastoma.

Figure 1:
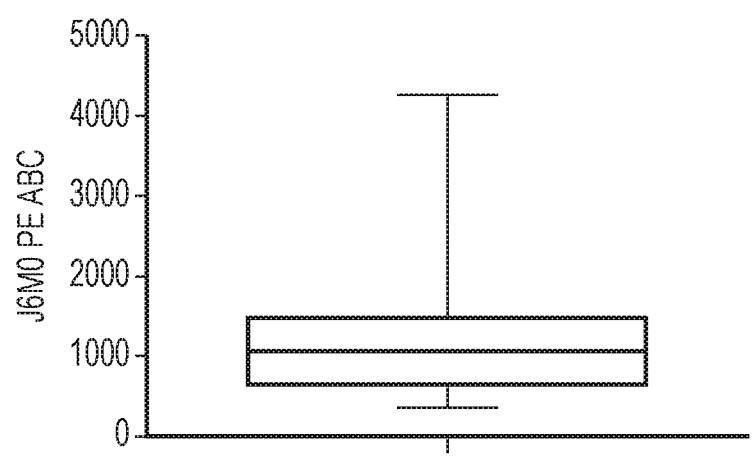
FIG. 1: Expression of BCMA in Multiple Myeloma patients

Example 1 describes a study investigating the expression of BCMA on myeloma cells. It was found that the range of BCMA copy number on a myeloma cell surface is low: at 348.7-4268.4 BCMA copies per cell with a mean of 1181 and a median of 1084.9 (FIG. 1).

The mean copy number of the target antigen for the CAR may be fewer than about 10,000; 5,000; 3,000; 2,000; 1,000; or 500 copies per target cell.

The copy number of an antigen on a cell, such as a cancer cell may be measured using standard techniques, such as using PE Quantibrite beads as described in Example 1.

The target antigen for the CAR may be expressed by the target cell at an average copy number of 1500 copies per cell or fewer, or 1000 copies per cell or fewer.

The target antigen may, for example, be BCMA, ROR1, Tyrp-1, TACI or ALK BCMA

The B cell maturation target, also known as BCMA; TR17_HUMAN, TNFRSF17 (UniProt 002223) is a transmembrane protein that is expressed in mature lymphocytes, e.g., memory B cells, plasmablasts and bone marrow plasma cells. BCMA is also expressed on myeloma cells. BCMA is a non-glycosylated type III transmembrane protein, which is involved in B cell maturation, growth and survival.

An antigen binding domain of a CAR or TanCAR which binds to BCMA may be any domain which is capable of binding BCMA. The VH and VL sequences for fourteen anti-BCMA antibodies are given below with CDR sequences in bold and underlined.

SEQ ID No. 5

(anti-BCMA Ab1 VH)

QIQLVQSGPELVKPGSSVKLSCKTSGFTFSDSYMSWLKQVPGQSIEWIGNIYAGDG

ATHYHQKFKGKATLTVDTSSSTAYMDLSSLTSEDSALYFCARPLYTTAYYYVGGFA

YWGQGTLVTVSS

SEQ ID No. 6

(anti-BCMA Ab1 VL)

DIVMTQSPSSLAVSAGETVTINCKSSQSLLSSGNQKNYLAWYQQKPGQSPKLLIYW

ASTRQSGVPDRFIGSGSGTDFTLTISSVQAEDLAIYYCQQYYDTPLTFGSGTKLEIK

```
                                             SEQ ID No. 7
(anti-BCMA Ab2 VH)
EVKLVESGGG LVQPGRSLKLSCTASGFTFSNYDMAWVRQAPTKGLEWVASISTSG

DTIYYRDSVKGRFTVSRDKAKSTLYLQMDSLRSEDTATYYCARHDYYDGYQSFAY

WGQGTLVTVSS

SEQ ID No. 8
(anti-BCMA Ab2 VL)
NTVMTQSPTSMSISVGDRVIMNCKASQNVGNNIAWYQQKPGQSPKLLIYYASNRYT

GVPDRFTGSGSGTDFILTINSVQAEDAAFYYCQRIYNSALTFGSGTKLEIK

SEQ ID No. 9
(anti-BCMA Ab3 VH)
QVQLQQSGAALVKPGASVKMSCKASGYTFTDYWVSWVKQSHGKSLEWIGEIYPNS

GPTNFNKKFKGKATLTVDKSTSTAYMELSRLTSEDSAIYYCTPRTVAPYNWFAYWG

QGTLVTVSS

SEQ ID No. 10
(anti-BCMA Ab3 VL)
DIVLTQSPALAVSPGERVSISCRASESVSTRMHWYQQKPGQQPKLLIYGASNLESG

VPARFSGSGSGTDFTLTIDPVEADDTATYFCQQSWNDPYTFGAGTKLELK

SEQ ID No. 11
(anti-BCMA Ab4 VH)
EVQLVESGGGLVQPGRSLKLSCSASGFIFSNFDMAWVRQAPRKGLEWVASITTSG

GDTHYRDSVKGRFTVSRHNAKSTLYLQMDSLRSEDTATYYCARHVYYGLFWFFDF

WGPGTMVTVSS

SEQ ID No. 12
(anti-BCMA Ab4 VL)
NTVMTQSPKSIFISVGDRVTVNCKASQNVGTNVDWYQQKTGQSPKLLIYGASNRYT

GVPDRFTGSGSGTDFTFTISNMQAEDLAVYYCMQSNTNPFTFGAGTKLELKR

SEQ ID No. 13
(anti-BCMA Ab5 VH)
EVQLVESGGGLVQPGRSLKLSCTASGFTFSNYDMAWVRQAPTKGLEWVASISTSG

DTIYYRDSVKGRFTVSRDKAKSTLYLQMDSLRSEDTATYYCARHDYYDGYQSFAY

WGQGTLVTVSS

SEQ ID No. 14
(anti-BCMA Ab5 VL)
DIVMTQSPSTLPASLGERVTISCRASQSISNYLNWYQQKPDGTIKPLIYYTSNLQSGV

PSRFSGSGSGTDYSLTISSLEPEDFAMYYCQQDASFPWTFGGGTKLELKR

SEQ ID No. 15
(anti-BCMA Ab6 VH)
EVQLQESGPGLVKPSQSLSLTCSVTGYPITNNYDWSWIRQFPGNKMEWMGYISDS

GNTNYNPSLKSRISITRDTSKNQFFLQLNSVTTEDTATYYCASGYISYIPFAFWGQT

LVTVSS

SEQ ID No. 16
(anti-BCMA Ab6 VL)
DIVLTQSPALAVSLGQRATISCRASQSVSISSYNLMQWYQQKPGQQPKLLIYDASNL

ASGIPARFSGSGSGTDFILTIDPVQADDIATYYCQQSKDDPNTFGAGTKLEIKR

SEQ ID No. 17
(anti-BCMA Ab7 VH)
EVQLQESGPGLVQPSQTLSLTCSVTGYPITNNYDWSWIRKFPGNKMEWMGYISDS

GSTNYNPSLKSRISITRDTSKNQFFLQLNSVTTEDTATYYCASGYISYIPFGFWGQT

LVTVSS
```

```
                                            SEQ ID No. 18
(anti-BCMA Ab7 VL)
DIVLTQSPALAVSPGERVTISCRASESVSTRMHWYQQKPGQQPKLLIYGASNLESG

VPARFSGSGSGTDFTLTIDPVEADDTATYFCQQSWNDPPTFGSGTKLEIK

SEQ ID No. 19
(anti-BCMA Ab8 VH)
EVQLVESGGGLVQPGRSLKLSCTASGFTFSNYDMAWVRQAPTKGLEWVAS**ISTSG

DTIYYRDSVKGRFTVSRDKAKSTLYLQMDSLRSEDTATYYCARHDYYDGYQSFAY**

WGQGTLVTVSS

SEQ ID No. 20
(anti-BCMA Ab8 VL)
DIVMTQSPASQAVSAGEKVIMSCKSSQSLLYSGDQKNYLAWYQQKPGQSPKLLIY**L

ASTRESGVPDRFIGSGSGTDFTLTISSVQAEDLADYYCQQHYSYPLT**FGSGTKLEIK

SEQ ID No. 21
(anti-BCMA Ab9 VH)
EVQLVESGGGLVQPGRSLKLSCAASGFTFSNYDMAWVRQAPTKGLEWVAS**ISTSG

DTIYYRDSVKGRFTVSRDNAKSTLYLQMDSLRSEDTATYYCTRHGYYDGYQSFDY**

WGQGTLVTVSS

SEQ ID No. 22
(anti-BCMA Ab9 VL)
NTVMTQSPKSMSISVGDRVIMNCKASQNVGNNIAWYQQKPGQSPKLLIYYASNRY

TGVPDRFTGGGYGTDFTLTINSVQAEDAATYYCQQWNYPSITFGSGTKLEIK

SEQ ID No. 23
(anti-BCMA Ab10 VH)
EVQLVESGGGLVQPGRSMKLSCAASGFTFSNYDMAWVRQAPTKGLEWVAS**ISPSG

GSTYYRDSVKGRFTVSRDNAKSSLYLQMDSLRSEDTATYYCTRGDYGYNYAYWFA

Y**WGQGTLVTVSS

SEQ ID No. 24
(anti-BCMA Ab10 VL)
DIVMTQAPSSMPASLGERVTISCRASQGISNYLNWYQQKPDGTIKPLIYYTSNLQSG

VPSRFSGSGSGTDYSLTISSLEPEDFAMYCQQYDSSPLTFGAGTKLELK

SEQ ID No. 25
(anti-BCMA Ab11 VH)
EVQLVESGGGLVQPGRSLKLSCEASGFTFSNYDMAWVRQAPTKGLEWVAS**ISTSG

DSIYYRDSVKGRFTVSRDNVKSTLYLQMDSLRSEDTATYYCARHGYYDGYQSFDY**

WGQGTLVTVSS

SEQ ID No. 26
(anti-BCMA Ab12 VL)
DIVMTQSPSSLPASLGERVTISCRASQGISNNLNWYQQKPDGTIKPLIYYTSNLQSGV

PSRFSGSGSGTDYSLTISSLEPEDFATYYCQQDETFPYTFGAGTKLELK

SEQ ID No. 27
(anti-BCMA Ab13 VH)
EVQLVESGGGLVQPGRSLKLSCAASGFTFSNYDMAWVRQAPTKGLEWVAS**ISPSG

GSTYYRDSVKGRFTISRDNAKSTLYLQMDSLRSEDTATYYCATHNYYDGSSLFAY**W

GQGTLVTVSS

SEQ ID No. 28
(anti-BCMA Ab13 VL)
DIVLTQSPALAVSPGERVTISCGANETVSTLVHWYQQKPGQQPKLLIYLASHLESGV

PARFSGSGSGTDFTLTIDPVEADDTATYYCQQSWNDPPTFGGGTKLELK
```

```
                                                       SEQ ID No. 29
(anti-BCMA Ab14 VH)
EVQLVESGGGLVQPGRSLKLSCAASGFIFSDYNMAWVRQAPKKGLEWVATIIYDGS

STNHGDSVKGRFTISRDNAKSTLYLQMDSLRSEDTATYYCATRPGPFAYWGQGTL

VTVS

SEQ ID No. 30
(anti-BCMA Ab15 VL)
DVVLTQTPPTLSATIGQSVSISCRSSQSLLHSNGNTYLHWLLQRPGQSPQFLIYLVS

GLGSGVPNRFSGSGSGTDFTLKISGVEAEDLGIYYCVHGTHAWTVGGGTKLELK
```

The antigen binding domain of a CAR which binds to BCMA may comprise the CDRs from any of anti-BCMA Ab1 to Ab14, as described above.

The antigen binding domain of a CAR which binds to BCMA may comprise the VH and/or VL sequence from any of antiBCMA Ab1 to Ab14, as described above, or a variant thereof which has at least 70, 80, 90 or 90% sequence identity, which variant retains the capacity to bind BCMA.

The present invention also provides new BCMA-binding antibodies, termed Ab1 to Ab14. The VH, VL and CDR sequences of Ab1 to Ab 14 are shown in or as SEQ ID Nos. 5 to 30 above.

BCMA-binding antibody Ab1 shows particularly good efficacy in a CAR format. For example, Ab1 in a scFv CAR format showed improved target cell killing, IL-2 release and proliferation than various equivalent CAR with alternative BCMA binding domains (data not shown).

The present invention also provides the aspects summarised in the following numbered paragraphs.

1. An antigen-binding domain which comprises:
   a) a heavy chain variable region (VH) having complementarity determining regions (CDRs) with the sequences shown in SEQ ID No. 5, 7, 9, 11, 13, 15, 17, 19, 21, 23, 25, 27 or 29; and
   b) a light chain variable region (VL) having complementarity determining regions (CDRs) with the sequences shown in SEQ ID No. 6, 8, 10, 12, 14, 16, 18, 20, 22, 24, 26, 28 or 30.

2. An antigen-binding domain according to paragraph 1 which comprises: a) a heavy chain variable region (VH) having complementarity determining regions (CDRs) with the following sequences:
   CDR1—GFTFSDSY (SEQ ID No. 68)
   CDR2—IYAGDGAT (SEQ ID No. 69)
   CDR3—ARPLYTTAYYYVGGFAY (SEQ ID No. 70); and
   b) a light chain variable region (VL) having complementarity determining regions (CDRs) with the following sequences:

(SEQ ID No. 71)
   CDR1 - QSLLSSGNQKNY (SEQ ID No. 72)
   CDR2 - WAS (SEQ ID No. 73)
   CDR3 - QQYYDTPLT

3. An antigen-binding domain according to paragraph 1 which comprises:
   a) a heavy chain variable region (VH) having complementarity determining regions (CDRs) with the following sequences:

(SEQ ID No. 79)
   CDR1 - GFIFSDYN (SEQ ID No. 80)
   CDR2 - IIYDGSST

CDR3—ATRPGPFAY (SEQ ID No. 81); and
   b) a light chain variable region (VL) having complementarity determining regions (CDRs) with the following sequences:

(SEQ ID No. 82)
   CDR1 - QSLLHSNGNTY (SEQ ID No. 83)
   CDR2 - LVS (SEQ ID No. 84)
   CDR3 - VHGTHAWT

4. An antigen-binding domain according to paragraph 1, which comprises a VH domain having one of the sequences shown as SEQ ID No. 5, 7, 9, 11, 13, 15, 17, 19, 21, 23, 25, 27 or 29; and a VL domain having one of the sequences shown as SEQ ID No. 6, 8, 10, 12, 14, 16, 18, 20, 22, 24, 26, 28 or 30.

5. An antigen-binding domain according to paragraph 3, which comprises a VH domain having the sequence shown as SEQ ID No. 5; and a VL domain having the sequence shown as SEQ ID No. 6.

6. An antigen-binding domain according to paragraph 3, which comprises a VH domain having the sequence shown as SEQ ID No. 29; and a VL domain having the sequence shown as SEQ ID No. 30.

7. An antibody which comprises an antigen-binding domain according to any preceding paragraph.

8. An antibody-drug conjugate (ADC) or bispecific T-cell engager (BiTE) which comprises an antibody according to paragraph 7.

9. A chimeric antigen receptor (CAR) which comprises an antigen-binding domain according to any of paragraphs 1 to 6.

10. A CAR according to paragraph 9, which is a FabCAR.

11. A nucleic acid sequence which encodes an antigen-binding domain according to any of paragraphs 1 to 6, and antibody according to paragraph 6, an ADC or BiTE according to paragraph 8, or a CAR according to paragraph 9 or 10.

12. A vector which comprises a nucleic acid sequence according to paragraph 11.

13. A cell which expresses a CAR according to paragraph 9 or 10.

14. A method for making a cell according to paragraph 13, which comprises the step of introducing a CAR-encoding nucleic acid sequence according to paragraph 11 into a cell.

15. A pharmaceutical composition which comprises a plurality of cells according to paragraph 13, together with a pharmaceutically acceptable carrier, diluent or excipient.

16. A method for treating cancer which comprises the step of administering a pharmaceutical composition according to paragraph 15 to a subject.

17. A method according to paragraph 15, wherein the cancer is a B-cell leukemia or lymphoma.

18. A cell according to paragraph 13 for use in treating a cancer.

19. The use of a cell according to paragraph 13 in the manufacture of a pharmaceutical composition for treating cancer.

General features of, for example, chimeric antigen receptors, nucleic acid sequences and constructs, vectors, cells, pharmaceutical compositions and method of making and using cells described in the preceding and following sections also apply to the corresponding components described in the paragraphs above.

ROR1

Receptor tyrosine kinase-like orphan receptor-1 (ROR1), also known as neurotrophic tyrosine kinase and receptor-related 1 (NTRKR1), is a receptor tyrosine kinase hat modulates neurite growth in the central nervous system. It is a type I membrane protein and belongs to the ROR subfamily of cell surface receptors.

ROR1 has been shown to be expressed on ovarian cancer stem cells, on which it seems to play a functional role in promoting migration/invasion or spheroid formation in vitro and tumor engraftment in immune-deficient mice. Treatment with a humanized mAb specific for ROR1 can inhibit the capacity of ovarian cancer cells to migrate, form spheroids, or engraft in immune-deficient mice.

WO2017/072361 describes several ROR1-specific antibodies, suitable for use in a CAR.

TACI

Transmembrane activator and calcium modulator and cyclophilin ligand (CAML) interactor) TACI (UniProtKB: 014836) is a regulator in immune responses, and like BCMA, is preferentially expressed in mature lymphocytes such as CD27+ memory B cells, especially marginal zone B cells, bone marrow plasma cells and myeloma cells.

Additionally, TACI is expressed on macrophages and mediates macrophage survival. TACI is a lymphocyte-specific member of the tumour necrosis factor (TNF) receptor superfamily, also known as Tumour necrosis factor receptor superfamily member 13B (TNFRSF13B), and can be shed from cells' surface and circulate in its soluble form. In contrast with BCMA, TACI is notably absent from germinal center B cells. TACI is known to function as the receptor for TNFSF13/APRIL and TNFSF13B/BAFF and binds both ligands with high affinity. TACI inhibits B cell expansion and promotes the differentiation and survival of plasma cells.

TACI is a member of the tumor necrosis factor receptor (TNFR) superfamily and serves as a key regulator of B cell function. TACI binds two ligands, APRIL and BAFF, with high affinity and contains two cysteine-rich domains (CRDs) in its extracellular region. However, another form of TACI exists in which the N-terminal CRD is removed by alternative splicing. It has been shown that this shorter form is capable of ligand-induced cell signaling and that the second CRD alone (TACI_d2) contains full affinity for both ligands (Hymowitz et al 2005 Am Soc. Biochem. And Mol. Biol. Inc 280(8) 7218-7227).

The crystal structure of TACI_d2 has been solved along with cocrystal structures of APRILTACI_d2 and APRIL BCMA complexes (Hymowitz et al 2005, as above).

The CRDs of TACI, together with CRDs of other TNFRs, have a common sequence feature, the so-called DXL motif, which consists of a conserved 6-residue sequence (Phe/Tyr/Trp)-Asp-Xaa-Leu-(Val/Thr)-(Arg/Gly) (SEQ ID No. 74). This motif is required for binding to either APRIL or BAFF. The receptor motif binds in a hydrophobic pocket and interacts with two conserved arginine residues on the BAFF surface.

The antigen binding domain of CAR or tanCAR which binds to TACI may be any domain which is capable of binding TACI. For example, the antigen binding domain may comprise a TACI binder derivable from one of the commercially available anti-TACI antibodies listed in the Table 1.

TABLE 1

| Anti-TACI Ab | Company |
| --- | --- |
| 1A1 | BioLegend |
| ab5994 | Abcam |
| Ab79023 | Abcam |
| 11H3 | Affymetrix eBioscience |

The antigen binding domain may comprise one of the TACI binders from clones 2H6, 2G2, 1G6 or 4B11.

These TACI binders have the following sequences:

```
2H6
                                                      (SEQ ID No. 31)
ScFv:  EVQLQQSGPELVKPGASVRMSCKASGYTFTNYVMHWVKQKPGQGLEWIGYI

NPSNDDTKYTEKFKGKATLTSDKSSSTAYMELSSLTSEDSAVYYCARGTHGDYYAL

DYWGQGTSVTVSSGGGGAGGGGSGGGGSDIVLTQSPASLAVSLGQSVTISCRASE

SVEYYGTSLMQWYQQKPGQAPKLLIYGASNVESGVPARFSGSGSGTDFSLNIHPVE

EDDIAMYFCQQSRKVPWTFGGGTKLEIKR (SEQ ID No. 32)
CDR H1:  NYVMH (SEQ ID No. 33)
CDR H2:  YINPSNDDTKYTEKFKG (SEQ ID No. 34)
CDR H3:  GTHGDYYALDY
```

-continued

CDR L1: RASESVEYYGTSLMQ (SEQ ID No. 35)

CDR L2: GASNVES (SEQ ID No. 36)

CDR L3: QQSRKVP (SEQ ID No. 37)

2G2

ScFv: QVTLKESGPGMLQPSQTLSLTCSFSGFSLSTFGMGVGWIRQPSGKGLEWLA
HIWWDDAQYSNPALRSRLTISKDTSKNQVFLKIANVDTADTATYYCSRIHSYYSYDE
GFAYWGQGTLVTVSSGGGGSGGGGSGGGGSDIVMTQSQKFMSTTVGDRVSITCK
ASQNVGTAVAWYQQKPGQSPKLLIYSASNRYTGVPDRFTGSGSGTDFTLTISNMQS
EDLADYFCQQYSSYRTFGGGTKLEIKR (SEQ ID No. 38)

CDR H1: TFGMGVG (SEQ ID No. 39)

CDR H2: HIWWDDAQYSNPALRS (SEQ ID No. 40)

CDR H3: RIHSYYSYDEGFAY (SEQ ID No. 41)

CDR L1: KASQNVGTAVA (SEQ ID No. 42)

CDR L2: SASNRYT (SEQ ID No. 43)

CDR L3: QQYSSY (SEQ ID No. 44)

1G6

VH: QVQLKQSGPGLVAPSQSLSITCTVSGFSLTSYGVDWVRQSPGKGLEWLGIIWG
GGRTNYNSAFKSRLSISKDNSKSQVFLKMNSLQTDDTAMYYCASGDRAADYWGQG
TSVTVSS (SEQ ID No. 45)

CDR H1: SYGVD (SEQ ID No. 47)

CDR H2: IIWGGGRTNYNSAFKS (SEQ ID No. 48)

CDR H3: GDRAADY (SEQ ID No. 49)

VL: DIVMTQSQKFMSTTVGDRVTITCKASQNVGTAVAWYQQKPGQSPKLLIYSASNR
YTGVPVRFTGSGSGTDFTLTINNMQSEDLADYFCQQYSSYPLTFGAGTKLELK (SEQ ID No. 46)

CDR L1: KASQNVGTAVA (SEQ ID No. 50)

CDR L2: SASNRYT (SEQ ID No. 51)

CDR L3: QQYSSYP (SEQ ID No. 52)

4B11

VH: EVQLQQSVAELVRPGASVKLSCTASGFNIKNTYIHWVKQRPEQGLEWIGKIDPA
NGNSEYAPKFQGKATITADTSSNTAYLQLSSLTSEDTTIYYCTSGYGAYWGQGTTLT
VSS (SEQ ID No. 53)

CDR H1: NTYIH (SEQ ID No. 55)

```
                                                 (SEQ ID No. 56)
CDR H2: KIDPANGNSEYAPKFQG (SEQ ID No. 57)
CDR H3: GYGAY (SEQ ID No. 54)
VL: DIVLSQSPSSLAVSIGEKVTLSCKSSQSLLYSSNQKNYLAWFQQKPGQSLKLLIY

WASTREFGVPDRFTGSGSGTDFTLTISSVKTEDLAVYYCQQYYTWTFGGGTKLEIK (SEQ ID No. 58)
CDR L1: KSSQSLLYSSNQKNYLA (SEQ ID No. 59)
CDR L2: WASTREF (SEQ ID No. 60)
CDR L3: QQYYTW
```

The present invention provides an anti-TACI agent, such as an antibody, scFv, CAR or tanCAR which comprises a TCI-binding domain based on one of the clones 2H6, 2G2, 1G6 or 4B111. The anti-TACI agent may comprise one or more CDRs having the sequences shown as SEQ ID Nos 32-37; 39-44; 47-52; 55-60. The agent may comprise one of the following groups of six CDRs: SEQ ID Nos 32-37; SEQ ID Nos 39-44; SEQ ID Nos 47-52 and 55-60.

The anti-TACI agent may comprise the VH and/or VL sequences shown in SEQ ID No. 31 or 38 (VH is before the serine-glycine linker, VL is after the serine-glycine linker), for example in a Fab format. The anti-TACI agent may comprise the VH sequence shown in SEQ ID No. 45 or 53 and/or the VL sequence shown in SEQ ID No. 46 or 54, for example in a Fab format. The anti-TACI agent may comprise the scFv shown in SEQ ID No. 31 or 38 or an scFv formed by linking SEQ ID No. 45 with SEQ ID No. 46 or SEQ ID No. 53 with SEQ ID No. 54.

With all of the above-mentioned sequences, the anti-TACI agent may comprise a sequence having 80%, 85%, 90%, 95% or 98% identity to the given sequence, provided that the variant sequence retains the ability to bind TACI.

TYRP-1

Tyrp1 is a melanocyte-specific gene product involved in melanin synthesis. While mouse Tyrp1 possesses dihydroxyindole carboxylic acid oxidase activity, the function in human melanocytes is less clear. In addition to its role in melanin synthesis, Tyrp1 is involved in stabilizing of tyrosinase protein and modulating its catalytic activity. Tyrp1 is also involved in maintenance of melanosome structure and affects melanocyte proliferation and melanocyte cell death.

WO2009114585 describes several antibodies which bind Tyrp-1. Anti-Tyrp-1 antibodies are also commercially available such as SAB1406566 and HPA000937 from Sigma-Aldrich.

ALK

Anaplastic lymphoma kinase (ALK) is receptor tyrosine kinase belonging to the insulin receptor superfamily. The protein includes an extracellular domain, a hydrophobic stretch corresponding to a single pass transmembrane region, and an intracellular kinase domain. Human ALK sequences are publically available, for example GENBANK® accession numbers NP_004295 (protein), and NM_004304 (nucleic acid) and UniProt Acc. No Q9UM73.

WO2015069922 describes several scFv-type antigen-binding domains which bind ALK

Target Antigens for Cleavable Fabcar

The Fab CAR of the present invention may have two antigen-binding domains, as illustrated schematically in FIG. 9.

In the cleavable FabCAR of the invention, the first and/or second binding domain may bind an antigen which is expressed at a relatively low level on the target cell. For example, it may bind an antigen selected from ROR1, Typr-1, BCMA, TACI and ALK. In particular the target antigen for the second (membrane proximal) binding domain may be an antigen expressed at a relatively low level on the target cell.

Target antigen binding by the first (membrane-distal) binding domain may be used to target the CAR to the tumour. Cleavage of the linker in the tumour allows activation via binding the second target antigen by the second binding domain, leading to tumour cell killing. It should be noted however, that binding of the first target antigen by the first binding domain may also trigger cell killing, but the efficiency of kill may be reduced (compared to killing induced by target antigen binding via the second binding domain) due to inefficient synapse formation.

One of the advantages of the cleavable FabCAR is that the internal binding domain (i.e. the second binding domain) is partially occluded in the intact molecule due to steric hindrance. This can improve safety, where the second target antigen is expressed to some extent on one or more normal tissues, as exposure of the second binding domain to its target antigen will be reduced until the first binding domain is cleaved off, which may not happen until the CAR-expressing cell has reached the tumour.

The second antigen may therefore be expressed at a high level on a tumour cell but at a low level on one of more normal tissues.

The target antigen for the first or second binding domain may be selected from one of the following: ErbB2, MUC1, CD33, CD123, PSMA, EpCAM, GD2, NCAM, Folate binding protein and MUC16.

In particular, the cleavable FabCAR of the invention may comprise binding domains directed against one of the following pairs of target antigens: ErbB2 and MUC1; CD33 and CD123; PSMA and EpCAM; GD2 and NCAM; Folate binding protein and MUC16. In these target antigen pairs, binding domain 1 and binding domain 2 may by either antigen, for example for the target antigen pair ErbB2 and MUC1, binding domain 1 may bind ErbB2 and binding domain 2 may bind MUC1 or binding domain 2 may bind ErbB2 and binding domain 1 may bind MUC1.

In particular, the cleavable FabCAR of the invention may comprise binding domains directed against one of the pairs of target antigens shown in Table 2.

TABLE 2

| Indication | Target antigen for binding domain 1 | Target antigen for binding domain 1 |
|---|---|---|
| Breast cancer | ErbB2 | MUC1 |
| AML | CD33 | CD123 |
| Prostate cancer | PSMA | EpCAM |
| Neuroblastoma | GD2 | NCAM |
| Ovarian cancer | Folate binding protein | MUC16 |

OR Gates

The CAR of the present invention may be used in a combination with one or more other activatory or inhibitory chimeric antigen receptors. For example, they may be used in combination with one or more other CARs in a "logic-gate", a CAR combination which, when expressed by a cell, such as a T cell, are capable of detecting a particular pattern of expression of at least two target antigens. If the at least two target antigens are arbitrarily denoted as antigen A and antigen B, the three possible options are as follows:

"OR GATE"—T cell triggers when either antigen A or antigen B is present on the target cell "AND GATE"—T cell triggers only when both antigens A and B are present on the target cell "AND NOT GATE"—T cell triggers if antigen A is present alone on the target cell, but not if both antigens A and B are present on the target cell Engineered T cells expressing these CAR combinations can be tailored to be exquisitely specific for cancer cells, based on their particular expression (or lack of expression) of two or more markers.

Such "Logic Gates" are described, for example, in WO2015/075469, WO2015/075470 and WO2015/075470.

An "OR Gate" comprises two or more activatory CARs each directed to a distinct target antigen expressed by a target cell. The advantage of an OR gate is that the effective targetable antigen is increased on the target cell, as it is effectively antigen A+antigen B. This is especially important for antigens expressed at variable or low density on the target cell, as the level of a single antigen may be below the threshold needed for effective targeting by a CAR-T cell. Also, it avoids the phenomenon of antigen escape. For example, some lymphomas and leukemias become CD19 negative after CD19 targeting: using an OR gate which targets CD19 in combination with another antigen provides a "back-up" antigen, should this occur.

The FabCAR of the present invention may be used in an OR gate in combination with a second CAR against a second target antigen expressed by the target cell.

For an anti-BCMA FabCAR, the OR gate may comprise a CAR against a second antigen expressed in B cells or plasma cells, such as CD19, TACI or FcRL5.

The second CAR may have any suitable antigen binding domain, for example a binding domain based on an scFv, a domain antibody (dAb) or a Fab.

The OR gate may be a double-Fab CAR. In this respect, the cell may express two separate CARs with Fab-type antigen binding domains. The FabCARs may, for example, be against BCMA and TACI or BCMA and FcRL5.

The present invention also provides a triple OR gate, comprising three CARs, at least one of which is a FabCAR according to the first aspect of the invention. A triple OR gate may, for example, comprise a BCMA Fab CAR, a CD19 CAR and a FcRL5 CAR or Fab CAR.

The second CAR may comprise a spacer to spatially separate the antigen binding domain from the transmembrane domain and provide a degree of flexibility. A variety of sequences are commonly used as spacers for CAR, for example, an IgG1 Fc region, an IgG1 hinge (as described above) or a human CD8 stalk. The spacer may comprise a coiled-coil domain, for example as described in WO2016/151315.

The second CAR comprises an activating endodomain. It may, for example comprise the endodomain from CD3ζ. It may comprise one or more co-stimulatory domains as described above. For example, it may comprise the endodomains from CD28, OX-40 or 4-1 BB.

CD19 BINDERs

Several anti-CD19 antibodies have been previously described in a CAR format, such as fmc63, 4G7, SJ25C1, CAT19 (as described in WO2016/139487) and CD19ALAb (as described in WO2016/102965)

An anti-CD19 CAR for use in a double or triple OR gate of the present invention may comprise an antigen-binding domain, such as an scFv-type antigen binding domain, derived from one of these anti-CD19 antibodies.

The CD19-binding domain may comprise:

a) a heavy chain variable region (VH) having complementarity determining regions (CDRs) with the following sequences:
CDR1—GYAFSSS (SEQ ID No. 61);
CDR2—YPGDED (SEQ ID No. 62)
CDR3—SLLYGDYLDY (SEQ ID No. 63); and b) a light chain variable region (VL) having CDRs with the following sequences:

```
                                       (SEQ ID No. 64)
            CDR1 - SASSSVSYMH;

(SEQ ID No. 65)
            CDR2 - DTSKLAS (SEQ ID No. 66)
            CDR3 - QQWNINPLT.
```

It may be possible to introduce one or more mutations (substitutions, additions or deletions) into each CDR without negatively affecting CD19-binding activity. Each CDR may, for example, have one, two or three amino acid mutations.

The CDRs may be in the format of a single-chain variable fragment (scFv), which is a fusion protein of the heavy variable region (VH) and light chain variable region (VL) of an antibody, connected with a short linker peptide of ten to about 25 amino acids. The scFv may be in the orientation VH-VL, i.e. the VH is at the amino-terminus of the CAR molecule and the VL domain is linked to the spacer and, in turn the transmembrane domain and endodomain.

The CDRs may be grafted on to the framework of a human antibody or scFv. For example, the CAR of the present invention may comprise a CD19-binding domain consisting or comprising one of the following sequences The anti-CD19 CAR may comprise the following VH sequence:

```
                                       SEQ ID No. 67
VH sequence from murine monoclonal antibody
QVQLQQSGPELVKPGASVKISCKASGYAFSSSWMNWVKQRPGKGLEWIGR

IYPGDEDTNYSGKFKDKATLTADKSSTTAYMQLSSLTSEDSAVYFCARSL

LYGDYLDYWGQGTTLTVSS
```

The anti-CD19 CAR may comprise the following VL sequence:

SEQ ID No 75
VL sequence from murine monoclonal antibody
QIVLTQSPAIMSASPGEKVTMTCSASSSVSYMHWYQQKSGTSPKRWIYDT

SKLASGVPDRFSGSGSGTSYFLTINNMEAEDAATYYCQQWNINPLTFGAG

TKLELKR

The anti-CD19 CAR may comprise the following scFv sequence:

SEQ ID No 76
VH-VL scFv sequence from murine monoclonal antibody
QVQLQQSGPELVKPGASVKISCKASGYAFSSSWMNWVKQRPGKGLEWIGR

IYPGDEDTNYSGKFKDKATLTADKSSITAYMQLSSLTSEDSAVYFCARSL

LYGDYLDYWGQGTTLTVSSGGGGSGGGGSGGGGSQIVLTQSPAIMSASPG

EKVTMTCSASSSVSYMHWYQQKSGTSPKRWIYDTSKLASGVPDRFSGSGS

GTSYFLTINNMEAEDAATYYCQQWNINPLTFGAGTKLELKR.

The percentage identity between two polypeptide sequences may be readily determined by programs such as BLAST which is freely available at http://blast.ncbi.nlm.nih.gov.

FCRL5

Fc receptor-like protein 5 (FcRL5) is a member of the immunoglobulin receptor superfamily and the Fc-receptor like family FcRL5 is a single-pass type I membrane protein and contains 8 immunoglobulin-like C2-type domains. The mature protein is 106 kDa.

FCRL5 has a cytoplasmic tail with two inhibitory ITIM phosphorylation signaling motifs. It inhibits B cell antigen receptor signaling by recruiting SHP1 upon B cell antigen receptor co-stimulation, resulting in diminished calcium influx and protein tyrosine phosphorylation. Co-stimulation of FCRL5 and the B cell antigen receptor promotes proliferation and differentiation of naive B cells. FCRL5 is expressed on both mature B cells and plasma cells, and is induced by EBV proteins. It is overexpressed on malignant B cells of hairy cell leukemia, chronic lymphocytic leukemia, mantle cell lymphoma, and multiple myeloma patients.

Commercially available monoclonal antibodies against FcRL5 are known, such as CD307e (ThermoFisher) and REA391 (Miltenyi Biotec).

WO2016090337 describes several scFv-type antigen-binding domains which bind FcRL5.

In an OR gate of the invention, an anti-FcRL5 CAR may comprise a dAb, scFv or Fab antigen binding domain. The FcRL5 may comprise a Fab antigen-binding domain.

Nucleic Acid Construct

The present invention also provides a nucleic acid construct encoding a chimeric receptor of the invention.

A nucleic acid construct encoding a FabCAR (FIG. 2a) may have the structure:
VH-CH-spacer-TM-endo-coexpr-VL-CL or
VL-CL-spacer-TM-endo-coexpr-VH-CH
in which:
VH is a nucleic acid sequence encoding a heavy chain variable region;
CH is a nucleic acid sequence encoding a heavy chain constant region spacer is a nucleic acid encoding a spacer;

TM is a nucleic acid sequence encoding a transmembrane domain;
endo is a nucleic acid sequence encoding an endodomain;
coexpr is a nucleic acid sequence enabling co-expression of the first and second polypeptides;
VL is a nucleic acid sequence encoding a light chain variable region; and
CL is a nucleic acid sequence encoding a light chain constant region.

For both structures mentioned above, nucleic acid sequences encoding the two polypeptides may be in either order in the construct.

There is also provided a nucleic acid construct encoding an OR gate, which comprises two of more CARs, at least one of which is a FabCAR according to the present invention.

A nucleic acid construct encoding a double OR gate may have the structure:
VH-CH-spacer1-TM1-endo1-coexpr1-VL-CL-coexpr2-AgBD-spacer2-TM2-endo2; or
VL-CL-spacer-TM1-endo1-coexpr1-VH-CH-coexpr2-AgBD-spacer2-TM2-endo2 in which:
VH is a nucleic acid sequence encoding a heavy chain variable region of the first CAR;
CH is a nucleic acid sequence encoding a heavy chain constant region of the first CAR;
Spacer 1 is a nucleic acid sequence encoding a spacer of the first CAR;
TM1 is a nucleic acid sequence encoding a transmembrane domain of the first CAR;
Endo1 is a nucleic acid sequence encoding an endodomain of the first CAR;
Coexpr1 and coexpr2, which my be the same or different, are nucleic acid sequences enabling co-expression of the first and second polypeptides of the first CAR; and the first and second CARs;
VL is a nucleic acid sequence encoding a light chain variable region of the first CAR;
CL is a nucleic acid sequence encoding a light chain constant region of the first CAR; AgBD is a nucleic acid sequence encoding an antigen binding domain of the second CAR;
Spacer2 is a nucleic acid sequence encoding a spacer of the second CAR;
TM2 is a nucleic acid sequence encoding a transmembrane domain of the second CAR; and
Endo2 is a nucleic acid sequence encoding an endodomain of the second CAR.

The antigen-binding domain of the second CAR may, for example, be an scFv or a dAb.

For both structures mentioned above, nucleic acid sequences encoding the two polypeptides of the first CAR; and the nucleic acid sequences encoding the first and second CARs may be in any order in the construct.

A nucleic acid construct encoding a double FabCAR OR gate may have the structure:
VH1-CH1-spacer1-TM1-endo1-coexpr1-VL1-CL1-coexpr2-VH2-CH2-spacer2-TM2-endo2-coexpr3-VL2-CL2;
VH1-CH1-spacer1-TM1-endo1-coexpr1-VL1-CL1-coexpr2-VL2-CL2-spacer2-TM2-endo2-coexpr3-VH2-CH2;
VL1-CL1-spacer1-TM1-endo1-coexpr1-VH1-CH1-coexpr2-VL2-CL2-spacer2-TM2-endo2-coexpr3-VH2-CH2;
or VL1-CL1-spacer1-TM1-endo1-coexpr1-VH1-CH1-coexpr2-VH2-CH2-spacer2-TM2-endo2-coexpr3-VL2-CL2;
in which:

VH1 is a nucleic acid sequence encoding a heavy chain variable region of the first CAR;

CH1 is a nucleic acid sequence encoding a heavy chain constant region of the first CAR; Spacer 1 is a nucleic acid sequence encoding a spacer of the first CAR;

TM1 is a nucleic acid sequence encoding a transmembrane domain of the first CAR;

Endo1 is a nucleic acid sequence encoding an endodomain of the first CAR;

Coexpr1, coexpr2, and coexpr 3 which may be the same or different, are nucleic acid sequences enabling co-expression of the first and second polypeptides of the first CAR; and the first and second polypeptides of the second CAR;

VL2 is a nucleic acid sequence encoding a light chain variable region of the second CAR;

CL2 is a nucleic acid sequence encoding a light chain constant region of the second CAR;

VH2 is a nucleic acid sequence encoding a heavy chain variable region of the second CAR;

CH2 is a nucleic acid sequence encoding a heavy chain constant region of the second CAR; Spacer 2 is a nucleic acid sequence encoding a spacer of the second CAR;

TM2 is a nucleic acid sequence encoding a transmembrane domain of the second CAR;

Endo2 is a nucleic acid sequence encoding an endodomain of the second CAR;

VL2 is a nucleic acid sequence encoding a light chain variable region of the second CAR;

CL2 is a nucleic acid sequence encoding a light chain constant region of the second CAR; As used herein, the terms "polynucleotide", "nucleotide", and "nucleic acid" are intended to be synonymous with each other.

It will be understood by a skilled person that numerous different polynucleotides and nucleic acids can encode the same polypeptide as a result of the degeneracy of the genetic code. In addition, it is to be understood that skilled persons may, using routine techniques, make nucleotide substitutions that do not affect the polypeptide sequence encoded by the polynucleotides described here to reflect the codon usage of any particular host organism in which the polypeptides are to be expressed.

Nucleic acids according to the invention may comprise DNA or RNA. They may be single-stranded or double-stranded. They may also be polynucleotides which include within them synthetic or modified nucleotides. A number of different types of modification to oligonucleotides are known in the art. These include methylphosphonate and phosphorothioate backbones, addition of acridine or polylysine chains at the 3' and/or 5' ends of the molecule. For the purposes of the use as described herein, it is to be understood that the polynucleotides may be modified by any method available in the art. Such modifications may be carried out in order to enhance the in vivo activity or life span of polynucleotides of interest.

The terms "variant", "homologue" or "derivative" in relation to a nucleotide sequence include any substitution of, variation of, modification of, replacement of, deletion of or addition of one (or more) nucleic acid from or to the sequence.

In the structure above, "coexpr" is a nucleic acid sequence enabling co-expression of two polypeptides as separate entities. It may be a sequence encoding a cleavage site, such that the nucleic acid construct produces both polypeptides, joined by a cleavage site(s). The cleavage site may be self-cleaving, such that when the polypeptide is produced, it is immediately cleaved into individual peptides without the need for any external cleavage activity.

The cleavage site may be any sequence which enables the two polypeptides to become separated.

The term "cleavage" is used herein for convenience, but the cleavage site may cause the peptides to separate into individual entities by a mechanism other than classical cleavage. For example, for the Foot-and-Mouth disease virus (FMDV) 2A self-cleaving peptide (see below), various models have been proposed for to account for the "cleavage" activity: proteolysis by a host-cell proteinase, autoproteolysis or a translational effect (Donnelly et al (2001) J. Gen. Virol. 82:1027-1041). The exact mechanism of such "cleavage" is not important for the purposes of the present invention, as long as the cleavage site, when positioned between nucleic acid sequences which encode proteins, causes the proteins to be expressed as separate entities.

The cleavage site may, for example be a furin cleavage site, a Tobacco Etch Virus (TEV) cleavage site or encode a self-cleaving peptide.

A 'self-cleaving peptide' refers to a peptide which functions such that when the polypeptide comprising the proteins and the self-cleaving peptide is produced, it is immediately "cleaved" or separated into distinct and discrete first and second polypeptides without the need for any external cleavage activity.

The self-cleaving peptide may be a 2A self-cleaving peptide from an aphtho- or a cardiovirus. The primary 2A/2B cleavage of the aptho- and cardioviruses is mediated by 2A "cleaving" at its own C-terminus. In apthoviruses, such as foot-and-mouth disease viruses (FMDV) and equine rhinitis A virus, the 2A region is a short section of about 18 amino acids, which, together with the N-terminal residue of protein 2B (a conserved proline residue) represents an autonomous element capable of mediating "cleavage" at its own C-terminus (Donelly et al (2001) as above).

"2A-like" sequences have been found in picornaviruses other than aptho- or cardioviruses, 'picornavirus-like' insect viruses, type C rotaviruses and repeated sequences within *Trypanosoma* spp and a bacterial sequence (Donnelly et al (2001) as above).

The cleavage site may comprise the 2A-like sequence shown as SEQ ID No.77

(RAEGRGSLLTCGDVEENPGP).

Chimeric Cytokine Receptor

The nucleic acid construct of the invention may also comprise one or more nucleic acid sequence(s) encoding a chimeric cytokine receptor.

Chimeric cytokine receptors are described in WO2017/029512, which is hereby incorporated by reference.

The chimeric cytokine receptor may comprise:
an exodomain which binds to a ligand; and
a cytokine receptor endodomain.

The ligand may, for example, be a tumour secreted factor, a chemokine or a cell-surface antigen.

The chimeric cytokine receptor comprises two polypeptides:
(i) a first polypeptide which comprises:
    (a) a first antigen-binding domain which binds a first epitope of the ligand
    (b) a first chain of the cytokine receptor endodomain; and (ii) a second polypeptide which comprises:
   (a) a second antigen-binding domain which binds a second epitope of the ligand (b) a second chain of the cytokine-receptor endodomain.

In an alternative embodiment, the chimeric cytokine receptor may comprise a dimerization domain; and a cytokine receptor endodomain.

Dimerisation may occur spontaneously, in which case the chimeric transmembrane protein will be constitutively active. Alternatively, dimerization may occur only in the presence of a chemical inducer of dimerization (CID) in which case the transmembrane protein only causes cytokine-type signalling in the presence of the CID.

Suitable dimerization domains and CIDs are described in WO2015/150771, the contents of which are hereby incorporated by reference.

For example, one dimerization domain may comprise the rapamycin binding domain of FK-binding protein 12 (FKBP12), the other may comprise the FKBP12-Rapamycin Binding (FRB) domain of mTOR; and the CID may be rapamycin or a derivative thereof.

Where the dimerization domain spontaneously heterodimerizes, it may be based on the dimerization domain of an antibody. In particular it may comprise the dimerization portion of a heavy chain constant domain (CH) and a light chain constant domain (CL). The "dimerization portion" of a constant domain is the part of the sequence which forms the inter-chain disulphide bond.

Figure 4:
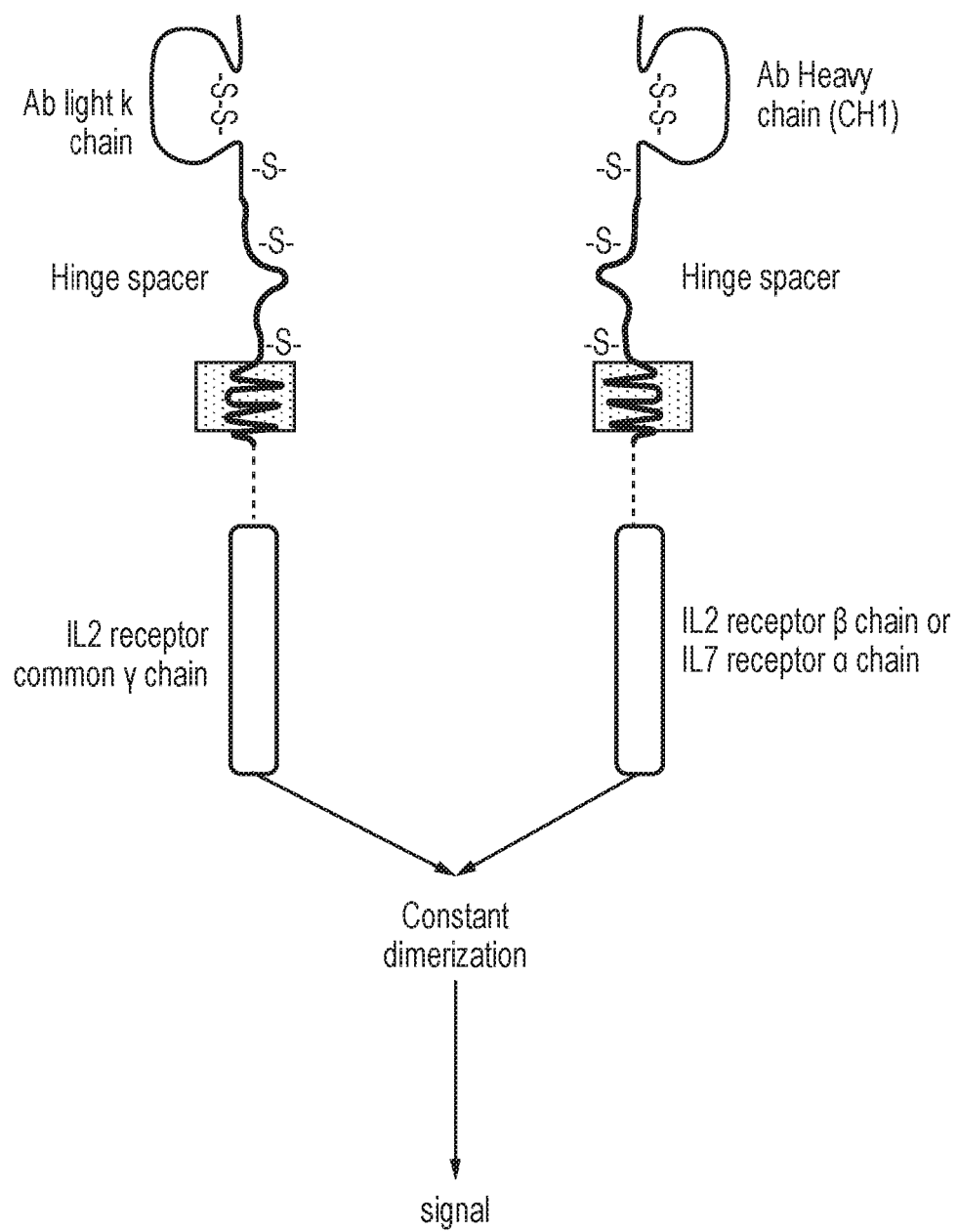
FIG. 4: Schematic diagram illustrating a constitutively active chimeric cytokine receptor. The chimeric transmembrane protein comprises a dimerization domain and a cytokine receptor endodomain. The embodiment shown has a "Fab" type architecture, as the dimerization domain comprises antibody-type heavy and light chain constant regions. Constant dimerization between these domains brings together the IL2 receptor common γ chain with either the IL-2 receptor β chain or the IL-7 receptor α chain, leading to constitutive cytokine signalling.

The chimeric cytokine receptor may comprise the Fab portion of an antibody as exodomain, for example as illustrated schematically in FIG. 4.

The chimeric cytokine receptor may comprise two polypeptides:
(i) a first polypeptide which comprises:
   (a) a first dimerisation domain; and
   (b) a first chain of a cytokine receptor endodomain; and
(ii) a second polypeptide which comprises:
   (a) a second dimerization domain, which dimerises with the first dimerization domain; and
   (b) a second chain of the cytokine-receptor endodomain.

The chimeric cytokine receptor may comprise two polypeptides:
(i) a first polypeptide which comprises:
   (a) a heavy chain constant domain (CH)
   (b) a first chain of the cytokine receptor endodomain; and
(ii) a second polypeptide which comprises:
   (a) a light chain constant domain (CL)
   (b) a second chain of the cytokine-receptor endodomain.

The cytokine receptor endodomain may, for example, comprise:
(i) IL-2 receptor β-chain endodomain
(ii) IL-7 receptor α-chain endodomain; or
(iii) IL-15 receptor α-chain endodomain; and/or
(iv) common γ-chain receptor endodomain.

A nucleic acid construct encoding a Fab-type constitutively active chimeric cytokine receptor may have the following general structure:
CH-CRE1-coexpr-CL-CRE2; or
CL-CRE2-coexpr-CH-CRE1 in which:
CH is a nucleic acid sequence encoding a heavy chain constant domain of the first polypeptide;
CRE1 is a nucleic acid sequence encoding a first chain of the cytokine receptor endodomain of the first polypeptide;
coexpr encodes a sequence enabling co-expression of the first and second polypeptides;
CL is a nucleic acid sequence encoding a heavy chain constant domain of the second polypeptide;
CRE2 is a nucleic acid sequence encoding a second chain of the cytokine receptor endodomain of the second polypeptide.

The nucleic acid construct of the present invention may encode a FabCAR and a chimeric cytokine receptor.

Vector

The present invention also provides a vector, or kit of vectors, which comprises one or more nucleic acid sequence(s) encoding a chimeric receptor according to the invention. Such a vector may be used to introduce the nucleic acid sequence(s) into a host cell so that it expresses a CAR according to the first aspect of the invention.

There is also provided a vector comprising a nucleic acid construct of nucleic acid sequences encoding a FabCAR and a chimeric cytokine receptor.

The vector may, for example, be a plasmid or a viral vector, such as a retroviral vector or a lentiviral vector, or a transposon based vector or synthetic mRNA.

The vector may be capable of transfecting or transducing a cell, such as a T cell or a NK cell.

Cell

The present invention provides a cell which comprises a chimeric antigen receptor of the invention. The cell may comprise two of more CARs, for example it may comprise a double or triple OR gate as described above.

There is also provided a cell which co-expresses a FabCAR or an OR gate of the invention and a chimeric cytokine receptor.

The cell may comprise a nucleic acid or a vector of the present invention.

The cell may be a cytolytic immune cell such as a T cell or an NK cell.

T cells or T lymphocytes are a type of lymphocyte that play a central role in cell-mediated immunity. They can be distinguished from other lymphocytes, such as B cells and natural killer cells (NK cells), by the presence of a T-cell receptor (TCR) on the cell surface. There are various types of T cell, as summarised below.

Helper T helper cells (TH cells) assist other white blood cells in immunologic processes, including maturation of B cells into plasma cells and memory B cells, and activation of cytotoxic T cells and macrophages. TH cells express CD4 on their surface. TH cells become activated when they are presented with peptide antigens by MHC class II molecules on the surface of antigen presenting cells (APCs). These cells can differentiate into one of several subtypes, including TH1, TH2, TH3, TH17, Th9, or TFH, which secrete different cytokines to facilitate different types of immune responses.

Cytolytic T cells (TC cells, or CTLs) destroy virally infected cells and tumor cells, and are also implicated in transplant rejection. CTLs express the CD8 at their surface. These cells recognize their targets by binding to antigen associated with MHC class I, which is present on the surface of all nucleated cells. Through IL-10, adenosine and other molecules secreted by regulatory T cells, the CD8+ cells can be inactivated to an anergic state, which prevent autoimmune diseases such as experimental autoimmune encephalomyelitis.

Memory T cells are a subset of antigen-specific T cells that persist long-term after an infection has resolved. They quickly expand to large numbers of effector T cells upon re-exposure to their cognate antigen, thus providing the immune system with "memory" against past infections.

Memory T cells comprise three subtypes: central memory T cells (TCM cells) and two types of effector memory T cells (TEM cells and TEMRA cells). Memory cells may be either CD4+ or CD8+. Memory T cells typically express the cell surface protein CD45RO.

Regulatory T cells (Treg cells), formerly known as suppressor T cells, are crucial for the maintenance of immunological tolerance. Their major role is to shut down T cell-mediated immunity toward the end of an immune reaction and to suppress auto-reactive T cells that escaped the process of negative selection in the thymus.

Two major classes of CD4+ Treg cells have been described—naturally occurring Treg cells and adaptive Treg cells.

Naturally occurring Treg cells (also known as CD4+ CD25+FoxP3+ Treg cells) arise in the thymus and have been linked to interactions between developing T cells with both myeloid (CD11c+) and plasmacytoid (CD123+) dendritic cells that have been activated with TSLP. Naturally occurring Treg cells can be distinguished from other T cells by the presence of an intracellular molecule called FoxP3. Mutations of the FOXP3 gene can prevent regulatory T cell development, causing the fatal autoimmune disease IPEX.

Adaptive Treg cells (also known as Tr cells or Th3 cells) may originate during a normal immune response.

The cell may be a Natural Killer cell (or NK cell). NK cells form part of the innate immune system. NK cells provide rapid responses to innate signals from virally infected cells in an MHC independent manner NK cells (belonging to the group of innate lymphoid cells) are defined as large granular lymphocytes (LGL) and constitute the third kind of cells differentiated from the common lymphoid progenitor generating B and T lymphocytes. NK cells are known to differentiate and mature in the bone marrow, lymph node, spleen, tonsils and thymus where they then enter into the circulation.

The cells of the invention may be any of the cell types mentioned above.

Cells according to the invention may either be created ex vivo either from a patient's own peripheral blood (1st party), or in the setting of a haematopoietic stem cell transplant from donor peripheral blood (2nd party), or peripheral blood from an unconnected donor (3rd party).

Alternatively, cells may be derived from ex vivo differentiation of inducible progenitor cells or embryonic progenitor cells to, for example, T or NK cells. Alternatively, an immortalized T-cell line which retains its lytic function and could act as a therapeutic may be used.

In all these embodiments, chimeric polypeptide-expressing cells are generated by introducing DNA or RNA coding for the chimeric polypeptide by one of many means including transduction with a viral vector, transfection with DNA or RNA.

The cell of the invention may be an ex vivo cell from a subject. The cell may be from a peripheral blood mononuclear cell (PBMC) sample. The cells may be activated and/or expanded prior to being transduced with nucleic acid encoding the molecules providing the chimeric polypeptide according to the first aspect of the invention, for example by treatment with an anti-CD3 monoclonal antibody.

The cell of the invention may be made by:
(i) isolation of a cell-containing sample from a subject or other sources listed above; and
(ii) transduction or transfection of the cells with one or more a nucleic acid sequence(s) encoding a chimeric polypeptide.

The cells may then by purified, for example, selected on the basis of expression of the antigen-binding domain of the antigen-binding polypeptide.

Pharmaceutical Composition

The present invention also relates to a pharmaceutical composition containing a plurality of cells according to the invention.

The pharmaceutical composition may additionally comprise a pharmaceutically acceptable carrier, diluent or excipient. The pharmaceutical composition may optionally comprise one or more further pharmaceutically active polypeptides and/or compounds. Such a formulation may, for example, be in a form suitable for intravenous infusion.

Method of Treatment

The present invention provides a method for treating a disease which comprises the step of administering the cells of the present invention (for example in a pharmaceutical composition as described above) to a subject.

A method for treating a disease relates to the therapeutic use of the cells of the present invention. Herein the cells may be administered to a subject having an existing disease or condition in order to lessen, reduce or improve at least one symptom associated with the disease and/or to slow down, reduce or block the progression of the disease.

The method for preventing a disease relates to the prophylactic use of the cells of the present invention. Herein such cells may be administered to a subject who has not yet contracted the disease and/or who is not showing any symptoms of the disease to prevent or impair the cause of the disease or to reduce or prevent development of at least one symptom associated with the disease. The subject may have a predisposition for, or be thought to be at risk of developing, the disease.

The method may involve the steps of:
(i) isolating a cell-containing sample;
(ii) transducing or transfecting such cells with a nucleic acid sequence or vector provided by the present invention;
(iii) administering the cells from (ii) to a subject.

The cell-containing sample may be isolated from a subject or from other sources, as described above.

The present invention provides a cell of the present invention for use in treating and/or preventing a disease.

The invention also relates to the use of a cell of the present invention in the manufacture of a medicament for the treatment of a disease.

The disease to be treated by the methods of the present invention may be a cancerous disease, such as bladder cancer, breast cancer, colon cancer, endometrial cancer, kidney cancer (renal cell), leukaemia, lung cancer, melanoma, non-Hodgkin lymphoma, pancreatic cancer, prostate cancer and thyroid cancer.

The disease may be Multiple Myeloma (MM), B-cell Acute Lymphoblastic Leukaemia (B-ALL), Chronic Lymphocytic Leukaemia (CLL), Neuroblastoma, T-cell acute Lymphoblastic Leukaema (T-ALL) or diffuse large B-cell lymphoma (DLBCL).

The disease may be a plasma cell disorder such as plasmacytoma, plasma cell leukemia, multiple myeloma, macroglobulinemia, amyloidosis, Waldenstrom's macroglobulinemia, solitary bone plasmacytoma, extramedullary plasmacytoma, osteosclerotic myeloma, heavy chain diseases, monoclonal gammopathy of undetermined significance or smoldering multiple myeloma.

The cells of the present invention may be capable of killing target cells, such as cancer cells. The target cell may be characterised by the presence of a tumour secreted ligand or chemokine ligand in the vicinity of the target cell. The target cell may be characterised by the presence of a soluble ligand together with the expression of a tumour-associated antigen (TAA) at the target cell surface.

The cells and pharmaceutical compositions of present invention may be for use in the treatment and/or prevention of the diseases described above.

The invention will now be further described by way of Examples, which are meant to serve to assist one of ordinary skill in the art in carrying out the invention and are not intended in any way to limit the scope of the invention.

EXAMPLES

Example 1—Expression of BCMA on Surface of Multiple Myeloma Cells

Primary myeloma cells were isolated by performing a CD138 immunomagnetic selection on fresh bone marrow samples from Multiple myeloma patients that were known to have frank disease. These cells were stained with the BCMA specific J6MO mAb (GSK) which was conjugated to PE. At the same time, a standard of beads with known numbers of binding sites was generated using the PE Quantibrite bead kit (Becton Dickenson) as per the manufacturer's instructions. The BCMA copy number on myeloma cells was derived by correlating the mean-fluorescent intensity from the myeloma cells with the standard curve derived from the beads. It was found that the range of BCMA copy number on a myeloma cell surface is low: at 348.7-4268.4 BCMA copies per cell with a mean of 1181 and a median of 1084.9 (FIG. 1). This is considerably lower than e.g. CD19 and GD2, classic targets for CARs.

Example 2—Construction of Anti-BCMA FabCARs and Comparison with Anti-BCMA scFv CARs A panel of CAR-encoding nucleic acid constructs were generated as follows:

RQR8-2A-aBCMAscFv-CD8STK-41 BBZ—single chain Fv CAR construct

RQR8-2A-aBCMAFAb-CD8STK-41 BBZ—Fab based CAR construct

RQR8-2A-aBCMA_C11 D5.3-CD8STK-41 BB-z— bb2121 scFv CAR construct (positive control)

The anti-BCMA scFv and Fab domains included the VH and VL sequences for the anti-BCMA Ab 1 described above (SEQ ID Nos 5 and 6 respectively). All constructs are co-expressed with the sort-suicide gene RQR8, which is described in WO2013/153391, with BCMA binding moieties in either in scFv or Fab format.

Example 3—Testing of CAR Expression

To compare expression of the CARs in different formats, T-cells were transduced with scFv or Fab CARs and the receptors detected on the cells surface by flow cytometry. CAR expression is detected by co-staining T cells with soluble BCMA-FC and QBEND10 (to detect expression of RQR8).

Example 4—FACs-Based Killing Assay (FBK)

The capacity of the CAR-T cells to kill target cells expressing BCMA was investigated using a FACS-based killing assay. T-cells were co-cultured with target cells at effector to target ratios of 1:4 and 1:8. SupT1 cells engineered to express a physiological level of BCMA antigen were used as target cells: averaging 686 copies of BCMA per cell (SupT1-BCMA low). Target cells were also created expressing a very low level of BCMA: averaging 81 copies of BCMA per cell (JeKo-1). Non-engineered SupT1 cells (SupT1-NT) were also used as a negative control. Assays were carried out in a 96-well plate in 0.2 ml total volume using $5\times10^4$ transduced target cells per well. The co-cultures are set up after being normalised for transduction efficiency. FBK was assayed after 24h and 72h of incubation.

Figure 5A:
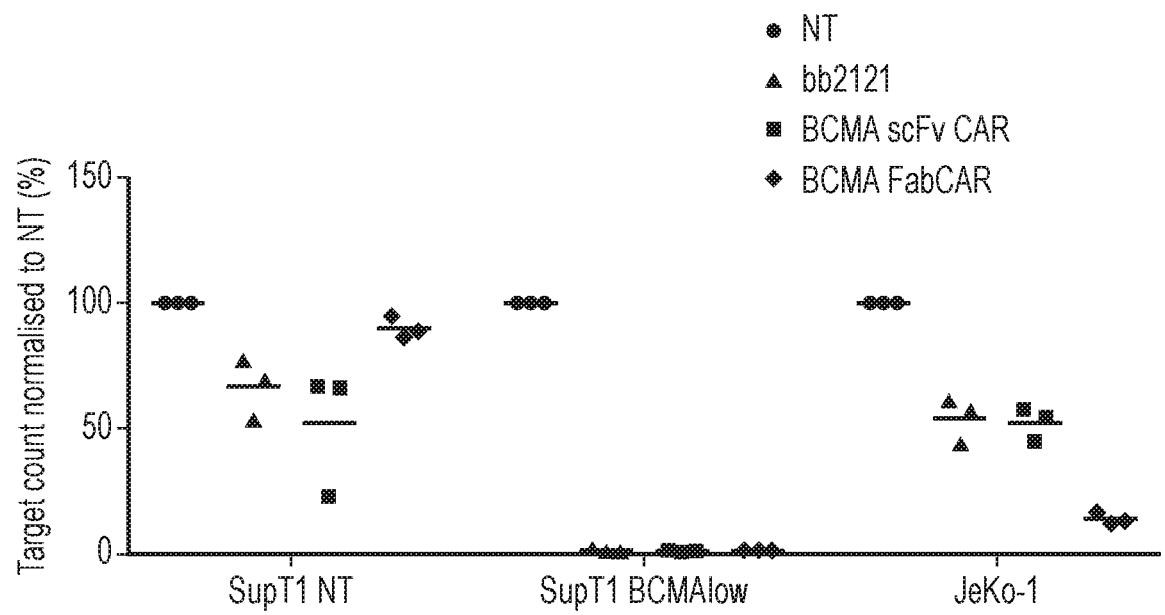
FIG. 5: Results of a killing assay comparing an anti-BCMA CAR in and scFv and FabCAR format. CAR expressing cells were co-cultured with non BCMA-expressing (SupT1 NT), low BCMA-expressing (SupT1 BCMAlow) or very low BCMA-expressing (JeKo-1) target cells at a 1:4 (FIG. 5A) or 1:8 (FIG. 5B) ratio. A previously characterised anti-BCMA CAR, bb2121, was used as a positive control. After 24 hours, killing of target cells was assayed by FACS and the target cell count normalised to counts obtained with untransfected T-cells (NT).
Figure 5B:
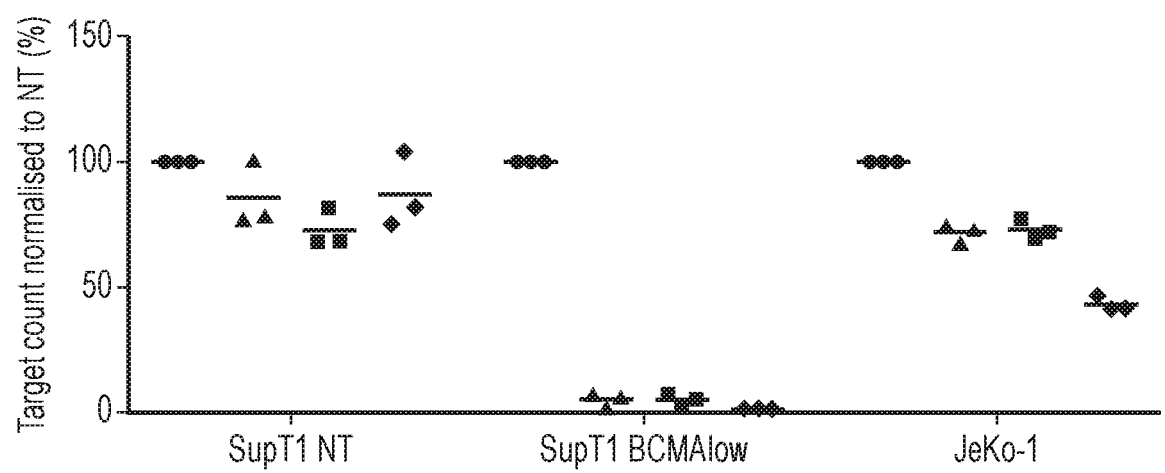
Figure 6A:
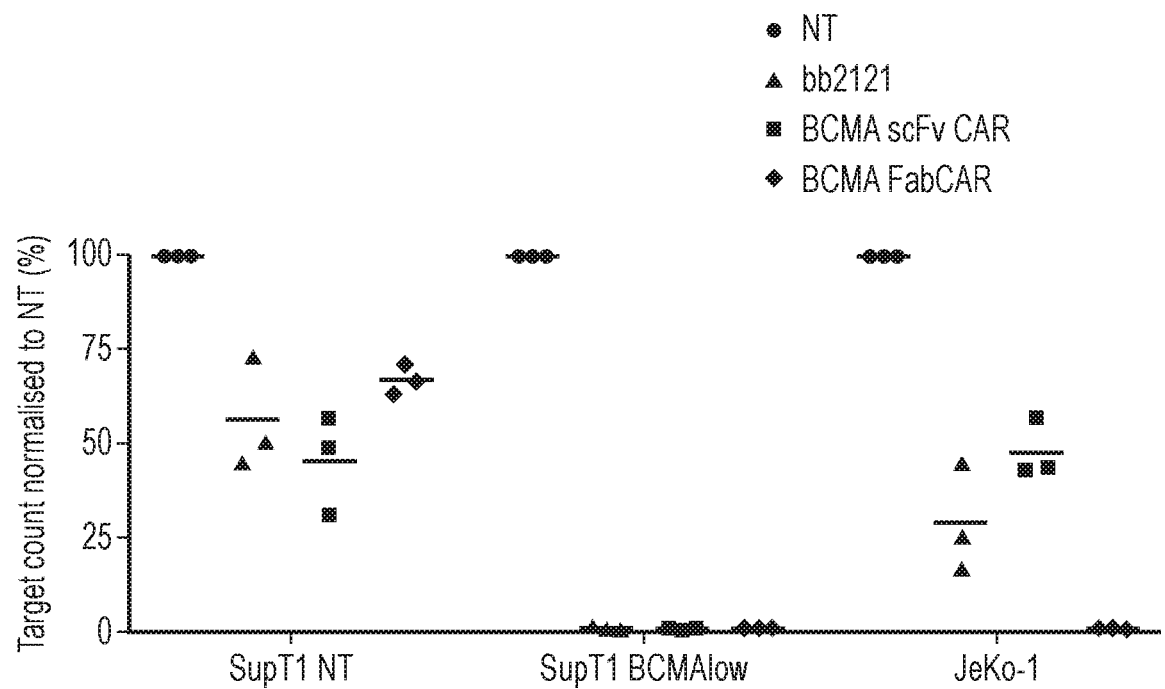
FIG. 6: Results of a killing assay comparing an anti-BCMA CAR in an scFv and FabCAR format. CAR expressing cells were co-cultured with non BCMA-expressing (SupT1 NT), low BCMA-expressing (SupT1 BCMAlow) or very low BCMA-expressing (JeKo-1) target cells at a 1:4 (FIG. 6A) or 1:8 (FIG. 6B) ratio. A previously characterised anti-BCMA CAR, bb2121, was used as a positive control. After 72 hours, killing of target cells was assayed by FACS and the target cell count normalised to counts obtained with untransfected T-cells (NT).
Figure 6B:
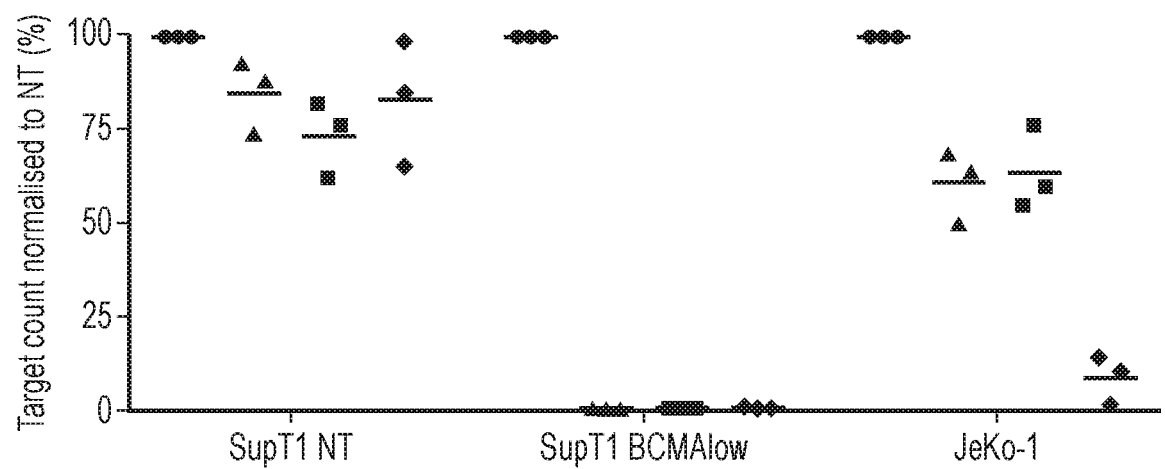

The results are shown in FIGS. 5 and 6. After 24 hours co-culture (FIG. 5), both the BCMA scFv CAR and the BCMA FabCAR showed successful killing of target cells expressing a low level of BCMA antigen. However the BCMA FabCAR showed superior killing to the equivalent scFv CAR of target cells expressing a very low level of BCMA (JeKo-1). The BCMA FabCAR also showed superior killing to the other BCMA scFv CAR, bb2121. After 72 hours (FIG. 6), a similar pattern is seen. At a 1:8 E:T ratio, the BCMA FabCAR gave near complete killing of the very low BCMA-expressing target cells, whereas the scFv CAR with the equivalent binder only showed partial target cell killing.

Example 5—Cytokine Release

Secretion of IL-2 and Interferon-gamma (IFNγ) by CAR T-cells was measured by collecting supernatant at 24 hr from co-cultures, as described in example 4, at a 1:4 and a 1:8 effector:target ratio. Production of IL-2 and IFN-G was detected by ELISA.

Figure 7A:
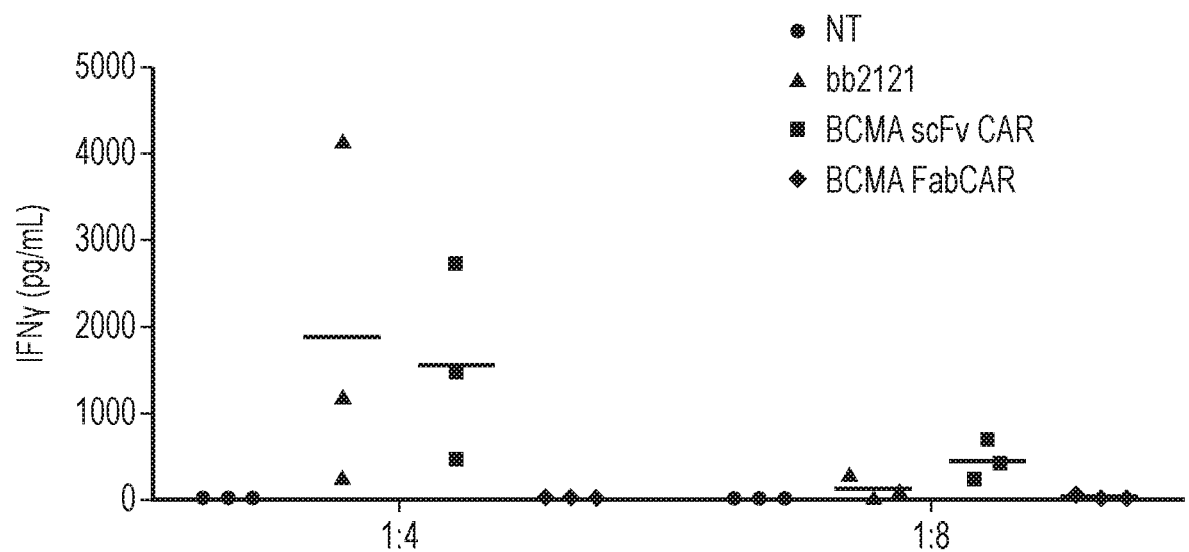
FIG. 7: IFNγ production by T-cells expressing an anti-BCMA CAR in either an scFv or FabCAR format following co-culture with target cells.
Figure 7B:
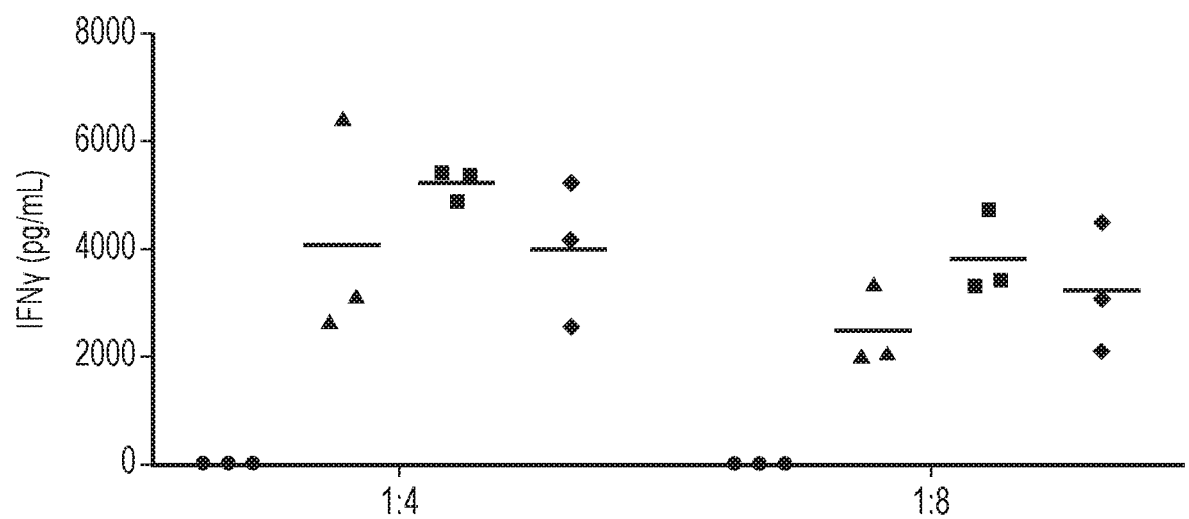

The results for IFNγ are shown in FIG. 7 for co-cultures carried out with antigen non BCMA-expressing target cells (FIG. 7A) or target cells expressing low levels of BCMA (FIG. 7B). The BCMA FabCAR-expressing T cells produced comparable levels of IFNγ following co-culture with BCMA-low expressing target cells than the equivalent scFv CAR. A higher background was observed with non-transduced SupT1 target cells for both bb2121 and the equivalent scFv CAR, than was observed with the FabCAR.

Example 6—Proliferation Assay (PA)

In order to measure proliferation, the same panel of CAR-expressing T cells described in example 4 were labelled with the dye Cell Trace Violet (CTV). T-cells were incubated with CTV for 20 minutes at 37° C. Subsequently, the cells were quenched by adding 5V of complete media. After a 5 minute incubation, the T-cells were washed and re-suspended in 2 ml of complete media. An additional 10 minute incubation at room temperature was carried out to allow acetate hydrolysis and retention of the dye. Labelled T-cells were co-cultured with non BCMA-expressing (SupT1 NT), low BCMA-expressing (SupT1 BCMAlow), very low BCMA-expressing (JeKo-1) or MM.1s target cells at a 1:1 ratio for 96 hours. The assay was carried out in a 96-well plate in 0.2 ml total volume using $5\times10^4$ transduced T-cells per well and an equal number of target cells (ratio 1:1). Following co-culture, the T-cells were analysed by flow cytometry to measure the dilution of the CTV, which occurs upon division of T-cells.

The cells were also gated on CD3 and the marker RQR8, then either CD8+ or CD8− to investigate the whole cell counts for CD4 and CD8 T cells. The results are shown in FIG. 8. The BCMA FabCAR showed high CD8 cell counts compared to the equivalent scFv CAR and bb2121 following co-culture with all three BCMA-expressing target cell types (low-expressing, very low-expressing and MM.1s targets) reflecting either greater proliferation and/or reduced cell death (FIG. 8B). Of note is also that the background proliferation for bb2121 and the scFv CAR was higher in CD4 cells than that observed for the FabCAR. This may give a higher apparent proliferation with target cells but in fact be reflecting increased activation of CAR in the absence of antigen.

Example 7—Design and Construction of Antibodies with Dual Variable Domains Equivalent to the Antigen-Binding Domain of a Cleavable FabCAR A cleavable FabCAR is illustrated schematically in FIG. 9. It comprises two antigen binding domains: an external (membrane-distal) binding domain 1 and an internal (membrane-proximal) binding domain 2. Binding domains 1 and 2 are joined by a cleavable linker. Cleavage of the linker by, for example, a matrix metalloproteinase (MMP) removes binding domain 1 from the CAR. In the absence of cleavage, when the FabCAR is intact, the internal binding domain is partially occluded by the presence of the external domain due to steric hindrance. The internal domain is activated upon cleavage of the heavy and light chain.

In order to show that it is possible to design a molecule with two binding domains and activate the internal binding domain by cleavage of the external binding domain with an enzyme, a soluble antibody was designed as shown in FIG. 10.

The antibody comprised a first antigen binding domain which binds BCMA and has the VH and VL sequences shown above as SEQ ID No. 29 and 30 respectively. The second antigen binding domain binds CD19 and has the VH and VL sequences shown above as SEQ ID No. 67 and SEQ ID No. 68 respectively.

An MMP-9 cleavable linker having the sequence PLGLAG (SEQ ID No. 87) was included between the two VL domains and between the two VH domains. As a negative control, a scrambled version of this sequence was used: LALGPG (SEQ ID No. 88).

Constructs were made as follows:
Plasmid 1: D8_MMP9_CAT19_HC_HuIgG1
Plasmid 2: D8_scrambled_CAT19_HC_HuIgG1
Plasmid 3: D8_MMP9_CAT19_LC
Plasmid 4: D8 scrambled CAT19 LC CHO cells were co-transfected either Plasmid 1 and Plasmid 3, so that they produced the antibody shown in FIG. 10 with an MMP-cleavable linker; or co-transfected with Plasmid 2 and Plasmid 4, so that they produced the equivalent antibody with a scrambled linker in the VH-containing chain and the VL-containing chain.

Example 8—Demonstration that the External Binding Domain of a Two-Binding Domain Antibody can be Cleaved Using an Enzyme The antibody described in Example 7 comprised a MMP-9 cleavable linker between the VH domains and the VL domains of the BCMA binding domain and the CD19 binding domain. In order to demonstrate that the BCMA-binding domain may be cleaved using the MMP-9 enzyme, a digestion assay was set up as follows.

Recombinant human MMP-9 was made up to 100 μg/mL in assay buffer. P-aminophenylmercuric acetate (APMA) was added to a final concentration of 1 mM to activate the enzyme and incubated at 37° C. for 24 hours.

Digestion assays were prepared by mixing 50 ug antibody and 6 ul activated enzyme in a final buffer volume of 200 ul. The digestion assay was incubated at 37° C. and 1 ug antibody solution (4 ul) was removed at various time points, resuspended in NuPAGE loading dye, boiled, frozen and then run on SDS-PAGE. The percentage cleavage was analysed by densitometry and the results are shown in FIG. 11.

The antibody containing the MMP-9 cleavable linker was digested over time by the matrix metalloproteinase, plateauing out after about 1 hour exposure to the enzyme. The antibody with the scrambled linker did not show a significant increase in digestion, even after 24 hours exposure to the enzyme.

Example 9—Investigating the Effect of Cleavage of the External Binding Domain on Binding to the Target Antigen for the Internal Binding Domain In order to investigate the activity of the internal binding domain with and without removal of the external binding domain, and ELISA assay was set up to investigate binding to CD19. Recombinant CD19 was coated on a 96-well plate at 1 ug/ml in 50 ul/well. After blocking, antibodies as described in Example 7 (either containing the MMP-9 or scrambled linkers and with or without prior exposure to MMP-9) were loaded at 15 ug/ml for 30' and then washed in PBS 0.05% Tween20. A secondary anti-human Fc HRP conjugated antibody was added at 1:3000 dilution incubated for 1h. Signal was detected with 1-step Ultra TMB substrate and blocked in 1M $H_2SO_4$. The results are shown in FIG. 12: The soluble antibody (D8-MMP-CAT19) showed increased binding to CD19 upon MMP-9 cleavage, whereas for the antibody having a scrambled linker (D8-scrambled-CAT19), CD19 binding was unaffected by prior exposure to MMP-9.

Example 10—Investigating the Effect of Cleavage of the External Binding Domain on the Kinetics of CD19 Binding CD19-binding kinetics were tested by capturing antibodies on a protein A chip on a Biacore 8K instrument. The antibody described for Example 8, with or without prior exposure to MMP-9, and a positive control antibody (CAT19 IgG) were captured at 75 RU for IgG and 100 RU for two-binding domain constructs. Recombinant CD19 was dialysed in HBS-EP+ buffer and analyte was tested at 500 nM with 2 fold serial dilutions. The results are shown in FIG. 13. The antibody with the MMP-9 cleavable linker showed increased Rmax of CD19 binding following cleavage with MMP-9 (D8-MMP9-CAT19 cleaved) than the equivalent antibody without exposure to MMP-9 (D8-MMP9-CAT19).

All publications mentioned in the above specification are herein incorporated by reference. Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

The invention claimed is:

1. A chimeric antigen receptor (CAR) which binds B cell maturation antigen (BCMA), wherein the CAR comprises a Fab antigen binding domain comprising the VH domain of SEQ ID NO: 29 and the VL domain of SEQ ID NO: 30.

2. A nucleic acid sequence which encodes a CAR according to claim 1.

3. A nucleic acid construct which encodes a CAR according to claim 1 and has one of the following general structures:
VH-CH-spacer-TM-endo-coexpr-VL-CL;
VL-CL-coexpr-VH-CH-spacer-TM-endo;
VL-CL-spacer-TM-endo-coexpr-VH-CH; or
VH-CH-coexpr-VL-CL-spacer-TM-endo;
in which:
VH is a nucleic acid sequence encoding a heavy chain variable region;
CH is a nucleic acid sequence encoding a heavy chain constant region
spacer is a nucleic acid encoding a spacer;
TM is a nucleic acid sequence encoding a transmembrane domain;
endo is a nucleic acid sequence encoding an endodomain;
coexpr is a nucleic acid sequence enabling co-expression of the first and second polypeptides;
VL is a nucleic acid sequence encoding a light chain variable region; and
CL is a nucleic acid sequence encoding a light chain constant region.

4. A nucleic acid construct according to claim 3 which also encodes a second chimeric antigen receptor having a domain antibody (dAb), scFv or Fab antigen binding domain.

5. A nucleic acid construct according to claim 4, wherein the second chimeric antigen receptor binds one of the following antigens: CD19, FcRL5 and TACI.

6. A vector which comprises a nucleic acid sequence according to claim 2.

7. A cytolytic immune cell which expresses a CAR according to claim 1.

8. A cytolytic immune cell which expresses a first CAR according to claim 1, and a second CAR which binds one of the following antigens: CD19, FcRL5 and TACI.

9. A cell according to claim 7, which also expresses a constitutively active cytokine receptor.

10. A method for making a cell according to claim 7, which comprises the step of introducing a nucleic acid which expresses the CAR into a cell ex vivo.

11. A pharmaceutical composition which comprises a plurality of cells according to claim 7, together with a pharmaceutically acceptable carrier, diluent or excipient.

12. A method for treating cancer which comprises the step of administering a pharmaceutical composition according to claim 11 to a subject.

13. A method according to claim 12, wherein the cancer is multiple myeloma.

14. A method for making a cell according to claim 8, which comprises the step of introducing into a cell ex vivo: (a) a first nucleic acid which expresses the first CAR and a second nucleic acid which expresses the second CAR, or (b) a nucleic acid which expresses both the first and the second CARs.

* * * * *